United States Patent
Röder et al.

(10) Patent No.: US 10,489,550 B2
(45) Date of Patent: Nov. 26, 2019

(54) PREDICTIVE TEST FOR AGGRESSIVENESS OR INDOLENCE OF PROSTATE CANCER FROM MASS SPECTROMETRY OF BLOOD-BASED SAMPLE

(71) Applicant: Biodesix, Inc., Boulder, CO (US)

(72) Inventors: Joanna Röder, Steamboat Springs, CO (US); Heinrich Röder, Steamboat Springs, CO (US); Carlos Oliveira, Steamboat Springs, CO (US)

(73) Assignee: BIODESIX, INC., Boulder, CO (US)

( * ) Notice: Subject to any disclaimer, the term of this patent is extended or adjusted under 35 U.S.C. 154(b) by 207 days.

(21) Appl. No.: 15/701,668

(22) Filed: Sep. 12, 2017

(65) Prior Publication Data
US 2018/0129780 A1 May 10, 2018

Related U.S. Application Data

(62) Division of application No. 14/869,348, filed on Sep. 29, 2015, now Pat. No. 9,779,204.

(60) Provisional application No. 62/058,792, filed on Oct. 2, 2014.

(51) Int. Cl.
| | |
|---|---|
| *G01N 24/00* | (2006.01) |
| *G06F 19/18* | (2011.01) |
| *H01J 49/40* | (2006.01) |
| *G01N 33/68* | (2006.01) |
| *G01N 33/574* | (2006.01) |
| *G06F 19/24* | (2011.01) |
| *H01J 49/00* | (2006.01) |

(52) U.S. Cl.
CPC ....... *G06F 19/18* (2013.01); *G01N 33/57434* (2013.01); *G01N 33/6851* (2013.01); *G06F 19/24* (2013.01); *H01J 49/40* (2013.01); *G01N 2800/56* (2013.01); *H01J 49/0036* (2013.01)

(58) Field of Classification Search
None
See application file for complete search history.

(56) References Cited

U.S. PATENT DOCUMENTS

| | | | |
|---|---|---|---|
| 6,578,003 | B1 | 6/2003 | Camarda |
| 7,736,905 | B2 | 6/2010 | Roder |
| 7,811,772 | B2 | 10/2010 | Semmes |
| 7,906,342 | B2 | 3/2011 | Roder |
| 8,440,409 | B2 | 5/2013 | Zhang |
| 8,718,996 | B2 | 5/2014 | Roder |
| 8,731,839 | B2 | 5/2014 | Bhanot |
| 2005/0282199 | A1 | 12/2005 | Slawin |
| 2007/0269804 | A1 | 11/2007 | Liew |

(Continued)

FOREIGN PATENT DOCUMENTS

WO 2014074821 A1 5/2014

OTHER PUBLICATIONS

Cooperberg et al., "Long-Term Active Surveillance for Prostate Cancer: Answers and Questions", Journal of Clinical Oncology, 33(3):238-240 (2015)*.

(Continued)

*Primary Examiner* — Xiaoyun R Xu
(74) *Attorney, Agent, or Firm* — DLA Piper LLP (US)

(57) ABSTRACT

A programmed computer functioning as a classifier operates on mass spectral data obtained from a blood-based patient sample to predict indolence or aggressiveness of prostate cancer. Methods of generating the classifier and conducting a test on a blood-based sample from a prostate cancer patient using the classifier are described.

7 Claims, 21 Drawing Sheets

(56) References Cited

U.S. PATENT DOCUMENTS

| | | |
|---|---|---|
| 2008/0187207 A1 | 8/2008 | Bhanot |
| 2009/0170215 A1 | 7/2009 | Roder |
| 2009/0208921 A1 | 8/2009 | Tempst |
| 2011/0142301 A1 | 6/2011 | Boroczky |
| 2011/0218950 A1 | 9/2011 | Mirowski |
| 2012/0121618 A1 | 5/2012 | Kantoff |
| 2013/0320203 A1 | 12/2013 | Roder |
| 2014/0106369 A1 | 4/2014 | Zhang |
| 2014/0284468 A1 | 9/2014 | Grigorieva |
| 2015/0102216 A1 | 4/2015 | Roder |

OTHER PUBLICATIONS

Klotz et al., "Long-Term Follow-Up of a Large Active Surveillance Cohort of Patients with Prostate Cancer", Journal of Clinical Oncology, 33(3):272-277 (2015)*.

Bartsch et al., "Tyrol Prostate Cancer Demonstration Project: early detection, treatment, outcome, incidence and morality", BJU International, 11:809-816 (2008)*.

Bill-Axelson eta l., "Radical Prostatectomy versus Watchful Waiting in Early Prostate Cancer", The New England Journal of Medicine, 364(18):1708-1717 (2011)*.

Cary et al., "Biomarkers in prostate cancer surveillance and screening: past, present, and future", Therapeutic Advances in Urology, 5(8):318-329 (2013)*.

Satori et al., "Biomarkers in prostate cancer: what's new?", Curr. Opin. Oncol., 26(3):259-264 (2014)*.

Tibshirani, "Regression Shrinkage and Selection via the Lasso", J.R. Statist. Soc. B, 58(1):267-288 (1996)*.

Girosi et al., "Regularization Theory and Neural Networks Architectures", Neural Computation, 7:219-269 (1995)*.

Tulyakov et al., "Review of Classifier Combination Methods", Studies in Computational Intelligence, 90:361-386 (2008)*.

Klein et al., "A 17-gene Assay to Predict Prostate Cancer Aggressiveness in the Context of Gleason Grade Heterogeneity, Tumor Multifocality, and Biopsy Undersampling", European Urology, 66:550-560 (2014)*.

Trock, "Circulating biomarkers for disciminating indolent from aggressive disease in prostate cancer active surveillance", Curr. Opin. Urol., 24:293-302 (2014)*.

Cooperberg et al., "Validation of a Cell-Cycle Progression Gene Panel to Improve Risk Stratification in a Contemporary Prostatectomy Cohort", Journal of Clincal Oncology, 31(11):1428-1434 (2013)*.

Srivastava, "Improving Neural Networks with Dropout", A thesis submitted in conformity with the requirements for the degree of Master of Science, Graduate Department of Computer Science, University of Toronto (2013)*.

Tikhonov, "On the Stability of Inverse Problems", Comptes Rendus (Doklady) de l'Academie des Sciences de l'URSS, 39(5):195-198 (1943)*.

Morash et al., "Active surveillance for the management of localized prostate cancer: Guideline recommendations", Can Urol Assoc J, 9(5-6):171-178 (2015)*.

Ladjevardi et al., "Prostate Biopsy Sampling Causes Hematogenous Dissemination of Epithelial Cellular Material", Disease Markers, 2014:1-6 (2014)*.

Faria et al., "Use of low free to total PSA ratio in prostate cancer screening: detection rates, clinical and pathological findings in Brazilian men with serum PSA levels < 4.0 ng/mL," BJU International, 110:E653-E657 (2012)*.

Written Opinion and International Search Report for corresponding PCT application No. PCT/US2015/052927, dated Feb. 2, 2016*.

Supplementary European Search Report for corresponding European application No. 15846544.3, dated May 24, 2018.

Wang et al., "Fast 'dropout' training for logistic regression", workshop on long-linear models at the 26th annual conference on Neural Information Processing Systems (2012), retrieved from internet on Apr. 8, 2014 at URL:https://docs.google.com/file/d/0B_9blvt8HjXzbGJTZ1pWczRyMGM/edit.

Al-Ruwaili et al., "Discovery of Serum Protein Biomarkers for Prostate Cancer Progression by Proteomic Analysis", Cancer Genomics & Proteomics, 7:93-104 (2010).

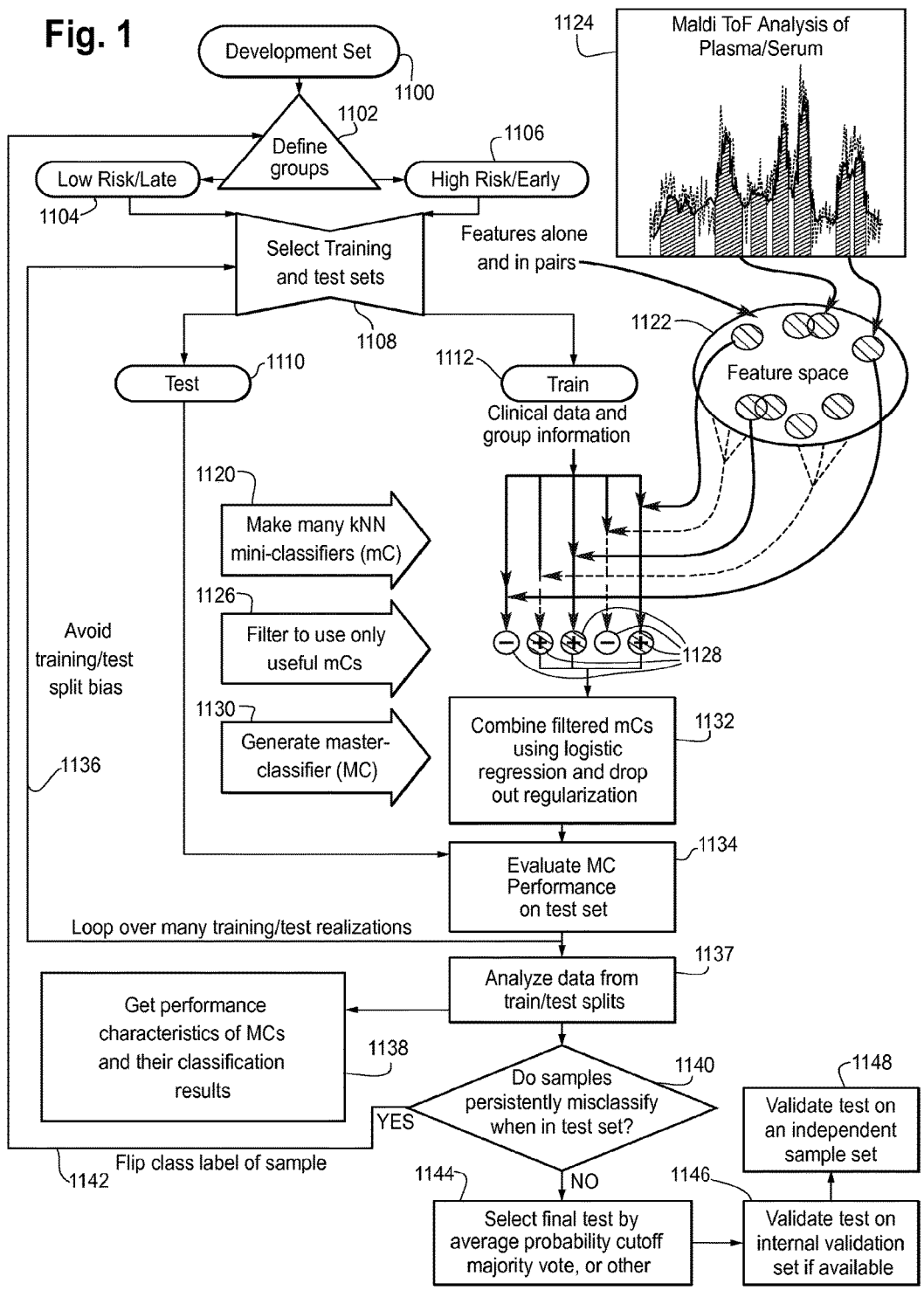

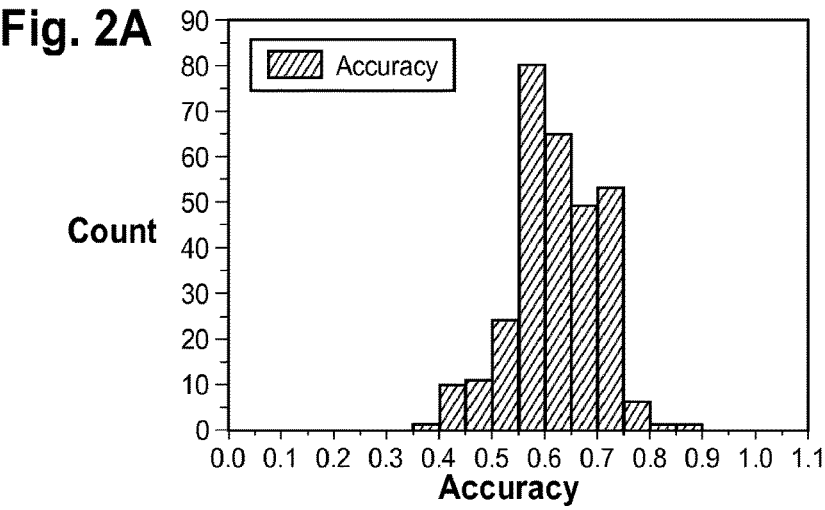
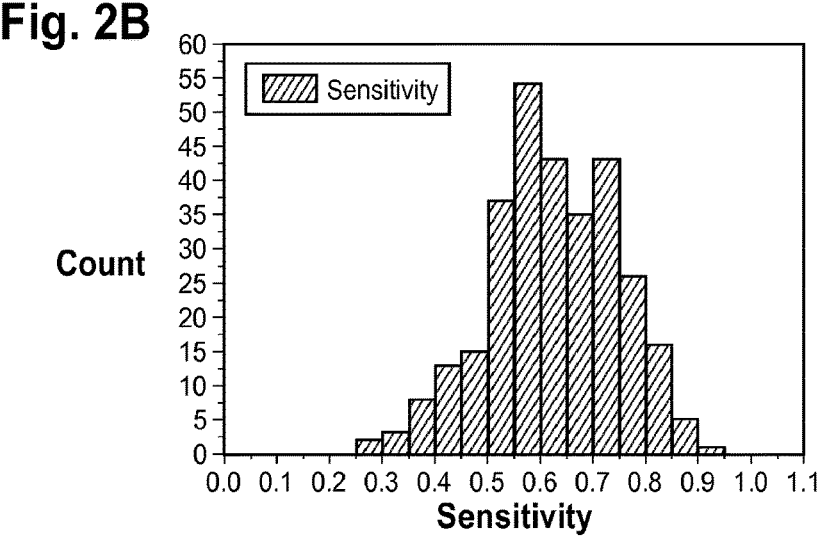
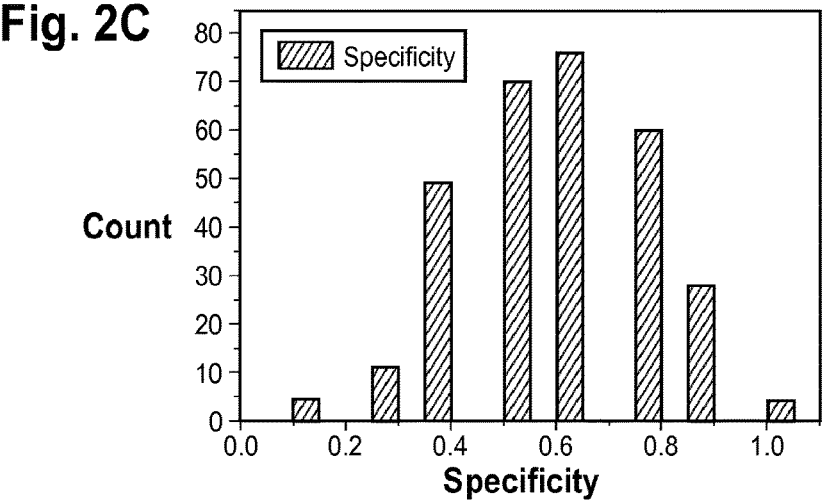

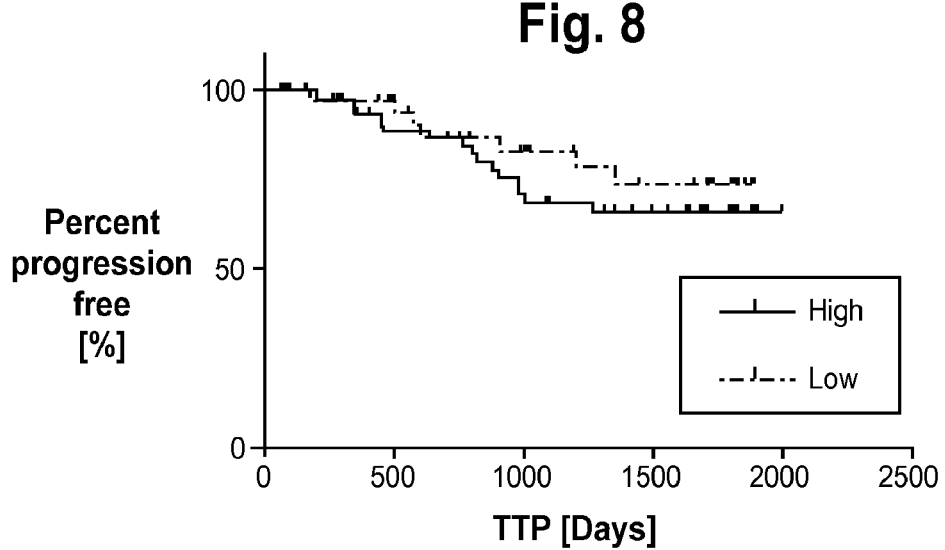
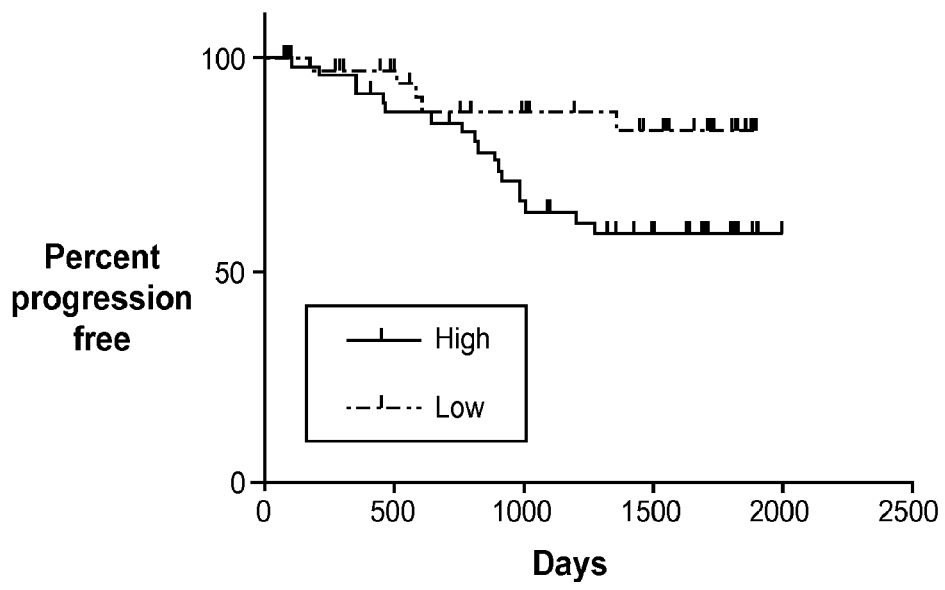

Fig. 12
| Iteration | Kaplan-Meier Curve | Outcome Metrics |
|---|---|---|
| 0 | 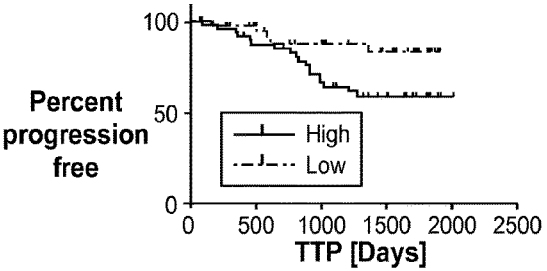 | p-value = 0.037<br>HR (log-rank) = 2.74<br>HR 95% CI: [1.05;5.49] |
| 1 | 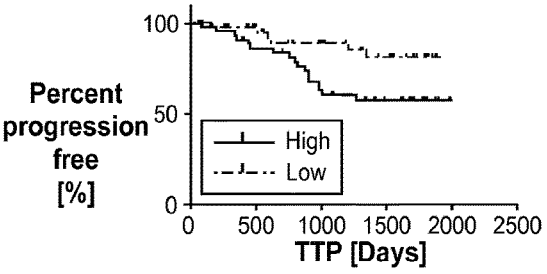 | p-value = 0.021<br>HR (log-rank) = 2.85<br>HR 95% CI: [1.16;5.94] |
| 2 | 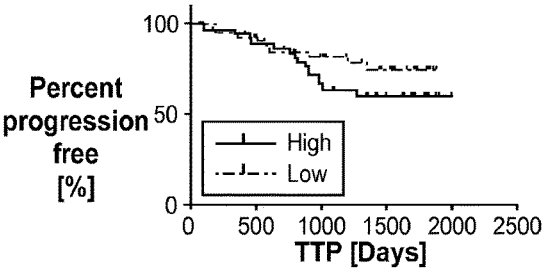 | p-value = 0.199<br>HR (log-rank) = 1.72<br>HR 95% CI: [0.75;3.88] |
| 3 | 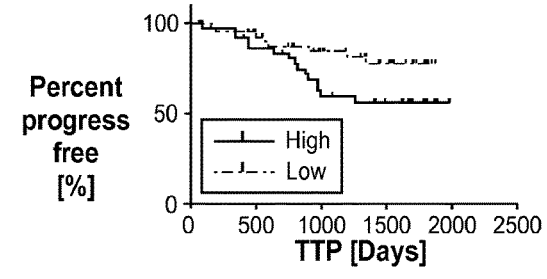 | p-value = 0.046<br>HR (log-rank) = 2.38<br>HR 95% CI: [1.02;5.26] |

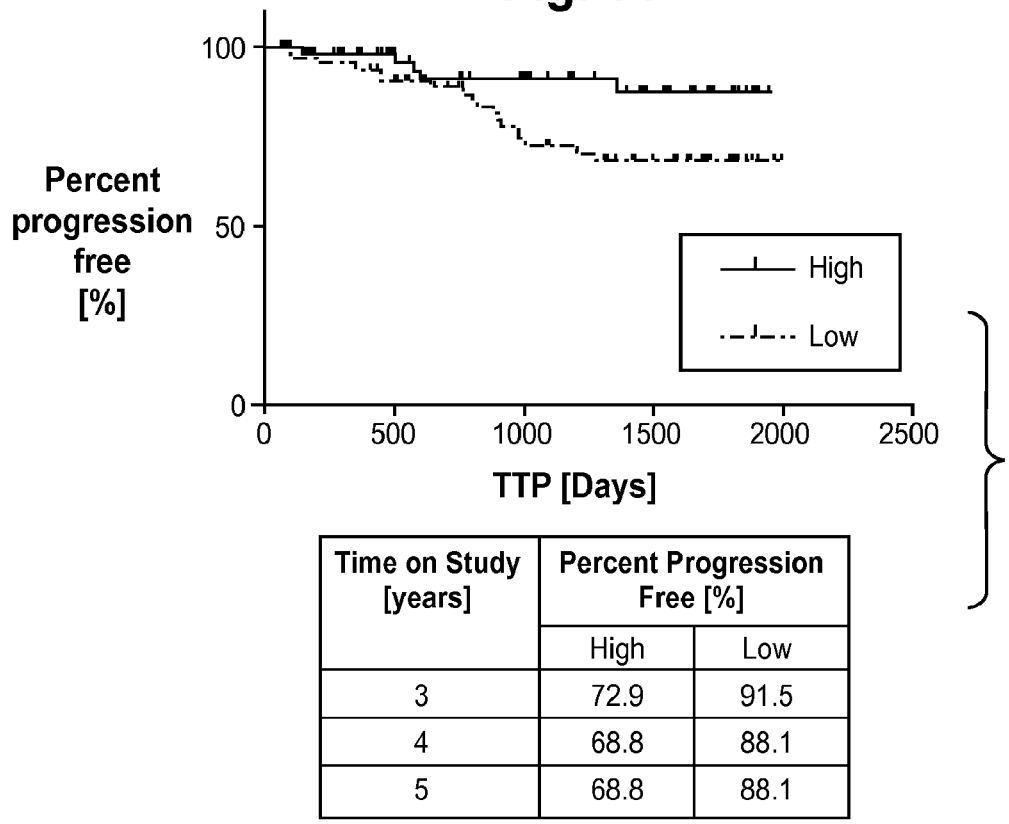
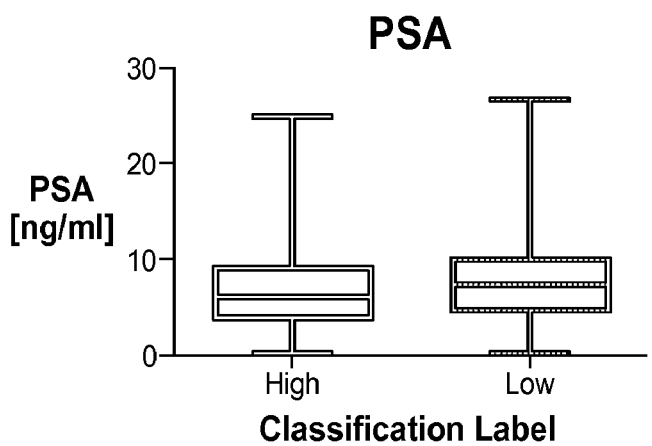

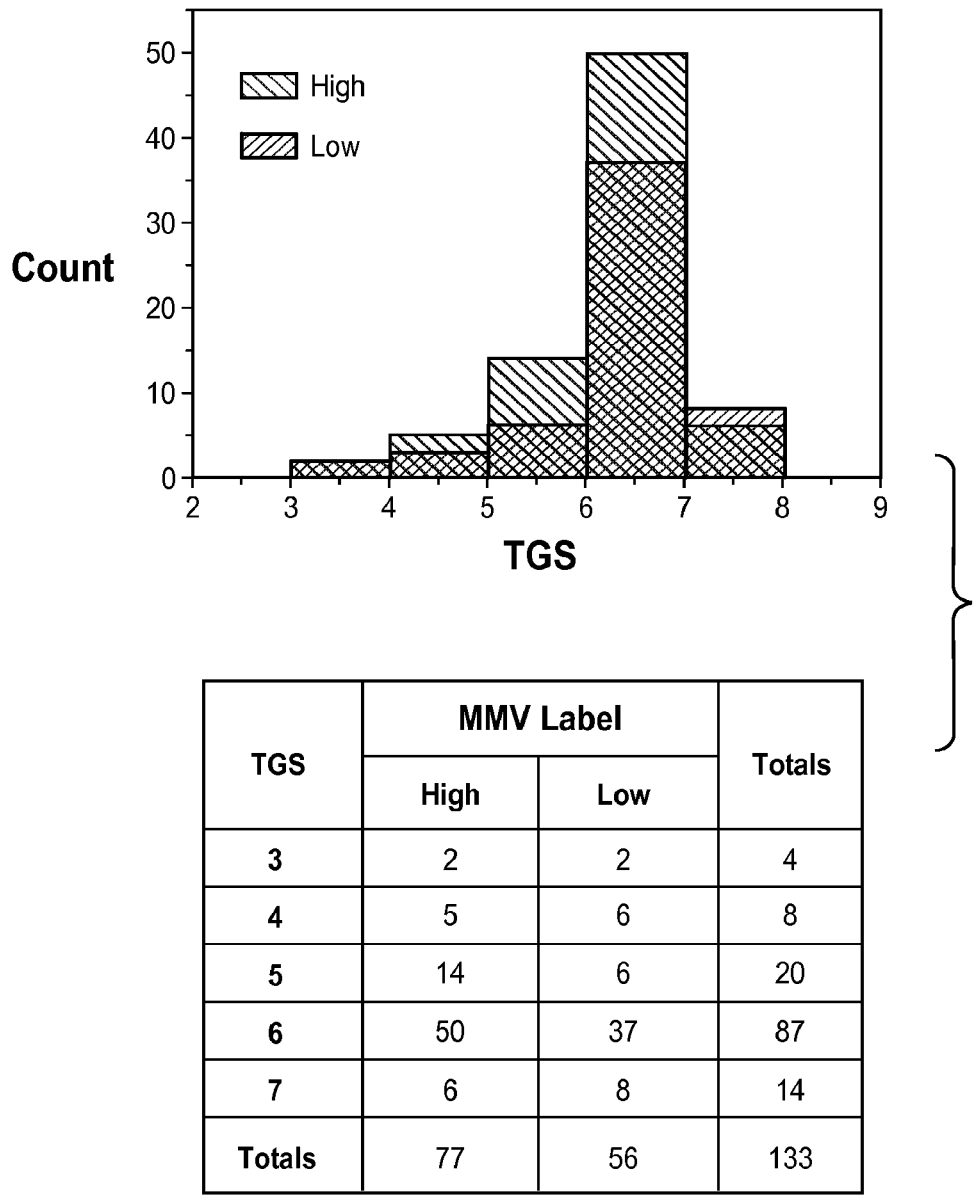

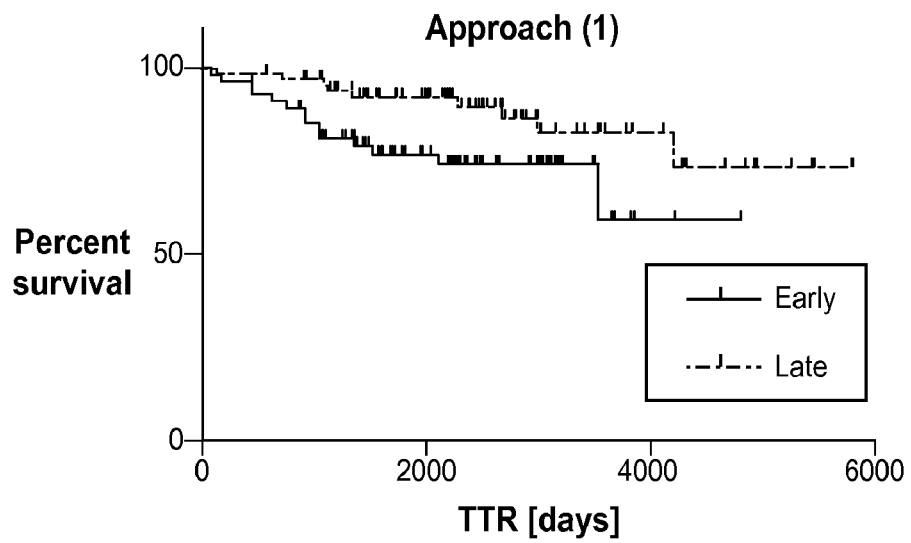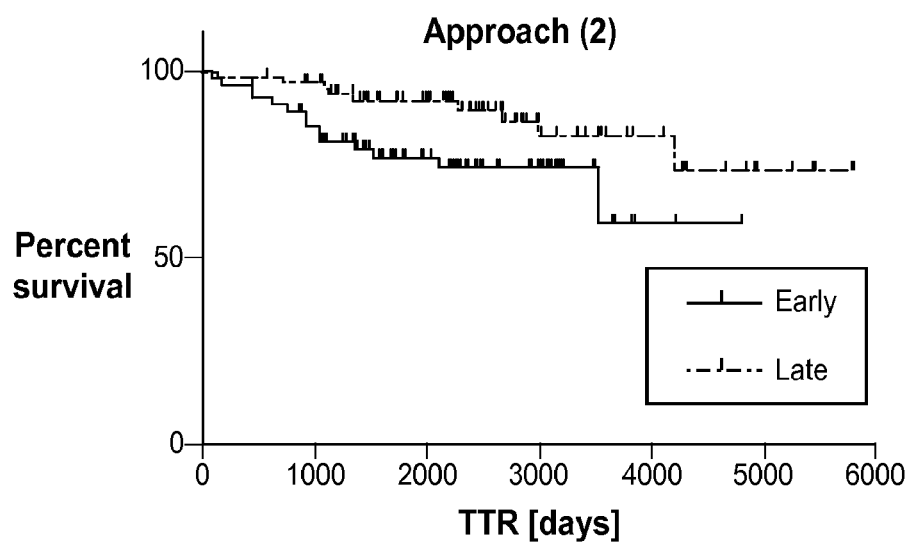

PREDICTIVE TEST FOR AGGRESSIVENESS OR INDOLENCE OF PROSTATE CANCER FROM MASS SPECTROMETRY OF BLOOD-BASED SAMPLE

RELATED APPLICATION

This application is a divisional application of U.S. Ser. No. 14/869,348, filed Sep. 29, 2015 (now U.S. Pat. No. 9,779,204), which claims priority benefits to U.S. provisional application Ser. No. 62/058,792 filed Oct. 2, 2014, the content of both which are incorporated by reference herein.

This application is related to U.S. application Ser. No. 14/486,442 filed Sep. 15, 2014, of H. Röder et al., U.S. patent application publication no. 2015/0102216, assigned to the assignee of the present invention. The content of the '442 application is incorporated by reference herein. The '442 application is not admitted to depict prior art.

BACKGROUND

Prostate cancer is a cancer that forms in tissues of the prostate, a gland in the male reproductive system. Prostate cancer usually occurs in older men. More than one million prostate biopsies are performed each year in the United States, leading to over 200,000 prostate cancer diagnoses. Managing the care of these patients is challenging, as the tumors can range from quite indolent to highly aggressive.

Current practice is to stratify patients according to risk based on serum prostate specific antigen (PSA) measurements, TNM staging, and Gleason score. High baseline PSA (PSA>20 ng/ml) is taken as a signal of increased risk of aggressive disease and indicates immediate therapeutic intervention. TNM staging of T3a or worse, including metastatic disease, places the patient in the high risk category, whereas a staging of T1 to T2a is required for the patient to be classified as low or very low risk.

In order to have the Gleason score evaluated, a set of biopsies are taken from different regions of the prostate, using hollow needles. When seen through a microscope, the biopsies may exhibit five different patterns (numbered from 1 to 5), according to the distribution/shape/lack of cells and glands. A pathologist decides what the dominant pattern is (Primary Gleason Score) and the next-most frequent pattern (Secondary Gleason Score). The Primary and Secondary scores are then summed up and a Total Gleason Score (TGS) is obtained, ranging from 2 to 10. As the TGS increases the prognosis worsens. Patients with Gleason score of 8 or higher are classified as high risk and are typically scheduled for immediate treatment, such as radical prostatectomy, radiation therapy and/or systemic androgen therapy. Patients with Gleason score of 7 are placed in an intermediate risk category, while patients with Gleason score of 6 or lower are classified as low or very low risk.

Patients diagnosed with very low, low, and intermediate risk prostate cancer are assigned to watchful waiting, an active surveillance protocol. For these patients, levels of serum PSA are monitored and repeat biopsies maybe ordered every 1-4 years. However, despite low baseline PSA and favorable biopsy results, some patients defined as low risk do experience rapid progression. These patients, especially in the younger age group, would benefit from early intervention. Bill-Axelson, A. et al. *Radical prostatectomy versus watchful waiting in early prostate cancer*. N Engl J Med 364, 1708-17 (2011). Improved identification of prostate cancer patients who in fact have poor prognosis and need to be actively treated is of significant clinical importance.

Investigations into various biomarkers which may help in this indication are ongoing. While measurement of total PSA remains one of the most widely accepted tests for prostate cancer diagnostics, a lot of research is focused on finding additional circulating biomarkers of prognosis of the course of the disease. Several alternative types of PSA measurements, such as percentage of free PSA (% fPSA) and PSA kinetics have been evaluated most extensively. Observed % fPSA seems to be a significant predictor of time to treatment in patients in active surveillance, while PSA velocity and PSA doubling time results are often inconsistent. Trock, B. J. *Circulating biomarkers for discriminating indolent from aggressive disease in prostate cancer active surveillance*. Curr Opin Urol 24, 293-302 (2014); Cary, K. C. & Cooperberg, M. R. *Biomarkers in prostate cancer surveillance and screening: past, present, and future*. Ther Adv Urol 5, 318-29 (2013). Another test based on calculating the Prostate Health Index using measurements of [−2]proPSA (a truncated PSA isoform), fPSA and total PSA, has shown promising results. See the Trock paper, supra. Several studies evaluated potential biomarkers in urine, such as prostate cancer antigen3 (PCA3) and fusion gene TMPRSS2-EGR, though the results were contradictory. Id. In addition, there are several recent tissue based tests employing gene expression profiles, such as Oncotype DX Prostate Cancer Assay (Genomic health) see Klein, A. E., et al. *A 17-gene Assay to Predict Prostate Cancer Aggressiveness in the Context of Gleason Grade Heterogeneity, Tumor Multifocality, and Biopsy Undersampling*, Euro Urol 66, 550-560 (2014) and the Prolaris assay (Myriad Genetics), see Cooperberg, M. R., et al. *Validation of a Cell-Cycle Progression Gene Panel to Improve Risk Stratification in a Contemporary Prostatectomy Cohort*, J Clin Oncol 31, 1428-1434 (2013), which are associated with the risk of disease progression (see Sartori, D. A. & Chan, D. W. *Biomarkers in prostate cancer: what's new?* Curr Opin Oncol 26, 259-64 (2014)) however they require an invasive procedure.

Though the results on a number of biomarkers are promising, most are in early stages of validation and none of them has yet been shown to reliably predict the course of the disease. Thus, there is an unmet need for non-invasive clinical tests that would improve risk discrimination of prostate cancer in order to help select appropriate candidates for watchful waiting and identify men who need an immediate active treatment. The methods and systems of this invention meet that need.

Other prior art of interest includes U.S. Pat. Nos. 8,440,409 and 7,811,772, and U.S. patent application publication 2009/0208921. The assignee of the present invention has several patents disclosing classifiers for predictive tests using mass spectrometry data including, among others, U.S. Pat. Nos. 7,736,905; 8,718,996 and 7,906,342.

SUMMARY

In a first aspect, a method for predicting the aggressiveness or indolence of prostate cancer in a patient previously diagnosed with prostate cancer is disclosed. The method includes the steps of: obtaining a blood-based sample from the prostate cancer patient; conducting mass spectrometry of the blood-based sample with a mass spectrometer and thereby obtaining mass spectral data including intensity values at a multitude of m/z features in a spectrum produced by the mass spectrometer, and performing pre-processing operations on the mass spectral data, such as for example background subtraction, normalization and alignment. The method continues with a step of classifying the sample with a programmed computer implementing a classifier. In preferred embodiments the classifier is defined from one or more master classifiers generated as combination of filtered mini-classifiers with regularization. The classifier operates on the intensity values of the spectra obtained from the sample after the pre-processing operations have been performed and a set of stored values of m/z features from a constitutive set of mass spectra.

In this document we use the term "constitutive set of mass spectra" to mean a set of feature values of mass spectral data which are used in the construction and application of a classifier. The final classifier produces a class label for the blood based sample of High, Early, or the equivalent, signifying the patient is at high risk of early progression of the prostate cancer indicating aggressiveness of the prostate cancer, or Low, Late or the equivalent, signifying that the patient is at low risk of early progression of the prostate cancer indicating indolence of the cancer.

In one embodiment, in which the classifier is defined from one or more master classifiers generated as a combination of filtered mini-classifiers with regularization, the mini-classifiers execute a K-nearest neighbor classification (k-NN) algorithm on features selected from a list of features set forth in Example 1 Appendix A, Example 2 Appendix A, or Example 3 Appendix A. The mini-classifiers could alternatively execute another supervised classification algorithm, such as decision tree, support vector machine or other. In one embodiment, the master classifiers are generated by conducting logistic regression with extreme drop-out on mini-classifiers which meet predefined filtering criteria.

In another aspect, a system for prostate cancer aggressiveness or indolence prediction is disclosed. The system includes a computer system including a memory storing a final classifier defined as a majority vote of a plurality of master classifiers, a set of mass spectrometry feature values, subsets of which serve as reference sets for the mini-classifiers, a classification algorithm (e.g., k-NN), and a set of logistic regression weighting coefficients defining one or more master classifiers generated from mini-classifiers with regularization. The computer system includes program code for executing the master classifier on a set of mass spectrometry feature values obtained from mass spectrometry of a blood-based sample of a human with prostate cancer.

In still another example, a laboratory test system for conducting a test on a blood-based sample from a prostate cancer patient to predict aggressiveness or indolence of the prostate cancer is disclosed. The system includes, in combination, a mass spectrometer conducting mass spectrometry of the blood-based sample thereby obtaining mass spectral data including intensity values at a multitude of m/z features in a spectrum produced by the mass spectrometer, and a programmed computer including code for performing pre-processing operations on the mass spectral data and classifying the sample with a final classifier defined by one or more master classifiers generated as a combination of filtered mini-classifiers with regularization. The final classifier operates on the intensity values of the spectra from a sample after the pre-processing operations have been performed and a set of stored values of m/z features from a constitutive set of mass spectra. The programmed computer produces a class label for the blood-based sample of High, Early or the equivalent, signifying the patient is at high risk of early progression of the prostate cancer indicating aggressiveness of the prostate cancer, or Low, Late or the equivalent, signifying that the patient is at low risk of early progression of the prostate cancer indicating indolence of the cancer.

In yet another aspect, a programmed computer operating as a classifier for predicting prostate cancer aggressiveness or indolence is described. The programmed computer includes a processing unit and a memory storing a final classifier in the form of a set of feature values for a set of mass spectrometry features forming a constitutive set of mass spectra obtained from blood-based samples of prostate cancer patients, and a final classifier defined as a majority vote or average probability cutoff, of a multitude of master classifiers constructed from a combination of mini-classifiers with dropout regularization.

In one possible embodiment, the mass spectrum of the blood-based sample is obtained from at least 100,000 laser shots in MALDI-TOF mass spectrometry, e.g., using the techniques described in the patent application of H. Röder et al., U.S. Ser. No. 13/836,436 filed Mar. 15, 2013, the content of which is incorporated by reference herein.

BRIEF DESCRIPTION OF THE DRAWINGS

FIG. 1 is a flow chart showing a classifier generation process referred to herein as combination of mini-classifiers with drop-out (CMC/D) which was used in generation of the classifiers of Examples 1, 2 and 3.

FIGS. 2A-2C are plots of the distribution of the performance metrics among the master classifiers (MCs) for Approach 1 of Example 1.

FIG. 8 is a plot of the Kaplan-Meier curves for TTP for the classifications obtained in Approach 1 of Example 2, including half (46) of the patients who dropped out of the study. For the patients who were used in the test/training splits, the MMV label is taken. For those patients who dropped out of the study the normal Majority Vote of all the 301 MCs is used. Log-rank test p-value=0.42, log-rank HR=1.42 with a 95% CI=[0.61-3.33].

FIG. 9 is a plot of the Kaplan-Meier curves for TTP using the MMV classification labels obtained in Approach 2 of Example 2.

FIG. 12 are Kaplan-Meier curves for TTP obtained using the MMV classification labels after each iteration of label flips (using Approach 2 of Example 2 as the starting point) in the classifier development process of FIG. 1. The log-rank p-value and the log-rank Hazard Ratio (together with its 95% Confidence Interval) are also shown for each iteration.

FIG. 14 is a plot of Kaplan-Meier curves for TTP using classification labels obtained in approach 2 of Example 2 and including the patients of the "validation set" cohort. For the patients that were used in the test/training splits the MMV label is taken. For the "validation set" patients, the normal majority vote of all the 301 MCs is used. The log-rank p-value is 0.025 and the log-rank Hazard Ratio 2.95 with a 95% CI of [1.13,5.83]. A table showing the percent progression free for each classified risk group at 3, 4 and 5 years on study is also shown.

FIG. 15 are Box and Whisker plots of the distribution of the PSA baseline levels (taken at the beginning of the study) of the two classification groups in Approach 2 of Example 2. For the patients that were used in the test/training splits the MMV label is taken. For the "validation set" patients, the normal majority vote of all the 301 MCs is used. The plot takes into account only the 119 patients (from the development and "validation" sample sets), for whom baseline PSA levels were available.

FIG. 16 is a plot of the distribution of the Total Gleason Score (TGS) values of the two classification groups (using Approach 2 of Example 2). For the patients that were used in the test/training splits the MMV label is taken. For the "validation set" patients, the normal majority vote of all the 301 MCs is used. Only the 133 patients (from the development and validation sets) for whom TGSs were available are considered in this plot.

FIGS. 20A and 20B are Kaplan-Meier plots for time to relapse (TTR) by Early and Late classification groups, showing the performance of the classifiers generated in Example 3. FIG. 20A shows the classifier performance for Approach (1) of Example 3, which uses only mass spectral data for classification, whereas FIG. 20B shows classifier performance for Approach (2) of Example 3, which uses non-mass spectral information, including patient's age, PSA and % fPSA, in addition to the mass spectral data.

DETAILED DESCRIPTION

Introduction

Figure 3A:
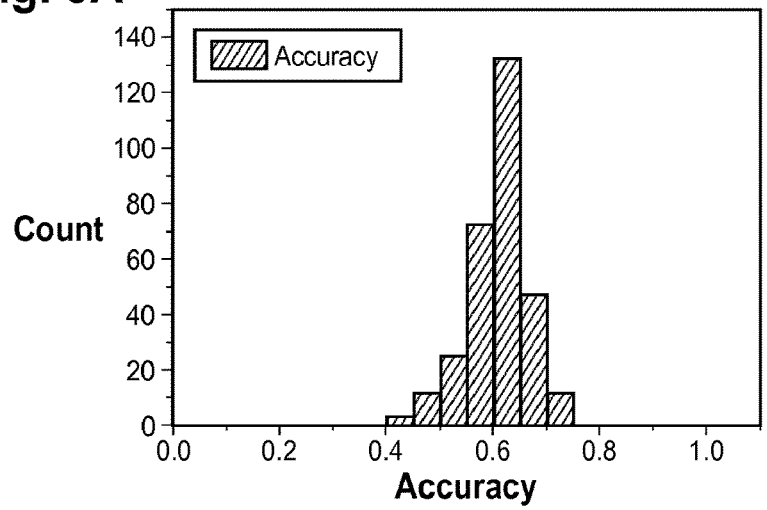
FIGS. 3A-3C are plots of the distribution of the performance metrics among the MCs for Approach 2 of Example 1.

A programmed computer is described below which implements a classifier for predicting from mass spectrometry data obtained from a blood-based sample from a prostate cancer patient whether the cancer is aggressive or indolent. The method for development of this classifier will be explained in three separate Examples using three different sets of prostate cancer blood-based samples. The classifier development process, referred to herein as "CMC/D" (combination of mini-classifiers with dropout) incorporates the techniques which are disclosed in U.S. application Ser. No. 14/486,442 filed Sep. 15, 2014, the content of which is incorporated by reference herein. The pertinent details of the classifier development process are described in this document in conjunction with FIG. 1. A testing system, which may be implemented in a laboratory test center including a mass spectrometer and the programmed computer, is also described later on in conjunction with FIG. 21.

Example 1: Classifier Development from Oregon Data Set

In this Example, we will describe the generation of a classifier to predict prostate cancer aggressiveness or indolence from a set of prostate cancer patient data in the form of blood-based samples obtained from prostate cancer patients and associated clinical data. This Example will describe the process we used for generating mass spectrometry data, pre-processing steps which were performed on the mass spectra, and the specific steps we used in development of a classifier from the set of data. This set of data is referred to as the "development set" 1100 of FIG. 1.

The patients included in this data set all had prostate biopsies and an evaluation of their Gleason Scores made (distributed according to Table 1). 18 of them were classified as low risk, 28 as intermediate risk and 29 as high risk, according to existing guidelines.

Available Samples

Serum samples were available from 79 patients diagnosed with prostate cancer.

Mass Spectral Data Acquisition

A. Sample Preparation

Samples were thawed on ice and spun at 1500 g for 5 minutes at 4° C. Each sample was diluted 1:10 with water and then mixed 1:1 with sinapinic acid (25 mg/ml in 50% ACN/0.1% TFA). The samples were spotted in triplicate.

B. Acquisition of Mass Spectra

Spectra of nominal 2,000 shots were collected on a MALDI-TOF mass spectrometer using acquisition settings we used in the commercially available VeriStrat test of the assignee Biodesix, Inc., see U.S. Pat. No. 7,736,905, the details of which are not particularly important. Spectra could not be acquired from two samples.

C. Spectral Pre-Processing

The data set consists originally of 237 spectra corresponding to 79 patients (3 replicates per patient). The spectra of 4 patients were not used for the study:

Patient 28 did not have any clinical data available
Patients 30 and 31 had clinical data available but spectra were not available for them
Patient N-37-1 had the Total Gleason Score (TGS) available but neither of the Primary or Secondary Scores In total 75 patients were used in the study, distributed through the following Primary/Secondary Gleason Score combinations:

TABLE 1

Distribution of the patients included in this analysis according to their primary and secondary Gleason Score combinations

| Progression Risk | Primary GS | Secondary GS | Total GS | #Patients |
|---|---|---|---|---|
| "Low" | 3 | 3 | 6 | 18 |
| "Int" | 3 | 4 | 7 | 20 |
|  | 4 | 3 | 7 | 8 |
| "High" | 4 | 4 | 8 | 13 |
|  | 3 | 5 | 8 | 1 |
|  | 5 | 3 | 8 | 2 |
|  | 4 | 5 | 9 | 11 |
|  | 5 | 4 | 9 | 1 |
|  | 5 | 5 | 10 | 1 |

D. Averaging of Spectra to Produce One Spectrum Per Sample

For each of the 3 replicate spectra available for each patient, the background was estimated and then subtracted. Peaks passing a SNR threshold of 6 were identified. The raw spectra (no background subtraction) were aligned using a subset of 15 peaks (Table 2) to correct for slight differences in mass divided by charge (m/z) scale between replicate spectra. The aligned spectra were averaged resulting in a single average spectrum for each patient. With the exception of alignment, no other preprocessing was performed on the spectra prior to averaging.

TABLE 2

Calibration points used to align the raw spectra prior to averaging
Calibration point m/z [Da]

| |
|---|
| 4153 |
| 6432 |
| 6631 |
| 8917 |
| 9433 |
| 9723 |
| 12864 |
| 13764 |
| 13877 |
| 14046 |
| 15127 |
| 15869 |
| 18630 |
| 21066 |
| 28100 |

Feature Definitions for New Classifier Development

Using a subset of 20 of the averaged spectra, background was subtracted using the same parameters as in the previous step. They were then normalized using Partial Ion Current (PIC) normalization and the normalization windows shown in Table 3. A total of 84 features were identified by overlaying the spectral sample averages and assessing the spread of the band from the overlay to define the left and right boundaries. When identified, oxidation states were combined into single features. The feature definitions are given in Example 1, Appendix A at the end of this document.

TABLE 3

Windows used in the initial PIC normalization, before feature definition

| Min m/z | Max m/z |
|---|---|
| 3000 | 4138 |
| 4205 | 11320 |

TABLE 3-continued

Windows used in the initial PIC normalization, before feature definition

| Min m/z | Max m/z |
|---|---|
| 12010 | 15010 |
| 16320 | 23000 |

Normalization of the Averaged Spectra

Using all pre-processed, averaged spectra, a set of features, stable across patient spectra, was determined that was suitable for a refined Partial Ion Current (PIC) normalization. These features are listed in Table 4.

TABLE 4

Features used in the final PIC normalization.
For further details on the feature ranges see Example 1 Appendix A.
Feature (m/z position)

| |
|---|
| 3330 |
| 5071 |
| 5109 |
| 5293 |
| 6591 |
| 6653 |
| 6797 |
| 6860 |
| 6891 |
| 6836 |
| 6947 |
| 13706 |
| 13758 |
| 13798 |
| 13877 |
| 13970 |

Using this optimized PIC normalization, a new feature table, containing all feature values for all samples, was constructed for all the patients and used during the subsequent classifier development steps of FIG. 1.

CMC/D Process for New Classifier Development

The new classifier development process using the method of combination of mini-classifiers (mCs) with dropout (CMC/D) is shown schematically in FIG. 1. The steps in this process are explained in detail below. The methodology, and its various advantages are explained in great detail in U.S. patent application Ser. No. 14/486,442 filed Sep. 15, 2014. See U.S. patent application publication no. 2015/0102216, H. Roder et al. inventors, which is incorporated by reference herein.

Division of Samples into Development and Validation Sets

Given the low number of patients (75), all of them were used as a development set 1100 (FIG. 1) for classifier development and no separate validation set was available.

Step 1102 Definition of Initial Groups

The only available clinical data for each patient was the Primary, Secondary and Total Gleason Scores. Generally, the higher the Total Gleason Score (TGS) the poorer is the prognosis for the patient (although the same TGS, obtained from two different combinations of Primary and Secondary Gleason Scores might be considered of different risk). Because there is no well-defined boundary between High and Low risk based in this grading system and because the evaluation of a score is somewhat subjective, we considered two different arrangements of the patients in terms of group labels:

Approach 1. The patients were arranged according to the prognostic risk depicted in Table 1. The "Low" (18 patients) and "High" (29 patients) were used to construct a binary CMC/D classifier (considering as "positive" outcome the "High" group). The patients with intermediate cancer risk (labeled as "Int") were left aside and later evaluated with the resulting CMC/D classifier.

Approach 2. In this approach, the "Low" training/test group 1104 consisted of the patients with both low and intermediate prognostic risks, comprising a total of 46 patients. The "High" group 1106 was the same as in Approach 1, comprising the 29 patients with high prognostic risk in Table 1. Thus, in this approach all the samples were used in the test/training splits when creating the CMC/D classifiers.

Step 1108 Select Training and Test Sets

Once the initial definition of the class groupings has been established and assignment of group labels to the members of the development set is made, the development set 1100 is split in step 1108 into test and training sets, shown in FIG. 1 as 1110 and 1112. The training set group 1112 was then subject to the CMC/D classifier development process shown in steps 1120, 1126 and 1130 and the master classifier generated at step 1130 was evaluated by classifying those samples which were assigned to the test set group 1110 and comparing the resulting labels with the initial ones.

Step 1120 Creation of Mini-Classifiers

Many k-nearest neighbor (kNN) mini-classifiers (mCs) that use the training set as their reference set are constructed using single features or pairs of features from the 84 mass spectral features identified (1124), and listed in Example 1 Appendix A. Basically, as explained in this example, samples are spotted in triplicate on a MALDI-TOF sample plate and a 2,000 shot spectrum is acquired from each spot. The three replicate spectra are aligned and averaged to yield one average spectrum per sample. Features for use in classification are defined as mass/charge (m/z) regions in MALDI spectra (shown as the distinct regions in the inset of 1124) and feature values are the integrated area under the curve for these regions (integrated intensity values). For 84 features, this amounts to considering 3,570 possible mCs. The parameters used to traverse the space of mCs for this project are listed in Table 5.

TABLE 5

Parameters used to create mCs

| kNN parameters: | k = 5 |
|---|---|
| mC traversal parameters: | Max number of features = 2 |

Each mini-classifier is created using the known k-NN algorithm and either a single feature or a pair of features from feature space 1122.

Step 1126 Filtering of Mini-Classifiers

To target a final classifier that has optimal performance characteristics, these mCs were filtered. Each mC was applied to its training set and performance metrics were calculated from the resulting classifications. Only mCs that satisfied thresholds on these performance metrics (shown as + in step 1128) passed filtering to be used further in the process. For this project filtering was based on classification accuracy, overall and within each reference class ("High" and "Low") separately.

Step 1130 and 1132 Generation of Master Classifier (MC) by Combination of Mini-Classifiers Using Logistic Regression with Dropout (CMC/D)

Once the filtering of the mCs is complete, a master classifier (MC) is generated in step 1130. In this step, the mCs are combined in one master classifier (MC) using a logistic regression trained using the training set labels as indicated at 1132. To help avoid over-fitting, the regression is regularized using extreme drop out. A total of 5 randomly selected mCs are included in each logistic regression iteration and the weights for the mCs averaged over 6,000 dropout iterations.

While similar in spirit to standard classifier combination methods (see e.g. S. Tulyakov et al, Review of Classifier Combination Methods, Studies in Computational Intelligence, Volume 90, 2008, pp. 361-386), we have the particular problem (with many more mCs than instances (samples in training set) that some "mini-classifiers" could be artificially perfect just by random chance, and hence would dominate the combinations. To avoid this overfitting to particular dominating "mini-classifiers", we generate many logistic training steps by randomly selecting only a small fraction of the "mini-classifiers" for each of these logistic training steps. This is a regularization of the problem in the spirit of dropout as used in deep learning theory. In this case, where we have many mini-classifiers and a small training set we use extreme dropout, where in excess of 99% of pre-filtered mini-classifiers are dropped out in each iteration.

Other methods for performing the regularized combination of the mini-classifiers that could be used include:

Logistic regression with a penalty function like ridge regression (based on Tikhonov regularization, Tikhonov, Andrey Nikolayevich (1943). " Об устойчивости обратных задач " [On the stability of inverse problems]. Doklady Akademii Nauk SSSR 39 (5): 195-198.)

The Lasso method (Tibshirani, R. (1996). *Regression shrinkage and selection via the lasso*. J. Royal. Statist. Soc B., Vol. 58, No. 1, page1138s 267-288).

Neural networks regularized by drop-out (Nitish Shrivastava, "*Improving Neural Networks with Dropout*", Master's Thesis, Graduate Department of Computer Science, University of Toronto; available at online from the Computer Science department of the University of Toronto).

General regularized neural networks (Girosi F. et al, Neural computation, (7), 219 (1995)). The above-cited publications are incorporated by reference herein.

In more detail, in step 1132, the result of each mini-classifier is one of two values, either "Low" or "High". We can then use logistic regression to combine the results of the mini-classifiers in the spirit of a logistic regression by defining the probability of obtaining a "Low" via standard logistic regression (see e.g. http://en.wikipedia.org/wiki/Logistic_regression)

$$P(\text{"Low"} | \text{feature for a spectrum}) = \frac{\exp\left(\sum_{mini\,classifiers} w_{mc} I(mc(\text{feature values}))\right)}{\text{Normalization}} \quad \text{Eq. (1)}$$

where $I(mc(\text{feature values}))=1$, if the mini-classifier mc applied to the feature values of a sample returns "Low", and 0 if the mini-classifier returns "High". The weights $w_{mc}$ are unknown and need to be determined from a regression fit of the above formula for all samples in the training set using 1 for the left hand side of the formula for the Low-labeled samples in the training set, and 0 for the High-labeled samples, respectively. As we have many more mini-classifiers, and therefore weights, than samples, typically thousands of mini-classifiers and only tens of samples, such a fit will always lead to nearly perfect classification, and can easily be dominated by a mini-classifier that, possibly by random chance, fits the particular problem very well. We do not want our final test to be dominated by a single special mini-classifier which only performs well on this particular set and is unable to generalize well. Hence we designed a method to regularize such behavior: Instead of one overall regression to fit all the weights for all mini-classifiers to the training data at the same time, we use only a few of the mini-classifiers for a regression, but repeat this process many times. For example we randomly pick three of the mini-classifiers, perform a regression for their three weights, pick another set of three mini-classifiers, and determine their weights, and repeat this process many times, generating many random picks, i.e. realizations of three mini-classifiers. The final weights defining the CMC/D master classifier are then the averages of the weights over all such realizations. The number of realizations should be large enough that each mini-classifier is very likely to be picked at least once during the entire process. This approach is similar in spirit to "drop-out" regularization, a method used in the deep learning community to add noise to neural network training to avoid being trapped in local minima of the objective function.

Step 1134 Evaluate Master Classifier Performance

At step 1134, the MC created at step 1130 is then evaluated by performing classification on the test set 1110 and evaluating the results. Methods of evaluating classifier performance are described in U.S. Ser. No. 14/486,442 filed Sep. 15, 2014 and include, among others, the distribution of Hazard Ratios, overall accuracy, sensitivity and specificity.

Step 1136 Loop Over Many Training/Test Set Splits

At step 1136, the process loops back to step 1108 and a new separation of the development set 1100 into training and test sets is performed and the steps 1120, 1126, 1130 and 1132 are performed on a new random realization of the training set and test set split. The use of multiple training/test splits avoids selection of a single, particularly advantageous or difficult, training set for classifier creation and avoids bias in performance assessment from testing on a test set that could be especially easy or difficult to classify.

We tried two different approaches to splitting over the sample set into training and test sets and repetition of the classifier development steps, depending on the approach used to define the initial groups.

Approach 1. In this approach, the training/test sets split is performed 301 times. A total of 10 samples of each group are randomly assigned, in each realization, to the training set while the remaining samples are used in the test set (8 for the "Low" group and 19 for the "High" group). Each training/test split produces a MC which is applied to the split test set to assess performance.

Approach 2. In this approach, the training/test splits are performed randomly 301 times. A total of 15 samples of each group are assigned, in each realization, to the training set while the remaining samples are used in the test set (31 for the "Low" group and 19 for the "High" group). The performance of each MC is evaluated considering the classification output of the test set.

Step 1137 Analyze Data from the Training/Test Set Splits

At step 1137, the MC performance over all the training and test set splits is performed. This can be done by obtaining performance characteristics of the MCs and their classification results, for example as indicated in block 1138.

Step 1140 Redefine Training Labels

One other advantage of these multiple training/test splits (and reiteration of steps 1120, 1126 and 1130 many times) is that it allows for the refinement of the initial assignment for the "High"/"Low" groups, particularly for those samples which are persistently misclassified. For the training/test splits where a particular sample from the reference group is in the test set, the resulting classifications for the sample can be obtained by the majority vote of the MCs (or by a Modified Majority Vote, MMV, explained below). If the sample persistently misclassifies relative to the initial guess as to the risk group, the sample can be moved from the "High" into the "Low" group, or vice versa, as indicated in loop 1142. Carrying out this procedure for all samples in the development set produces a new, refined version of the risk groups (1102) which is the starting point for a second iteration of the CMC/D classifier development process as indicated by the loop 1142. This refinement process can be iterated so that the risk groups are determined at the same time as a classifier is constructed, in an iterative way.

Approach 3. We Performed Three Successive Iterations of the Loop 1142:

Iteration 1: The labels of the patients for which the classification MMV Label (from approach 2) was mismatching the initial classification group assignment (for 9 patients from the "High" group and 18 patients from the "Low" group) were flipped and a new CMC/D iteration was run. After label flipping, 37 patients were defined as belonging to the "Low" group and 38 to the "High" group. The 301 test/training splits took randomly 15 patients from each group and assigned them to the training set, while leaving the remaining patients in the test set.

Iteration 2: The labels of the patients for which the classification MMV Label was mismatching the classification from Iteration 1 (3 patients from the "High" group and 4 patients from the "Low" group) were flipped and a new CMC/D iteration was run. After label flipping, 36 patients were defined as belonging to the "Low" group and 39 to the "High" group. The 301 test/training splits took randomly 15 patients from each group and assigned them to the training set, while leaving the remaining patients in the test set.

Iteration 3: The labels of the patients for which the classification MMV Label was mismatching the classification from Iteration 2 (1 patient from the "High" group and 2 patients from the "Low" group) were flipped and a new CMC/D iteration was run. After label flipping, 35 patients were defined as belonging to the "Low" group and 40 to the "High" group. The 301 test/training splits took randomly 15 patients from each group and assigned them to the training set, while leaving the remaining patients in the test set.

Step 1144 Define Final Test/Classifier

At step 1144, a final classifier is defined from one or more of the master classifiers (MCs) generated in the previous iterations of the process. There are several possibilities for defining the final classifier, including by selection of one master classifier which has typical performance, by majority vote of all master classifier from each realization of the sample set into training and test sets, by modified majority vote, or other. In this example, the final classifier is created from 301 MCs (301 different realizations of the training/test set split) by taking a majority vote over the MCs.

Modified Majority Vote (MMV)

Within the CMC/D process, each training/test split realization produces one master classifier (MC) generated from the combination of mini-classifiers (mCs) through logistic regression with dropout regularization. The output of this logistic regression is, in the first instance, not a binary label but a continuous probability taking values between 0 and 1. Applying a cutoff (e.g. 0.5, but any choice is possible) to these MC probabilities, we can turn them from a continuous variable into a binary label. So, each MC produces a classification label for a given sample. However, this step is not essential, and one can choose not to apply a cutoff here, but instead to retain the information in the continuous probability variable.

Having obtained the outputs from the MCs (either in terms of binary labels via use of a cutoff or in terms of probabilities), these need to be combined ("bagged" in learning theory language) across the MCs to produce a single binary classification for a particular sample. The way the CMC/D process is implemented means that when a sample is used in the training set of the MC for a realization, the sample almost always classifies correctly (in terms of binary labels after implementation of a cutoff or in terms of probabilities close to target of 0 for one class and 1 for the other class). Hence, use of a simple majority vote over all MCs can produce an artificially good assessment of classifier performance for samples that are used in the training set for some of the MCs. To avoid this, we can use a modified majority vote (MMV) to obtain a classification for samples used directly in the development of the classifier. This procedure is a majority vote over the MC outputs only when the sample is not included in the training set of the MC. (For samples never used in training the MCs, the majority vote and MMV are the same.) This MMV can be used after implementation of a cutoff by taking a majority vote of the classifications produced by all MCs for which the sample is not included in the training set. If, instead, we want to avoid the use of a cutoff at this point and work with the MC probability outputs, the average of the probabilities across the MCs for which the sample is not included in the training set can be calculated. Taking the latter approach, the MMV produces another, averaged, continuous variable that can take values between 0 and 1, an average probability of being in a particular class. This can be converted into a binary classification label via implementation of a cutoff after averaging over MCs.

Direct averaging of the probabilities provides some advantages. If we obtain an average probability for each sample, it is possible to assess simultaneously the performance of the whole family of classifiers that can be produced by imposing different cutoffs on the average probability. This can be done by using the standard receiver operating characteristic (ROC) curve approach, a well-known method. For a particular choice of cutoff on the average probabilities, classification labels are generated for all samples and these labels can be compared with the known or initially defined class labels to calculate the sensitivity and specificity of the classifier defined by this cutoff. This can be carried out for many values of the cutoff and the results plotted in terms of sensitivity versus 1-specificity (the ROC curve). Overall performance of the family of classifiers can be characterized by the area under the curve (AUC). The ROC curve can be inspected and a particular cutoff selected that best suits the target performance desired for the classifier, in terms of sensitivity and specificity.

Results for Example 1

Approach 1 (no label flips). The resulting CMC/D classifier obtained using the group definitions of this approach achieves a performance described by the following metrics, obtained by comparing the classification label with the defined label only when a given sample is in the test set (Modified Majority Vote, MMV).

| Accuracy | Sensitivity (Positive = "High") | Specificity (Negative = "Low) |
|---|---|---|
| 0.65 | 0.69 | 0.61 |

The distribution of each of these metrics across the 301 MCs created is shown in FIG. 2. All the metrics are centered between 60 and 70%, indicating some performance of the classifiers and some hint that, with better MALDI spectra or a new sample set incorporating more detailed clinical data, a reasonable test might be created.

Regarding the patients assigned to the "Int" group, 10 of them (36%) are classified as belonging to the "High" group and 18 of them (64%) to group "Low". This shows a tendency for the intermediate risk patients to be classified as low risk, which justifies the reference set arrangement chosen in approach 2.

Approach 2 (no label flips). The resulting CMC/D classifier obtained achieves a performance described by the following metrics, obtained through MMV.

| Accuracy | Sensitivity (Positive = "High") | Specificity (Negative = "Low) |
|---|---|---|
| 0.64 | 0.68 | 0.61 |

Figure 3B:
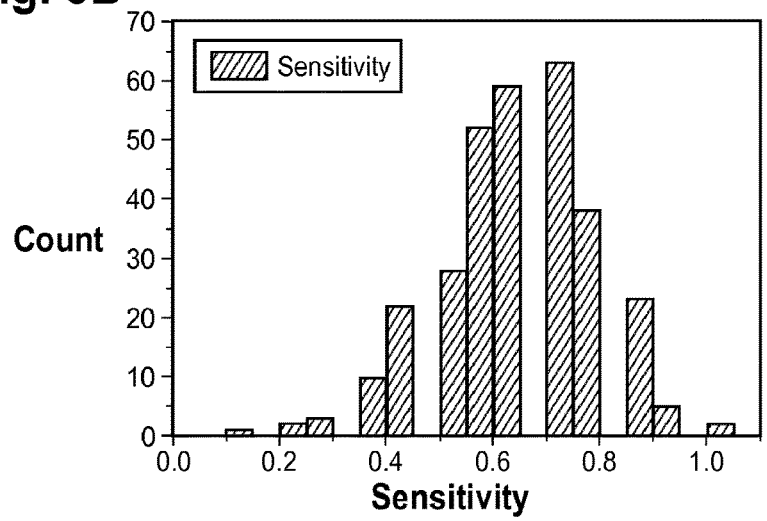
Figure 3C:
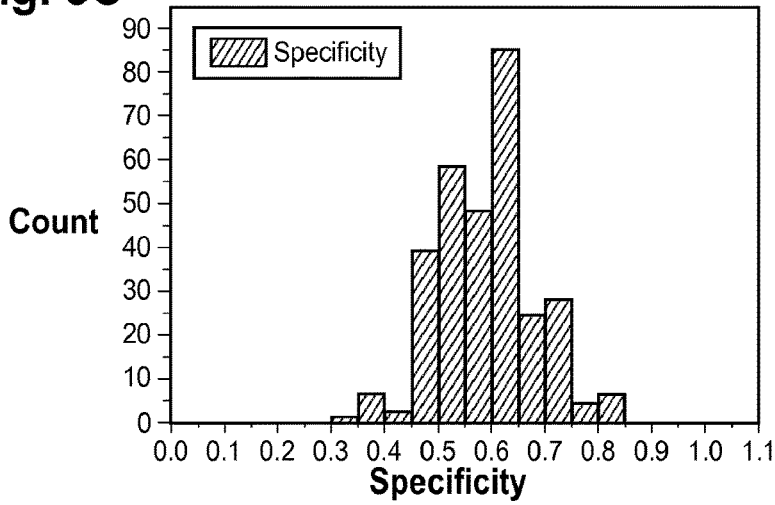
Figures 4A, 4B, 4C:
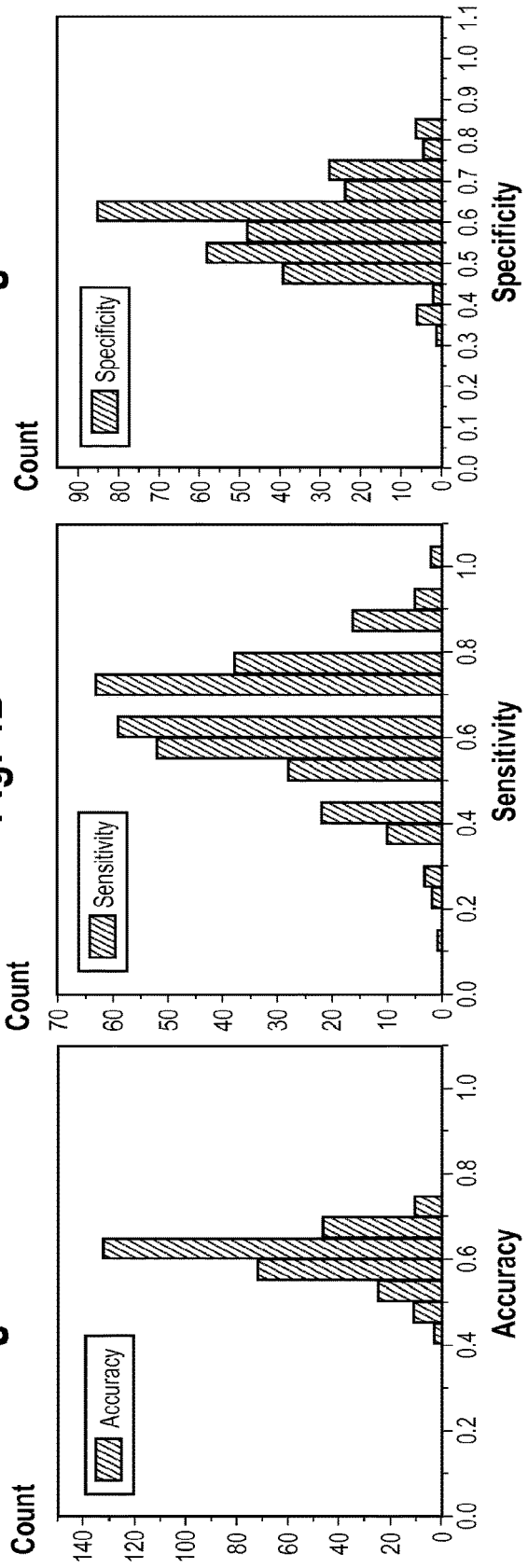
FIGS. 4A-4L are plots of the distribution of the performance metrics among the obtained MCs for approach 2 of Example 1 when flipping labels. Each row of plots corresponds to a sequential iteration of loop 1142 in the classification development process of FIG. 1.
Figures 4D, 4E, 4F:
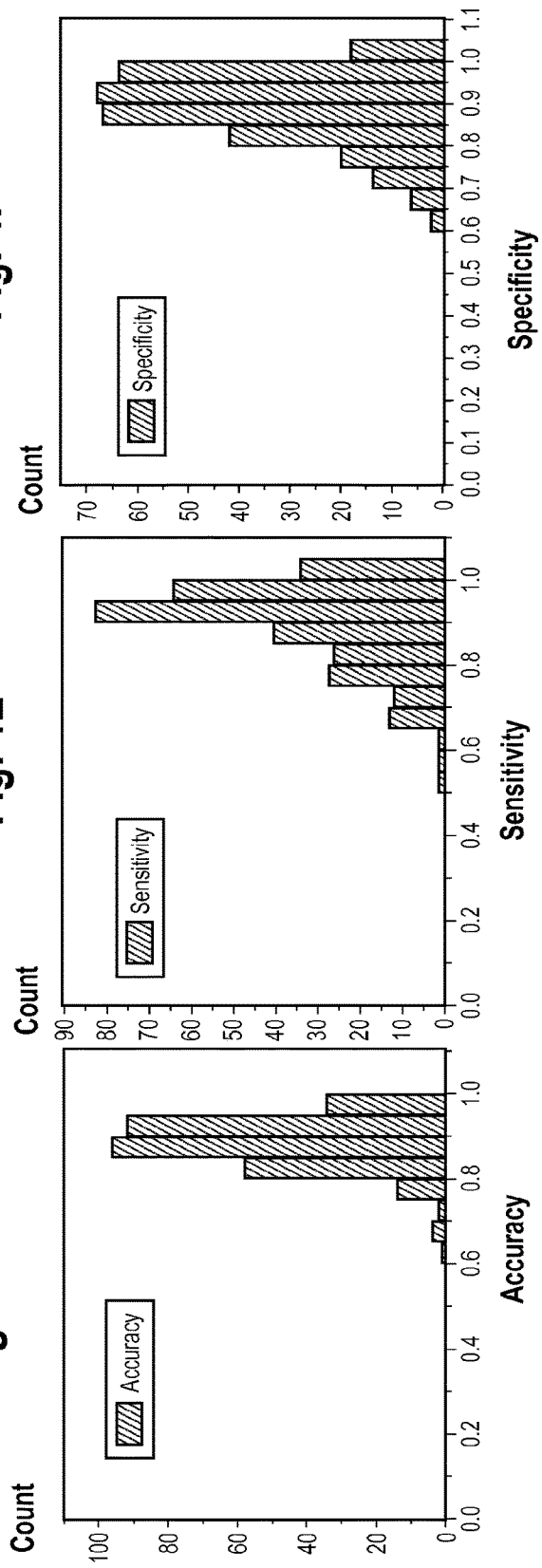
Figures 4G, 4H, 4I:
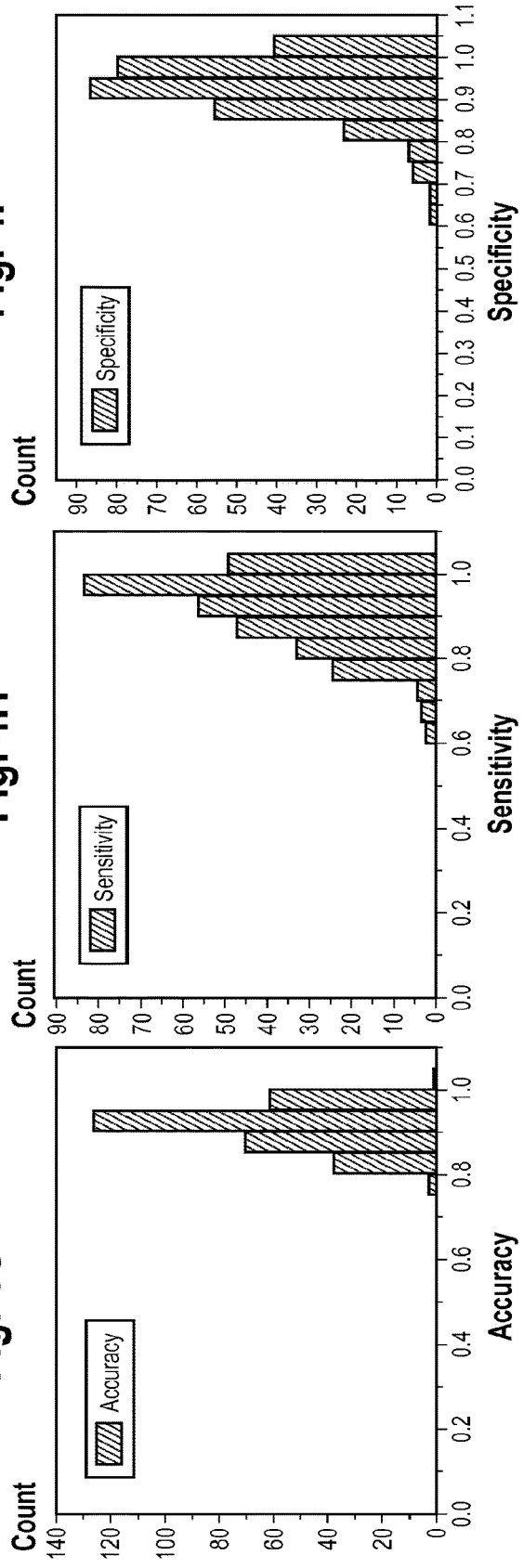
Figures 4J, 4K, 4L:
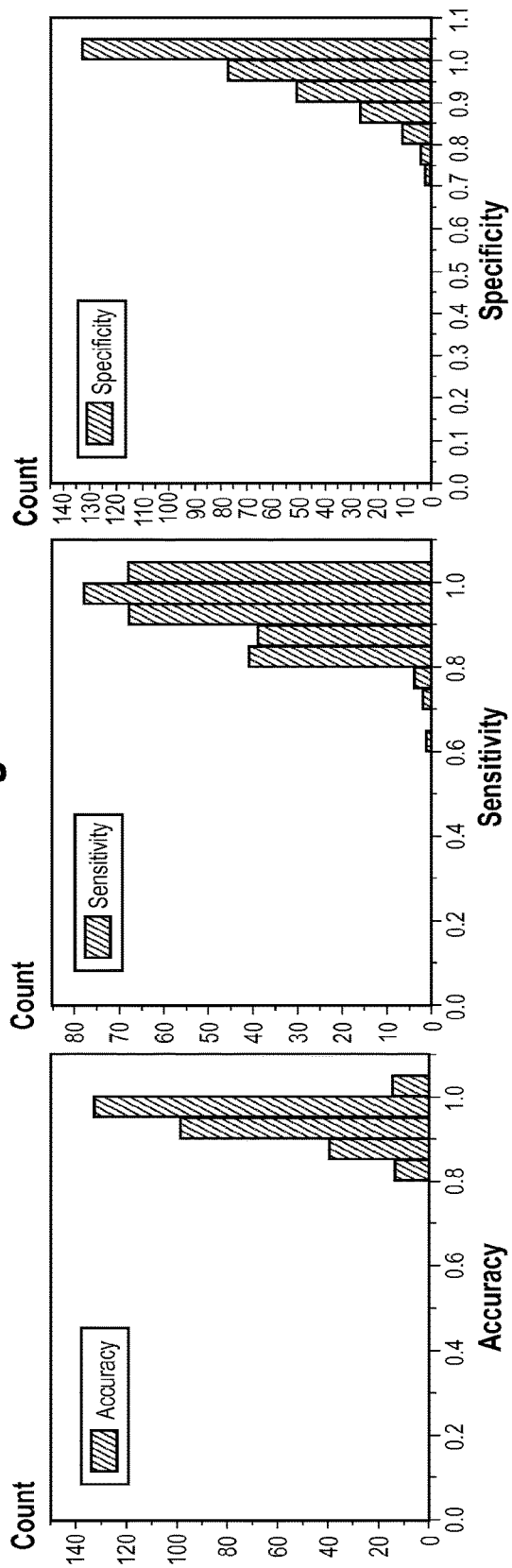

The distributions of each of these metrics across the created 301 MCs are shown in FIG. 3. The average performance is similar to that of approach 1 although the accuracy and specificity distributions seem to be narrower. One hypothesis for this behavior might be the larger training sets (15 patients for each group instead of 10).

Approach 3 (with label flips). The resulting CMC/D classifiers, created in each iteration of the labels flips are described by the following average metrics (obtained through MMV):

| Iteration | Accuracy | Sensitivity (Positive = "High") | Specificity (Negative = "Low") |
|---|---|---|---|
| 0 | 0.64 | 0.68 | 0.61 |
| 1 | 0.91 | 0.92 | 0.89 |
| 2 | 0.96 | 0.97 | 0.94 |
| 3 | 0.99 | 0.98 | 1 |

It should be noted that the metrics, after iteration 0, do not correspond to accuracy relative to the initial group definitions, due to the label flips. The distributions of these metrics for all the 301 MCs are shown in FIG. 4.

After 3 iterations of labels flips, we tried to correlate the final classification labels with the only available clinical data: the Gleason Score. Table 6 summarizes the distribution of the final labels among the different Primary+Secondary Gleason Scores combinations and Table 7 shows the frequency distributions of the final labels versus the initial guess based on TGS. The individual MMV classification labels, obtained after 3 iterations, are shown in the table of Example 1 Appendix C for all the patients.

TABLE 6

Distribution of the classification labels, obtained after 3 iterations of label flips, according to the different Primary + Secondary Gleason Scores combinations

| Risk | Primary + Secondary GS | Total GS | #Patients | #HighClassifications | #LowClassifications |
|---|---|---|---|---|---|
| Low | 3 + 3 | 6 | 18 | 8 | 10 |
| Int | 3 + 4 | 7 | 20 | 8 | 12 |
|  | 4 + 3 | 7 | 8 | 4 | 4 |
| High | 3 + 5 | 8 | 1 | 1 | 0 |
|  | 4 + 4 | 8 | 13 | 10 | 3 |
|  | 5 + 3 | 8 | 2 | 1 | 1 |
|  | 4 + 5 | 9 | 11 | 7 | 4 |
|  | 5 + 4 | 9 | 1 | 0 | 1 |
|  | 5 + 5 | 10 | 1 | 0 | 1 |
|  | Totals |  | 75 | 39 | 36 |

TABLE 7

Contingency table showing the frequency distribution according to the initial assignment and the final classification labels achieved after 3 iterations of label flipping.

|  |  | Final Label | |
|---|---|---|---|
|  |  | High | Low |
| Initial group | High | 19 | 10 |
| definition | Low/Int | 20 | 26 |

By applying a Fisher's exact statistical test to the numbers of Table 7, we get a 9.6% probability of getting these results or results with stronger correlation between classification labels and those based on TGS assuming that the final classification labels "High" and "Low" are not correlated with TGS risk groups. This p-value is small enough to believe that the final labels may be meaningful and still are somehow related to the TGS distribution and our initial guess for the indolence or aggressiveness (Low, High) labels.

t-SNE Visualization t-Distributed Stochastic Neighbor Embedding (t-SNE) is a tool that allows the visualization of high-dimensional data in a 2D or 3D-map, capturing much of the local structure of the data while also revealing global structure (e.g., the presence of clusters at several scales). The method converts high-dimensional Euclidean distances between data points into Gaussian similarities. In the low-dimensional (2D or 3D) space, the same process is applied using a Student-t distribution instead of a Gaussian distribution to compute the similarity between pairs of points. Then, iteratively, the method searches for a low-dimensional representation of the original data set that minimizes the mismatch between the similarities computed in the high- and low-dimensional spaces. In this way, a 2D or a 3D point map is constructed that allows the visualization and identification of structure in a given dataset and may possibly guide research. The method is introduced by the paper of L. J. P. van der Maaten and G. E. Hinton, *Visualizing High-Dimensional Data Using t-SNE*, Journal of Machine Learning Research 9 (November): 2579-2605 (2008), the content of which is incorporated by reference herein.

Figure 5A:
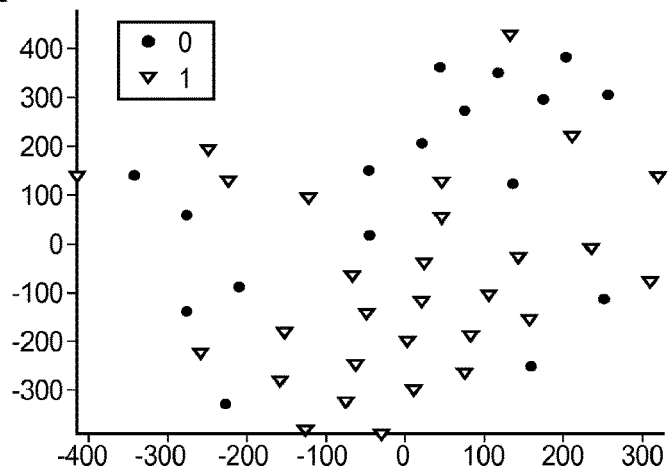
FIGS. 5A-5C are t-Distributed Stochastic Neighbor Embedding (t-SNE) 2D maps of the development sample set labeled according to the initial assignment of group labels for the development sample set in Approach 1 of Example (FIG. 5A); an initial assignment for Approach 2 of Example (FIG. 5B); and final classification labels after 3 iterations of label flips (Approach 3 of Example 1)(FIG. 5C). "1" (triangles) corresponds to "High" and "0" (circles) to "Low" group label assignments.
Figure 5B:
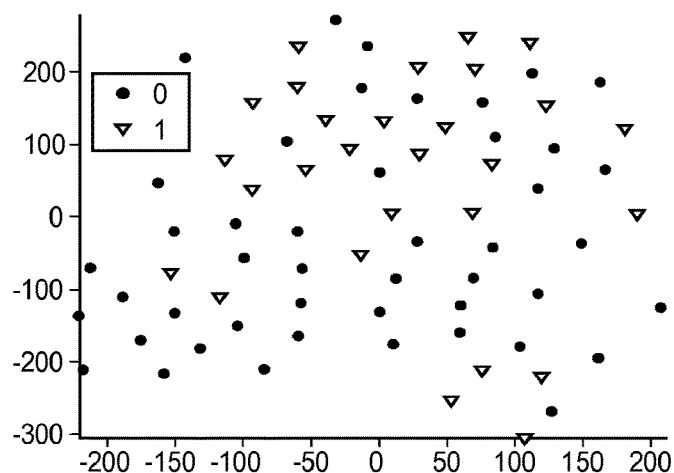
Figure 5C:
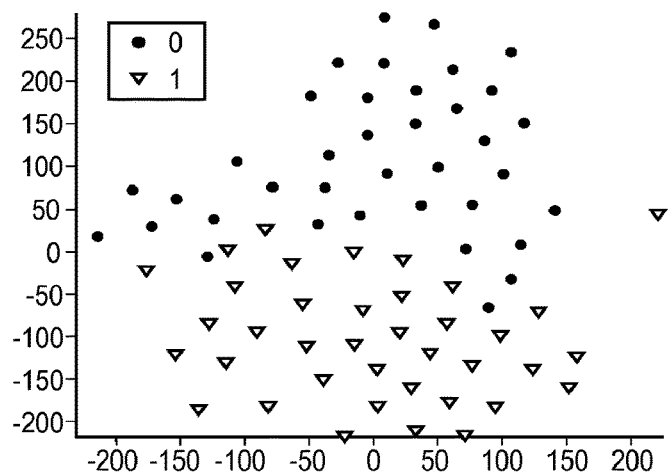

In FIG. 5A-5C, the 2D maps of the data obtained through t-SNE are shown for 3 different situations: the initial group definitions for approaches 1 and 2 (no label flips), and the final classification labels after 3 iterations of label flips (approach 2 with label flips). Each point is represented with a marker that identifies to which risk label it was assigned ("1" corresponds to "High" and "0" to "Low"). In FIG. 5A-5C, the data points are labeled according to the initial group assignments based on TGS for approach 1 (FIG. 5A); initial assignment for approach 2 (FIG. 5B); final classification labels after 3 iterations of label flips (approach 3) (FIG. 5C). "1" (triangles) corresponds to "High" and "0" (circles) to "Low".

Example 1 Conclusions

By using MALDI-TOF mass spectra obtained from serum samples from 75 patients for whom Gleason Scores were available, it was possible to create CMC/D binary classifiers that assigned a "High" or a "Low" risk label to each patient and were described by accuracies, sensitivities and specificities of 60-70%, when using Modified Majority Votes taken from 301 Master Classifiers. Two different approaches, differing in the initial group definitions were tried achieving very similar performances. The distributions of the performance metrics of the 301 Master Classifiers are, for both approaches, peaked at the previously mentioned averages, not showing unreasonable shapes. Although the accuracies do not seem to be great, the only available clinical variable (the TGS) is also not a perfect method of risk assessment, and it might be that a study including more clinical data that allows the assessment of outcomes might reveal better performances. Better quality mass spectra, from which more features may be extracted, would also represent a good addition to any new data set.

Starting with the output of approach 2, we have also tried to iteratively flip the initial classification group assignment in order to achieve better performance based on the accuracy metrics (>95%). The final labels seem to be statistically significantly correlated with risk as assessed by Gleason score (at the 10% confidence level), deserving further investigation, in which additional clinical data would help. Hence, we obtained a second set of data (Arizona data set) and applied the process of generating a classifier to this new data set which will be described below in Example 2.

Note that in the procedure of FIG. 1 there is step 1146 of validation of the test defined at step 1144 on an internal validation set if available, and a step 1148 of validation of the test on an independent sample set. In the work described in Example 1 we had no internal validation set since the sample size was small and step 1146 was not performed. We could have used the samples described below in Example 2 as a validation set to perform step 1148, however they were plasma and not serum samples, and it was not known whether the classifier would transfer across sample type. So, instead we decided in Example 2 to repeat the classifier generation process of FIG. 1.

Example 2: Arizona Data Set

This example involves the analysis of MALDI-TOF mass spectra obtained from plasma samples from patients diagnosed with prostate cancer. All the patients that comprise the data set had their Total Gleason Score (TGS) evaluated as being lower than 8. This range of TGS is considered to be associated with low progression risk and thus these patients are not treated immediately, but instead put in watchful waiting.

The aim of the work described in this Example was to develop a classifier capable of evaluating the aggressiveness or indolence of the prostate cancer of a patient put in watchful waiting (TGS<8). During the clinical study the patients had periodic physician visits (quarterly), having blood samples drawn and their disease status assessed. Evidence of progression could be based on the rate of rise in PSA, Chromogramin A or alkaline phosphatase. Progression could also be detected based on a degradation of patient's symptoms. In case of progression, the patient followed a treatment plan and was dropped from the study. A classifier that could be run at the moment of the cancer diagnosis and could give a good prognostic indication would be a valuable addition to the monitoring of PSA level or other biomarkers as an aid to more refined treatment guidance for this group of patients following diagnosis.

Although the clinical data does not include a precise record of the Time to Progression (TTP) of the patients, we have records of the dates when the patients had their physician visits and their PSA levels assessed. This allows us to make a crude estimation of the TTP by considering it to be the time difference between the last recorded patient visit and the date of entry into the study.

Available Samples

The dataset used in this classifier feasibility assessment was obtained from another study that investigated the ability of Selenium (Se) to delay the progression of prostate cancer after diagnosis. Patients were randomized into three groups which received placebo or two different doses of Se supplementation. It turned out that Se did not show a protective effect, and thus we assume that the dataset can be used without taking into consideration the supplementation doses given to each patient.

A total of 441 mass spectra acquired from plasma samples of prostate cancer patients were available, corresponding to 147 patients (3 replicates per patient). The spectra of 10 patients (Patient IDs: WW000059, WW000062, WW000068, WW000070, WW000073, WW000074, WW000076, WW000079, WW001835 and WW040568) were not used in the study because there was no clinical/outcome data available for them.

The remaining 137 patients, with valid data for the study, were distributed according to the progression outcome and TGS presented in Table 8.

TABLE 8

Distribution of the patients according to their outcome and TGS

| Outcome | TGS | #Patients | Sub totals |
| --- | --- | --- | --- |
| Left the study after randomization (code = 8) | Unknown | 2 | 92 |
| | 3 | 2 | |
| | 4 | 3 | |
| | 5 | 14 | |
| | 6 | 58 | |
| | 7 | 13 | |
| Completed the study (5 years) without progressing (code = 90) | Unknown | 0 | 22 |
| | 3 | 0 | |
| | 4 | 5 | |
| | 5 | 5 | |
| | 6 | 12 | |
| | 7 | 0 | |
| Progressed (code = 99) | Unknown | 1 | 23 |
| | 3 | 2 | |
| | 4 | 0 | |
| | 5 | 1 | |
| | 6 | 17 | |
| | 7 | 2 | |
| | | Total | 137 |

Note: Patients WW001545, WW001636 and WW040733 did not have their TGS available, but were still included in study, because the construction of the classifier is based on the progression outcome data and not on TGS.

Spectral Acquisition

Sample Preparation

Samples were thawed on ice and spun at 1500 g for 5 minutes at 4° C. Each sample was diluted 1:10 with water and then mixed 1:1 with sinapinic acid (25 mg/ml in 50% ACN/0.1% TFA). The samples were spotted in triplicate.

Acquisition of Mass Spectra

Spectra of nominal 2,000 shots were collected on a MALDI-TOF mass spectrometer.

Spectral Pre-Processing

Averaging of Spectra to Produce One Spectrum Per Sample

For each of the 3 replicate spectra available for each patient, the background was estimated and subtracted. Peaks passing a SNR threshold of 6 were identified. The raw spectra (no background subtraction) were aligned using a subset of 15 peaks (Table 2 above) to correct for slight differences in m/z scale between replicate spectra. The aligned spectra were averaged resulting in a single average spectrum for each patient. With the exception of alignment, no other preprocessing was performed on the spectra prior to averaging.

Feature Definitions for New Classifier Development Using all Valid Samples

The averaged spectra from the patients that either progressed during the study or completed the study without progression were background subtracted using the same parameters as in the previous step. They were then initially normalized using PIC with the normalization windows shown in Table 3. Such windows were defined to avoid the peaks due to the known contaminant at m/z~4138-4205 Da, the hemoglobin peaks, the peaks used in applicants' VeriStrat test noted in U.S. Pat. No. 7,736,905, and everything with poor reproducibility above m/z=23000 Da. A total of 104 features were identified by overlaying the spectral sample averages and assessing the spread of the band from the overlay to define the left and right boundaries. Oxidation states were combined into single features when seen. The feature definitions are given in Example 2 Appendix A. Further details on partial ion current normalization of mass spectral data are known in the art and therefore omitted for the sake of brevity, see U.S. Pat. No. 7,736,905 for further details.

Normalization of the Averaged Spectra

Using these specified feature definitions, a feature table for non-normalized spectra (just background subtracted) was constructed for all the 137 patients. The feature values were normalized using partial ion current (PIC) based on the ranges of the features listed in Table 9.

TABLE 9

Features used in the final PIC normalization.
For further details on the feature ranges see Example 2 Appendix A.
Feature

| |
| --- |
| 6838 |
| 6859 |
| 6882 |
| 6941 |
| 13795 |
| 13840 |
| 13878 |
| 13915 |
| 13979 |
| 14157 |

Using this optimized PIC normalization, a new feature table was constructed for all the patients and used downstream in the classifier development process (FIG. 1).

Classifier Development Process

Basically, the classifier development process of FIG. 1 and described in detail above was used for generation of a new CMC/D classifier using the Arizona data set.

Division of Samples into Development and Validation Sets

Figure 6:
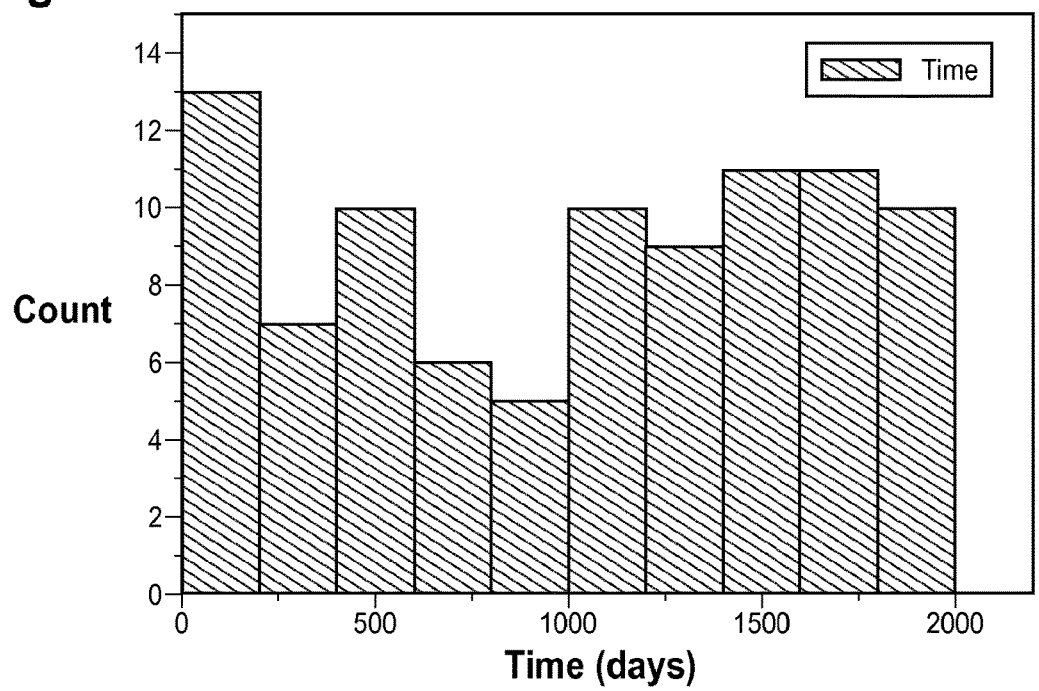
FIG. 6 is a plot of the distribution of the times on study for patients in Example 2 leaving the study early without a progression event.

After randomization, patients could leave the study by withdrawal of consent. In addition, Se levels in the blood were monitored regularly during the study and, if three (not necessarily consecutive) Se blood levels above 1,000 ng/ml were measured for a given patient, he was dropped from the study. Although dropped from the study without progression, these patients give us additional information, as we do know that they did not progress while on the study. The distribution of the time on study of this subset of patients is shown in FIG. 6. We split this set of samples (from patients leaving the study without progression) into two halves, one of which was added to the other samples (from patients completing the study or progressing during the study) to make the development set (1100, FIG. 1) and the second half was used as a partial "validation set" (step 1146 of FIG. 1). Note that this "validation" set does not contain any patients with progression during the study, so it will be of limited utility in classifier validation. The splitting of these patients leaving the study without progression into two subsets was made randomly, but stratified to ensure a nearly balanced number of patients with similar TGS and time on study in both sets.

Definition of Initial Classifier Reference Set Groups (Step 1102)

Figure 13:
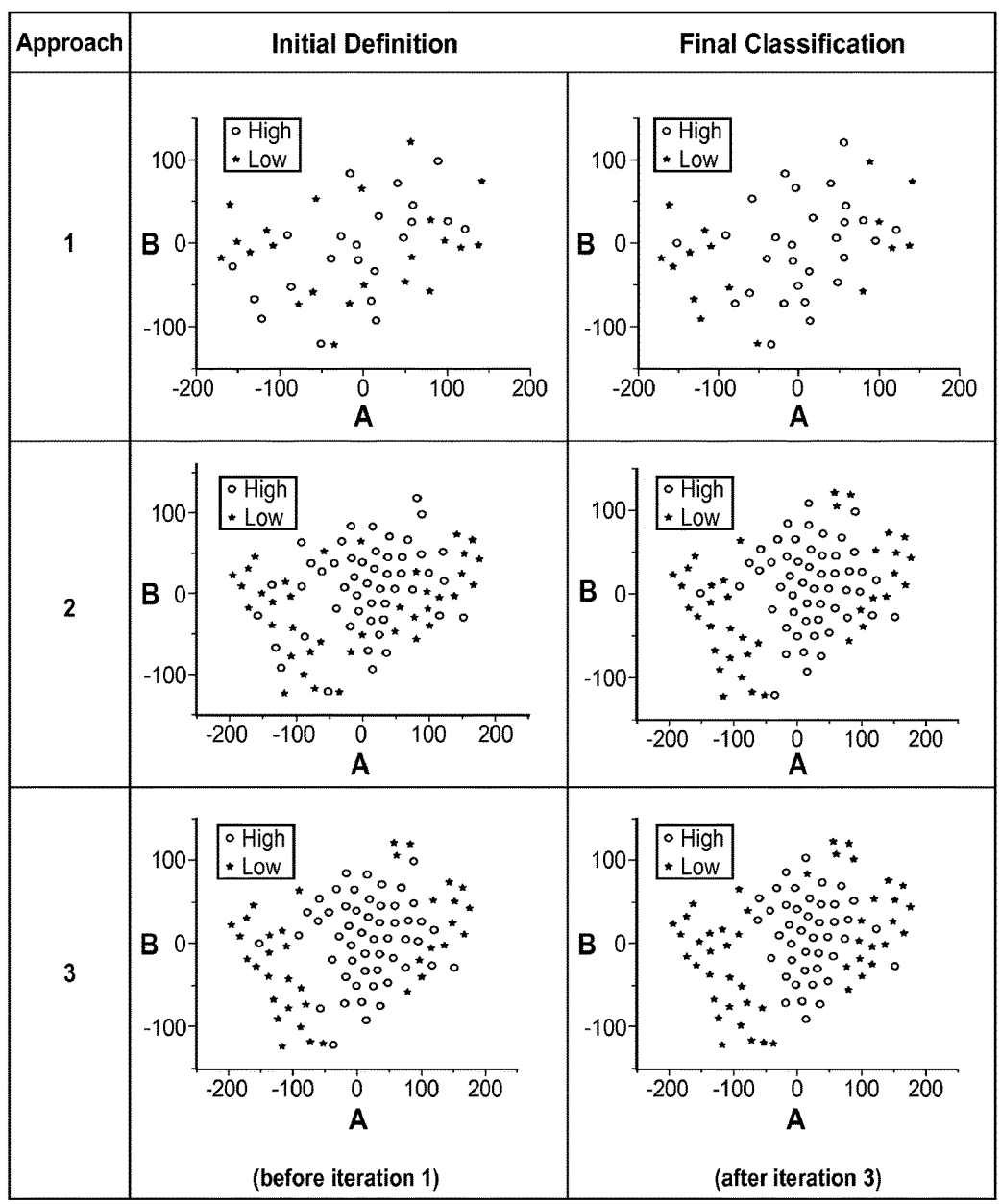
FIG. 13 are t-Distributed Stochastic Neighbor Embedding (t-SNE) two dimensional maps of the classifier development data set, labeled according to (left) the initial assignment for the group labels in the training set and (right) the final classification labels, for each of three approaches to classifier development used in Example 2.

We tried to develop a classifier for assessing the aggressiveness or indolence of a patient's cancer and used the inferred progression outcome data for its performance assessment. With this in mind we tried a few different approaches. For each approach, a plot of the 2D mapped space, obtained using t-SNE, is shown in FIG. 13 together with the labels shown for the initial development set assignments and for the final classification labels.

Approach 1. We used the samples from patients completing the study without progression (22 patients) and the samples from patients progressing during the study (23 patients) to construct a final (binary) CMC/D classifier that would distinguish between "High" and "Low" risk of cancer progression within 5 years. Patients without progression during the 5 years of the trial were assigned to the "Low" risk reference group and patients who progressed on the study to the "High" risk. The patients who dropped out of the study without progression were left aside and later evaluated with the CMC/D classifier resulting from this approach. This arrangement would presumably give the clearest separation in terms of progression risk, because we leave aside the patients that dropped out of the study (and for whom we do not really know what happened).

Approach 2. We included half of the patients who dropped out of the study without progression in the test/training splits, by considering the label assigned by the classifier developed in Approach 1 as the initial guess for their risk group.

Approach 3. We tried an iterative label flip process (loop 1142), starting with the group definitions of Approach 2 in order to verify if such method would lead to improved discrimination in terms of outcome data (i.e., better Hazard Ratio for time to progression between High and Low risk groups).

Once the initial definition of the groups for the mini-classifiers has been established, the development set 1100 is split into training (1112) and test sets (1110).

Creation and Filtering of Mini-Classifiers (Steps 1120 and 1126)

Many k-nearest neighbor (kNN) mini-classifiers (mCs) that use the training set as their reference set are constructed using single features or pairs of features from the 104 mass spectral features identified. This corresponds to a total of 5,460 possible mCs. The parameters used to traverse the space of mCs for this project are listed in Table 12.

TABLE 12

| Parameters used to create mCs | |
| --- | --- |
| kNN parameters | |
| k | 5 |
| mC traversal parameters | |
| Max number of features | 2 |

To target a final classifier that has optimal performance characteristics, these mCs were filtered. Each mC was applied to its training set and the Hazard Ratio (HR) was calculated using the resulting classifications. Only mCs that satisfied thresholds in terms of HR (Table 11) passed filtering and were used further in the process.

TABLE 11

| Summary of mC filtering options used | |
| --- | --- |
| Filtering Criteria | Filtering Parameters |
| Hazard Ratio | 3.0 < HR < 10.0 |

Generation of MC by Combination of Mini-Classifiers Using Logistic Regression with Dropout (CMC/D) (Steps 1130, 1132)

Once the filtering of the mCs is complete, the mCs are combined in one master classifier (MC) using a logistic regression trained with the training set labels. To help avoid over-fitting, the regression is regularized using extreme drop out. A total of 5 randomly selected mCs are included in each logistic regression iteration and the weights for the mCs averaged over 10,000 dropout iterations.

Training/Test Splits and Analysis of Master Classifier Performance (Step 1136)

The use of multiple training/test splits in loop 1136 avoids selection of a single, particularly advantageous or difficult, training set for classifier creation and avoids bias in performance assessment from testing on a test set that could be especially easy or difficult to classify. Accordingly, loop 1136 was taken 301 times in Example 2, resulting in 301 different master classifiers (MCs), one per loop. A final classifier is defined at step 1144 from the 301 MCs by taking a majority vote over the MCs. For each approach above this process is described in more detail:

Approach 1. A total of 12 samples from the "High" group and 11 samples from the "Low" group are randomly assigned, in each realization, to the training set while the remaining samples are used in the test set (11 for each of the groups). Each training/test split produces a MC which is applied to the test set at step 1134. At step 1134, the Hazard Ratio is assessed taking into consideration the risk groups defined by the Modified Majority Vote (MMV) classifications.

Approach 2. When the process loops back to step 1108, and samples from patients leaving the study without progression are fed into the development set with risk labels guessed from the results of approach 1, a total of 21 samples from the "High" group and 20 samples from the "Low" group are randomly assigned, in each realization, to the training set 1112 while 30 from the "High" group and 20 for the "Low" are designated as members of the test set 1110 and used for testing at step 1134. The Hazard Ratio is then assessed considering the MMV labels.

Approach 3. At step 1140, one other advantage of these multiple training/test splits is that it might allow for the refinement of the initial assignment of High and Low group labels for the development set at step 1102. In particular, for the training/test splits where a particular sample from the development set is in the test set, the MMV label is obtained. If the sample persistently misclassifies relative to the initial guess as to the risk group, the sample can be moved from the "High" into the "Low" group, or vice versa. Carrying out this procedure for all samples in the development set produces a new, possibly refined version of the group label definitions (1102) which are the starting point for a second iteration of the CMC/D process. This refinement process can be iterated so that the risk groups are determined at the same time as a classifier is constructed, in an iterative way.

In Our Development of the CMC/D Classifier, we Performed Three Different Iterations of Loop 1142 after the Initial Iteration (Iteration 0):

Iteration 1: The labels of the patients for which the classification MMV Label (from approach 2) was mismatching the initial guess (9 patients from the "High" group and 11 patients from the "Low" group) were flipped and a new CMC/D iteration (steps 1102, 1108, 1120, 1126, 1130, 1134, 1136) was run. After this label flipping, 53 patients were classified as belonging to the "High" group and 38 to the "Low" group. The 301 test/training splits randomly took 18 patients from the "High" group and 19 from the "Low" group to the training set, while leaving the remaining patients in the test set.

Iteration 2: The labels of 6 patients from the "High" group and 1 patient from the "Low" group, whose MMV label didn't match the initial guess were flipped and a new CMC/D iteration was run. After label flipping, 48 patients were classified as belonging to the "High" group and 43 to the "Low" group. The 301 test/training splits randomly took 24 patients from the "High" group and 22 from the "Low" to the training set, while leaving the remaining patients in the test set.

Iteration 3: The labels of 5 patients from the "High" group and 1 patient from the "Low" group were flipped and a new CMC/D iteration was run. After label flipping, 44 patients were classified as belonging to the "High" group and 47 to the "Low" group. The 301 test/training splits randomly took 22 patients from the "High" group and 24 from the "Low" group to the training set, while leaving the remaining patients in the test set.

Results (Example 2)

Figure 7:
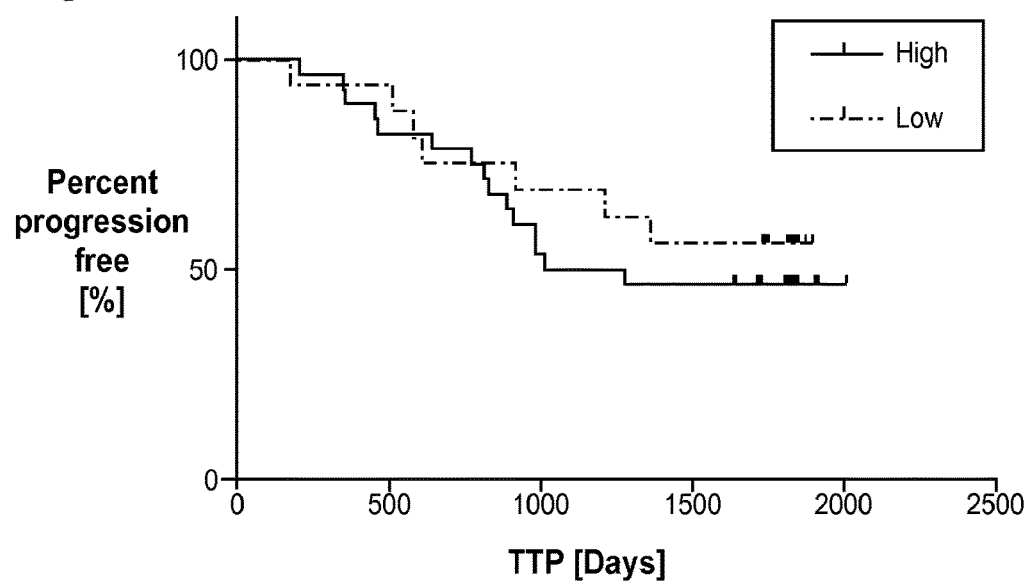
FIG. 7 is a plot of Kaplan-Meier curves for time to progression (TTP) using the modified majority vote (MMV) classification labels obtained by a final classifier in Approach 1 of Example 2.

Approach 1. The final CMC/D classifier, defined at step 1144 as a MMV over all the 301 master classifiers using "Approach 1" above, is characterized in terms of patient outcome by the Kaplan-Meier survival curve shown in FIG. 7. The curve is obtained by comparing the groups defined by the samples that were classified with "High" or "Low" MMV labels and the associated time to progression (TTP) from the clinical data associated with the development sample set 1100. The final CMC/D classifier does not seem to be able to distinguish between patients who progressed early and those who progressed later, with the Kaplan-Meier curves for TTP being similar for both groups. The log-rank test gives a p-value of 0.51 and the log-rank Hazard Ratio (HR) is 1.34 with a 95% Confidence Interval (CI) of 0.56-3.14. The accuracy metrics of this classifier do not show any particularly interesting performance.

| Accuracy | Sensitivity (Positive = "High") | Specificity (Negative = "Low") |
| --- | --- | --- |
| 0.56 | 0.68 | 0.41 |

While the CMC/D classifier seems to give a sensitivity better than a coin-flip, it seems to do poorly with the "Low" risk patients, misidentifying more than half of them as "High" risk (low specificity).

Regarding the patients left out of the training/test sets (those who left the study without progression), 25 were classified with the label "High" and 21 with the label "Low". FIG. 8 is a plot of the Kaplan-Meier curves for TTP for the classifications obtained in Approach 1, including half (46) of the patients who dropped out of the study. For the patients who were used in the test/training splits, the MMV label is taken. For those patients who dropped out of the study (code "8"), the normal Majority Vote of all the 301 MCs is used. Log-rank test p-value=0.42, log-rank HR=1.42 with a 95% CI=[0.61-3.33].

Figure 10:
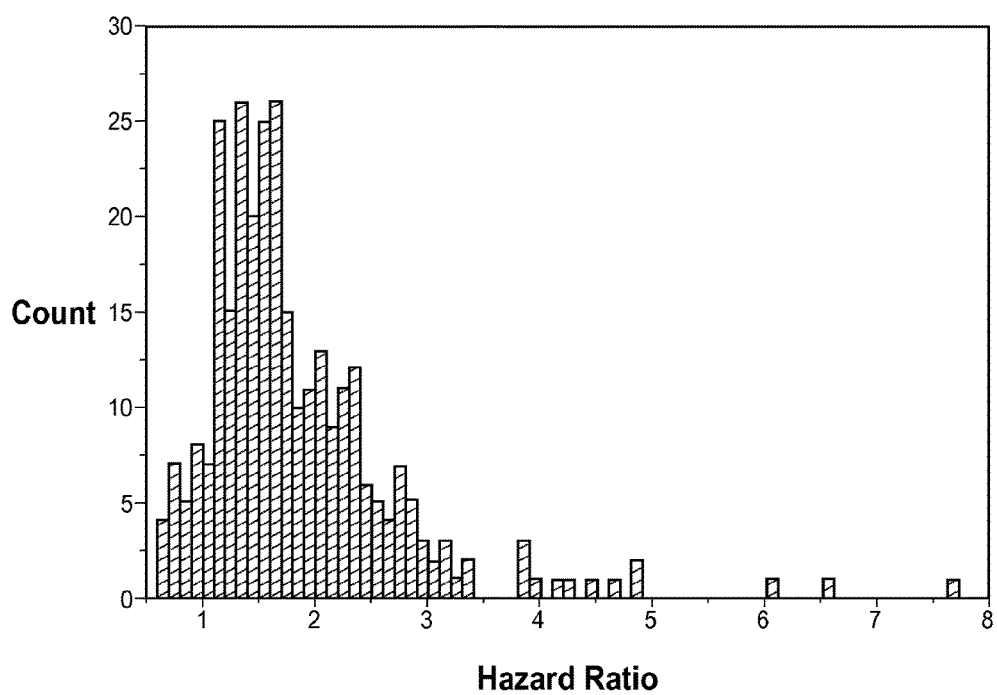
FIG. 10 is a plot of the distribution of Cox Hazard Ratios of the individual 301 master classifiers (MCs) created in Approach 2 of Example 2.

Approach 2. The final CMC/D classifier obtained for "approach 2" is characterized by the Kaplan-Meier curves shown in FIG. 9. The log-rank test gives a p-value of 0.037 and the log-rank Hazard Ratio (HR) is 2.74 with a 95% Confidence Interval (CI) of 1.05-5.49. The distribution of the HRs of the 301 MCs is shown in FIG. 10 and shows a "well behaved" shape, with a very small fraction of the MCs having a HR ratio lower than 1. The percent progression free for each classified risk group at 3, 4 and 5 years after study entry is shown in the following table 12:

TABLE 12

| Time on study [years] | Percent Progression Free [%] | |
|---|---|---|
| | High | Low |
| 3 | 63.9 | 87.3 |
| 4 | 58.8 | 82.9 |
| 5 | 58.8 | 82.9 |

The accuracy metrics (using the MMV labels) are also quite promising in this approach:

| Accuracy | Sensitivity (Positive = "High") | Specificity (Negative = "Low") |
|---|---|---|
| 0.78 | 0.82 | 0.73 |

Figure 11A:
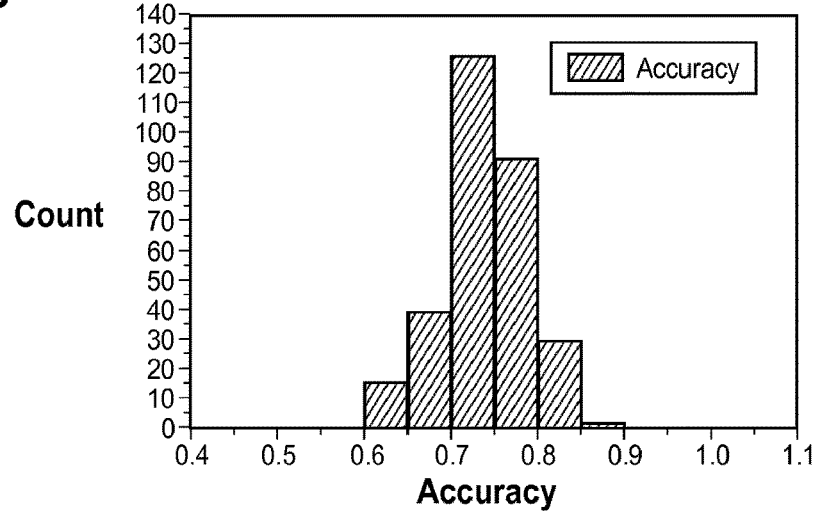
FIGS. 11A-11C are plots of the distribution of the performance metrics among the MCs in Approach 2 of Example 2.
Figure 11B:
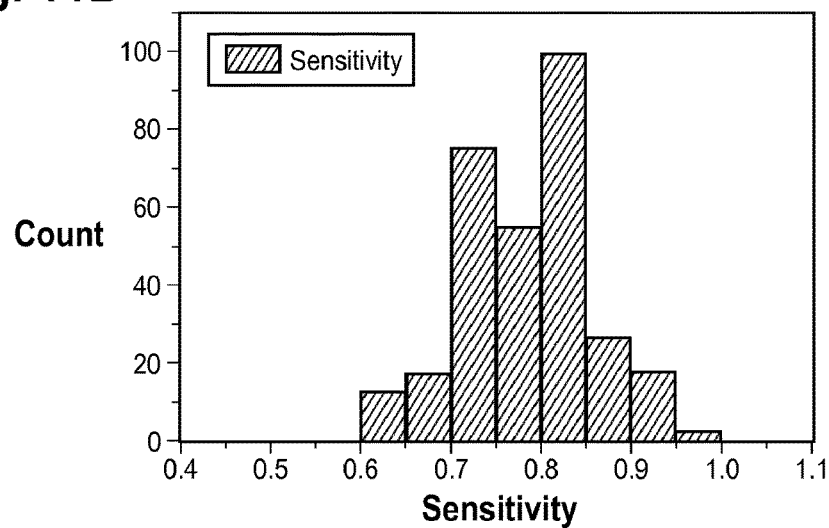
Figure 11C:
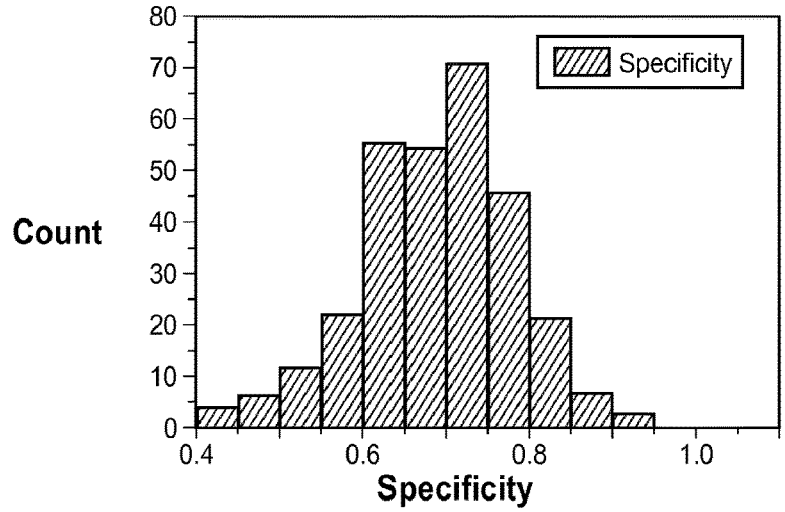

The distributions of each of these metrics across the created 301 MCs is shown in FIGS. 11A-11C. The performance of this classifier is fairly good in terms of overall accuracy as well as accuracy within each risk group ("High" and "Low"). In addition, the distributions of the metrics for the 301 MCs are well behaved and centered on the average values.

One hypothesis for this significantly better performance relative to Approach 1 has to do with the bigger training set (24 samples for "High" and 22 for "Low") used in Approach 2 while only 11 of each group were used in Approach 1.

The statistically significant difference between the two Kaplan-Meier curves ("High" and "Low"), as demonstrated in FIG. 9, supported by the accuracy performances, points to a good discrimination power of the classifier. Taking the development set, those patients classified (by MMV) as "Low" have 87.3% probability of not progressing in a period of 3 years or 82.9% in a period of 4 years. This compares to a probability of not progressing of 63.9% and 58.8% in a period of 3 and 4 years, respectively, for the patients classified as "High" risk.

Approach 3. The label flip process explained above in Approach 3 did not significantly improve the overall discrimination power of the classifier as compared to Approach 2, as assessed on the associated test sets. However, based on our experience with other projects, we expect the generalization power of a test derived from a convergence of label flips to be better than one derived without label flips. The Kaplan-Meier curves constructed using the MMV labels after each iteration are shown in the FIG. 12, along with the outcome statistical metrics. Like the Kaplan-Meier plot of FIG. 9, the plots of FIG. 12 show a clear separation of the TTP curves between those samples testing Low and High.

t-SNE Visualization t-Distributed Stochastic Neighbor Embedding (t-SNE) is a tool that allows the visualization of high-dimensional data in a 2D or 3D-map, and is introduced previously in Example 1. FIG. 13 shows the 2D maps of the data obtained through t-SNE for the initial assignment of group labels for the development set and for the final classification labels, for each of approaches 1, 2 and 3 described above. Each point is represented with a marker that identifies to which risk label it was assigned ("High" or "Low"). Note that the t-SNE map for the final classification in each of the approaches is more ordered with clustering of the high and low classification labels as compared to the maps of the initial assignments.

Assessment of the final classifier on the 46 patients reserved in the "validation set" cohort did not prove to be informative on the accuracy of the above classifier performance estimates, as analysis was limited by the lack of any progression events in this subgroup. Hence, the 46 patients not included in classifier development were simply combined with the development set to assess the performance of the classifier on the full study population. The results are shown in FIG. 14. In particular, FIG. 14 shows the Kaplan-Meier curves for TTP using classification labels obtained in Approach 2 and including the classification of the patients of the "validation set". For the patients that were used in the test/training splits the MMV label is taken. For the "validation set" patients, the normal majority vote of all the 301 MCs is used. The log-rank p-value is 0.025 and the log-rank Hazard Ratio 2.95 with a 95% CI of [1.13,5.83]. A table showing the percent progression free for each classified risk group at 3, 4 and 5 years on study is also shown in FIG. 14. Again, like FIGS. 9 and 12, the Kaplan-Meier plot of TTP in FIG. 14 shows clear separation of the High and Low groups.

Assessment of Correlation of the Classification Groups with TGS and PSA

It is interesting to assess if the classification groups ("High" and "Low") resulting from the classifier developed in Approach 2 (the one with best performance) are correlated with the Total Gleason Score (TGS) values and PSA baseline levels determined at the beginning of the study. Note that baseline PSA level was available for only 119 of the 137 patients and TGS only for 133 patients.

The distribution of the baseline PSA levels (taken at the beginning of the study) of both the "High" and the "Low" groups as classified in approach 2 are shown in FIG. 15. FIG. 15 are Box and Whisker plots of the distribution of the PSA baseline levels (taken at the beginning of the study) of the two classification groups (approach 2). For the patients that were used in the test/training splits the MMV label is taken. For the "validation set" patients, the normal majority vote of all the 301 MCs is used. The median PSA of the "High" group is 6.15 ng/ml and that of the "Low" group is 7.42 ng/ml. An unpaired Mann-Whitney test, which compares the ranks of the two groups, gives a p-value of 0.19, which indicates that the PSA distributions of the two groups are not significantly different. Thus, no correlation between the baseline PSA level and the cancer progression risk as given by the classifier is evident. This indicates that the classifier of this Example 2 is, in some sense, an orthogonal measurement to PSA as a predictor of risk of prostate cancer progression.

The distribution of the TGS values of both the "High" and the "Low" groups after classification in Approach 2 is shown in FIG. 16. In particular, in FIG. 16 for the patients that were used in the test/training splits the MMV label is taken. For the "validation set" patients, the normal majority vote of all the 301 MCs is used. Only the 133 patients (from the development and validations sets) for whom TGS was available are considered in this plot. A Fisher's exact test applied to the table shown in FIG. 16 gives a p-value of 0.61 for getting the observed correlation or stronger, assuming that there is no correlation between the TGS values and the classification labels. Thus, the null-hypothesis cannot be rejected and there is no evidence for a correlation between TGS and progression risk category, as given by the developed classifier. Again, this indicates that the classifier of this Example 2 is, in some sense, an orthogonal measurement to TGS as a predictor of risk of prostate cancer progression.

The classifier developed in Approach 2 discriminates fairly well between "High" and "Low" prostate cancer progression risk as evaluated considering the outcome data of the patients. However, neither the TG scores nor the PSA baseline values, which constitute the only available additional clinical data in the studied data set, seem to be correlated with such risk, as labeled by the classifier. It is possible that other clinical data could show some significant correlation, but this could only be assessed with a more complete data set containing other relevant baseline prognostic factors.

Conclusions for Example 2

Three different approaches were tried in order to develop a CMC/D classifier capable of assessing the aggressiveness or indolence of a patient's cancer in a population with low Total Gleason Score (TGS<8) and in watchful waiting. A development set of MALDI mass spectra obtained from plasma samples from 137 patients was used. Two of the approaches were different in terms of the chosen initial risk group definitions, while the third one consisted of a sequence of label flip iterations. The performance of the CMC/D classifiers was evaluated in terms of the hazard ratio between the two classification groups ("High" risk and "Low" risk) using the outcome data (inferred Time to Progression) available in the data set, as well as in terms of overall accuracy, sensitivity and specificity in terms of predicting a progression within the time of the study.

The best classifier (from Approach 2) is characterized by a hazard ratio of 2.74 with a 95% CI of 1.05-5.49, indicating a significantly better prognosis for patients assigned to the "Low" risk group. Our data hint at a better effect size than two commercially available sets: 1. Genomic Health, see Klein, A. E., et al. A 17-gene Assay to Predict Prostate Cancer Aggressiveness in the Context of Gleason Grade Heterogeneity, Tumor Multifocality, and Biopsy Undersampling Euro Urol 66, 550-560 (2014), Odds Ratio ~2.1-2.3, in the correct population, but might be because they only have TGS <=6; and 2. Myriad (Cooperberg, M. R., et al. Validation of a Cell-Cycle Progression Gene Panel to Improve Risk Stratification in a Contemporary Prostatectomy Cohort, J Clin Oncol 31, 1428-1434 (2013) in a radical prostatectomy population, Odds Ratio 2.1-2.3). When considering the whole population of the sample set, the percent progression free in the "High" risk group is 73% and 69% at 3 and 4 years, respectively, while in the "Low" group the percent of patients progression free is 92% and 88% for the same times after study entry. Although this remains to be validated on an internal validation set (step 1146, FIG. 1, which was not available due to the small number of samples available) or, better, an independent validation set from a separate study (step 1148 of FIG. 1), these classifier performance estimates are promising: they could possibly lead to a test that would guide actions to take regarding prostate cancer patients with low TGS. Further investigation of CMC/D classification within this prostate cancer indication is definitely worthwhile.

Example 3: Tyrol Prostate Cancer Screening Demonstration Project Data Set and Deep-MALDI Spectra A third example of a method for generating a classifier for predicting aggressiveness or indolence of prostate cancer from a multitude of blood-based samples obtained from prostate cancer patients will be described in this section. The methodology of classifier generation is similar to that described above in Examples 1 and 2, see FIG. 1. However, in this example we obtained mass spectral data from the samples using a method we refer to as "Deep MALDI", see US patent application publication 2013/0320203 of H. Roder et al., inventors. The description of mass spectral acquisition and spectral data processing set forth in the '203 application publication is incorporated by reference. Additionally, there were some differences in the patient population and course of treatment in this data set as compared to the sets of Examples 1 and 2. Nevertheless, in this section we describe several classifiers that we developed which can be used to predict aggressiveness or indolence of prostate cancer.

The samples analyzed in this study were collected as part of the Tyrol Prostate Cancer Screening Demonstration Project. See Bartsch G, Horninger W, Klocker H, Pelzer A, Bektic J, Oberaigner W et al., *Tyrol Prostate Cancer Demonstration Project: early detection, treatment, outcome, incidence and mortality*. BJU Int 2008: 101(7):809-816. doi: 10.1111/j.1464-410x.2008.07502.x. This is an exemplary study of the use of PSA measurement for prostate cancer screening. The Tyrol region of Austria, with a population of around 7.8 million, is geographically compact, with most of the population within 100 km of the main health care center of Innsbruck. This geographical situation and the willingness of the well-educated population to participate in preventative screening programs make this an ideal location for a population-wide screening study. PSA testing is freely available and encouraged for all men in Tyrol aged between 45 and 75 (and to men over 40 years old with a family history of prostate cancer) at the University Hospital of Innsbruck. Patients taking part in screening could volunteer to participate in the Tyrol Prostate Cancer Screening Demonstration Project (TPCSDP), which implemented an early detection algorithm, which was updated to keep pace with advances in clinical practice during the course of more than 20 years. In addition to collecting samples in the screening setting, the study continued to collect samples from patients once a diagnosis of prostate cancer was made and through various stages of treatment. In addition, clinical, treatment and outcome data were collected. The biobank created as part of the TPCSDP and the associated well-curated clinical data is an invaluable resource for studies aimed at understanding all stages of prostate cancer and its treatment, including investigations directed at the development of test and biomarkers that could improve patient care.

The aim of the study of Example 3 was to develop a blood-based test for prognosis in patients with detected prostate cancer classified as low risk based on Gleason scores obtained from diagnostic biopsy. Here, the term "test for prognosis" is used to interchangeably with a test for whether the patient's prostate cancer is indolent or aggressive, as explained previously in this document. Previous work on plasma samples obtained from a cohort of patients in a "watchful waiting" protocol (Example 2, "low risk" patients with Gleason scores of 7 or lower assigned to a protocol of monitoring rather than immediate radical prostatectomy (RPE)) had shown the potential for such a blood test with clinical relevant performance, as explained in Examples 1 and 2 above. While the group of patients with a Gleason score of six or lower is at relatively low risk of aggressive prostate cancer with quick disease progression and associated impact on survival, the cancer of some patients within this group is aggressive and does progress quickly. It is of clinical relevance to be able to identify which patients within this general low risk category are indeed at higher risk of quick progression of aggressive disease so that these patients can be directed to immediate intervention with appropriate therapies, which patients at genuine low risk can still be assigned to a watchful waiting or active surveillance protocol and avoid possibilities of side effects of unnecessary treatment. Hence, the test described in this Example is of clinical significance.

The option of active surveillance was not commonly offered in Tyrol during the period for which the TPCSDP has adequate follow up for collected samples to be of use for this study. Hence, this project involves analysis of samples collected from patients at time points close to their diagnosis with prostate cancer (diagnosis was always confirmed by biopsy) with Gleason scores of 6 or lower, who went on to undergo radical prostatectomy (RPE). The relative level of aggression of disease could then be assessed by the time to relapse of prostate cancer following RPE.

Samples

Serum samples from prostate cancer patients enrolled in the TPCSDP study were provided and used in this project. For classifier development, only patients were considered who underwent biopsy and RPE within a year of the sample collection. Thus, at the time the patients' blood samples were taken the patients had been diagnosed with prostate cancer but had not yet undergone RPE. In addition, generated mass spectra of the serum samples had to pass quality controls, and clinical data (outcome as well as PSA, % fPSA, and age) had to be available. This left a total of 124 samples for classifier development. The clinical characteristics of the development set of samples are summarized in table 13. All the samples were obtained from prostate cancer patients who, at the time the sample was obtained, had a total Gleason score of 6 or lower.

TABLE 13

Clinical characteristics of patients with samples used in the development set

| | | Median (Range) |
|---|---|---|
| PSA | | 3.85 (1.30-8.72) |
| % fPSA | | 15.8 (5.7-47.1) |
| Age at diagnosis | | 60.5 (42.9-74.3) |

| | | n (%) |
|---|---|---|
| Total Gleason Score (biopsy) | 2 | 1 (1) |
| | 3 | 0 (0) |
| | 4 | 1 (1) |
| | 5 | 3 (2) |
| | 6 | 119 (96) |
| Gleason Score 1 (biopsy) | 1 | 1 (1) |
| | 2 | 3 (2) |
| | 3 | 120 (97) |
| Gleason Score 2 (biopsy) | 1 | 1 (1) |
| | 2 | 2 (2) |
| | 3 | 121 (98) |
| Total Gleason Score (RPE) | 4 | 1 (1) |
| | 5 | 24 (19) |
| | 6 | 40 (32) |
| | 7 | 51 (41) |
| | 8 | 6 (5) |
| | 9 | 1 (1) |
| | NA | 1 (1) |
| Gleason Score 1 (RPE) | 2 | 7 (6) |
| | 3 | 108 (87) |
| | 4 | 8 (6) |
| | NA | 1 (1) |

TABLE 13-continued

Clinical characteristics of patients with samples used in the development set

| Gleason Score 2 (RPE) | 2 | 20 (16) |
|---|---|---|
| | 3 | 48 (39) |
| | 4 | 49 (40) |
| | 5 | 5 (4) |
| | NA | 2 (2) |
| pT Staging (RPE) | 2a | 18 (15) |
| | 2b | 3 (2) |
| | 2c | 85 (69) |
| | 3a | 17 (14) |
| | NA | 1 (1) |

Sample Preparation

Samples were thawed and 3 µl aliquots of each test sample (serum from patients with prostate cancer) and quality control serum (a pooled sample obtained from serum of five healthy patients, purchased from ProMedDx, "SerumP3") were spotted onto VeriStrat® serum cards (Therapak). The cards were allowed to dry for 1 hour at ambient temperature after which the whole serum spot was punched out with a 6 mm skin biopsy punch (Acuderm). Each punch was placed in a centrifugal filter with 0.45 µm nylon membrane (VWR). One hundred µl of HPLC grade water (JT Baker) was added to the centrifugal filter containing the punch. The punches were vortexed gently for 10 minutes then spun down at 14,000 rcf for 2 minutes. The flow-through was removed and transferred back on to the punch for a second round of extraction. For the second round of extraction, the punches were vortexed gently for 3 minutes then spun down at 14,000 rcf for 2 minutes. Twenty microliters of the filtrate from each sample was then transferred to a 0.5 ml eppendorf tube for MALDI analysis.

All subsequent sample preparation steps were carried out in a custom designed humidity and temperature control chamber (Coy Laboratory). The temperature was set to 30° C. and the relative humidity at 10%.

An equal volume of freshly prepared matrix (25 mg of sinapinic acid per 1 ml of 50% acetonitrile:50% water plus 0.1% TFA) was added to each 20 µl serum extract and the mix vortexed for 30 sec. The first three aliquots (2×2 µl) of sample:matrix mix were discarded into the tube cap. Eight aliquots of 2 µl sample:matrix mix were then spotted onto 8 different sample spot locations of a stainless steel MALDI target plate (SimulTOF). The MALDI target was allowed to dry in the chamber before placement in the MALDI mass spectrometer.

This set of samples was processed for MALDI analysis in 6 batches. QC samples were added to the beginning (2 preparations) and end (2 preparations) of each batch run.

Spectral Acquisition

MALDI spectra were obtained using a MALDI-TOF mass spectrometer (SimulTOF 100 from Virgin Instruments, Sudbury, Mass., USA). The instrument was set to operate in positive ion mode, with ions generated using a 349 nm, diode-pumped, frequency-tripled Nd:YLF laser operated at a laser repetition rate of 0.5 kHz. External calibration was performed using a mixture of standard proteins (Bruker Daltonics, Germany) consisting of insulin (m/z 5734.51), ubiquitin (m/z 8565.76), cytochrome C (m/z 12360.97), and myoglobin (m/z 16952.30).

Spectra from each MALDI spot were collected as 800 shot spectra that were 'hardware averaged' as the laser fires continuously across the spot while the stage is moving at a speed of 0.25 mm/sec. A minimum intensity threshold of 0.01 V was used to discard any 'flat line' spectra. All 800 shot spectra with intensity above this threshold were acquired without any further processing. The spectral acquisition used a raster scanning method which is described in U.S. patent application publication 2013/0320203 of H. Roder et al., inventors.

Raster Spectral Preprocessing

Raster Spectra Rescaling by Batch

A coarse alignment step was performed to overcome shifts in the m/z grid resulting from instrument calibration. As the instrument is recalibrated prior to batch acquisition, rescaling was performed independently by batch. An m/z grid shift factor was determined for each batch by comparing peaks in the first acquired reference spectrum to a historical reference spectrum. The m/z grid from the historical reference was applied to the newly acquired spectra with the calculated shift.

Alignment and Filtering of Raster Spectra

This workflow performs a ripple filter, as it was observed that using this procedure improved the resulting averages in terms of noise. The spectra were then background subtracted and peaks were found in order to perform alignment. The spectra that were used in averaging were the aligned ripple filtered spectra without any other preprocessing. The calibration step used a set of 43 alignment points listed below in table 14. Additional filtering parameters required that the spectra had at least 20 peaks and that at least 5 of the alignment points were used in alignment.

TABLE 14

Alignment points used to align the raster spectra

| m/z |
|---|
| 3168 |
| 4153 |
| 4183 |
| 4792 |
| 5773 |
| 5802 |
| 6433 |
| 6631 |
| 7202 |
| 7563 |
| 7614 |
| 7934 |
| 8034 |
| 8206 |
| 8684 |
| 8812 |
| 8919 |
| 8994 |
| 9133 |
| 9310 |
| 9427 |
| 10739 |
| 10938 |
| 11527 |
| 12173 |
| 12572 |
| 12864 |
| 13555 |
| 13763 |
| 13882 |
| 14040 |
| 14405 |
| 15127 |
| 15263 |
| 15869 |
| 17253 |
| 18630 |
| 21066 |
| 23024 |
| 28090 |
| 28298 |
| 33500 |
| 67150 |

Raster Spectra Averaging

Averages were created from the pool of rescaled, aligned and filtered raster spectra. We collected multiple 800 shot spectra per spot, so that we end up with a pool in excess of 500 in number of 800 shot raster spectra from the 8 spots from each sample. We randomly select 500 from this pool, which we average together to create a final 400,000 shot average deep MALDI spectrum.

Pre-Processing of Averaged Spectra

Background Estimation and Subtraction

Details regarding background subtraction are known in the art and describe in U.S. Pat. No. 7,736,905, the content of which is incorporated by reference. Estimation of background was performed with additional consideration for the high mass region. The two window method of background estimation and subtraction was used (Table 15).

TABLE 15

Background estimation windows

| | m/Z | width |
|---|---|---|
| Wide windows | 3000 | 80000 |
| | 30000 | 80000 |
| | 31000 | 160000 |
| Medium windows | 3000 | 5000 |
| | 30000 | 5000 |
| | 31000 | 10000 |

Normalization of Spectra

A normalization scalar was determined for each spectrum using a set of normalization windows. These windows were taken from the bin method parameters from a pre-existing project using Deep-MALDI. While a new set of windows was investigated for this Example dataset, a superior set was not found. The normalization was performed in a two stage process. First, the spectra were normalized using the windows found in table 16. Following, the spectra were normalized using the windows found in table 17.

TABLE 16

Step 1 normalization windows

| Left | Right |
|---|---|
| 3530.679 | 3784.658 |
| 3785.029 | 4078.739 |
| 4220.21 | 4323.065 |
| 4875.581 | 4943.903 |
| 5260.635 | 5435.524 |
| 5436.47 | 5682.433 |
| 6050.421 | 6376.807 |
| 6510.852 | 6601.081 |
| 7751.414 | 7898.826 |
| 10606.12 | 10897.2 |
| 10908.61 | 11356.51 |
| 12425.27 | 12527.26 |
| 17710.35 | 18504.69 |
| 19212.92 | 20743.82 |
| 22108.95 | 22959.15 |
| 23738.5 | 24739.04 |

TABLE 17

Step 2 normalization windows

| Left | Right |
|---|---|
| 4168.226 | 4219.839 |
| 4875.581 | 4943.903 |
| 4946.131 | 5077.576 |
| 5080.918 | 5259.892 |
| 5260.635 | 5435.524 |
| 6510.852 | 6601.081 |
| 7751.414 | 7898.826 |
| 10606.12 | 10897.2 |
| 10908.61 | 11356.51 |

Figure 17:
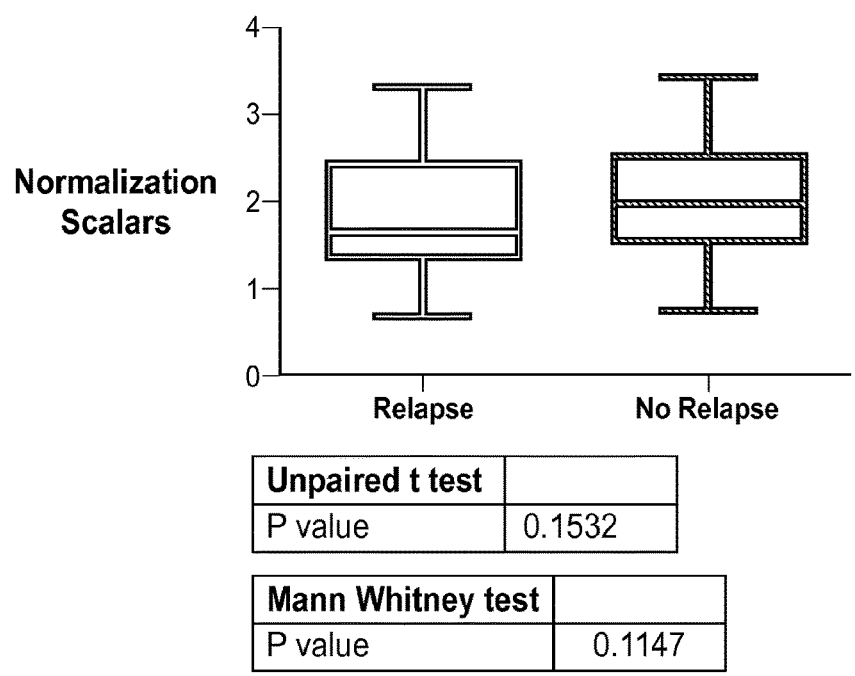
FIG. 17 is a box and whisker plot showing normalization scalars for spectra for Relapse and No Relapse patient groups in Example 3.

The normalization scalars that were found for each average were compared by t-test by clinical group Relapse (patients relapsing after RPE) versus NoRelapse (patients not relapsing after RPE). As shown in FIG. 17, the scalars were not found to be significantly associated with patient relapse status. (Note, at this point we have not yet initiated the classifier development process of FIG. 1 and hence have not yet generated or assigned class labels for the samples. We just used the Relapse and NoRelapse labels to confirm that our normalization scalars were acceptable.)

Average Spectra Alignment

The peak alignment of the average spectra is typically very good; however, a fine-tune alignment step was performed to address minor differences in peak positions in the spectra. A set of alignment points was identified and applied to the analysis spectra (table 18).

TABLE 18

Calibration points used to align the spectral averages

| m/Z |
|---|
| 3315 |
| 4153 |
| 4457 |
| 4710 |
| 5066 |
| 6433 |
| 6631 |
| 7934 |
| 8916 |
| 9423 |
| 9714 |
| 12868 |
| 13766 |
| 14045 |
| 14093 |
| 15131 |
| 15872 |
| 16078 |
| 17256 |
| 17383 |
| 18631 |
| 21069 |
| 21168 |
| 28084 |
| 28293 |
| 67150 |

Feature Definitions

Figure 18:
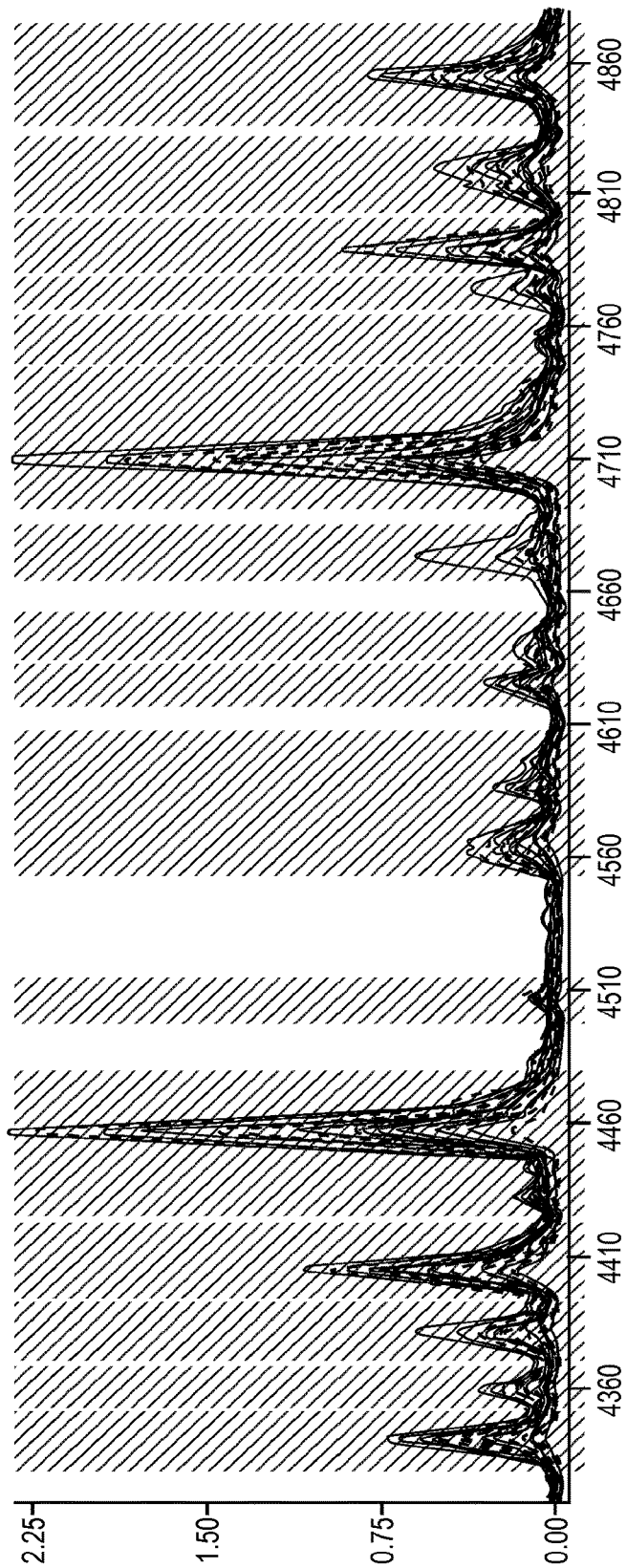
FIG. 18 is a plot of a multitude of mass spectra showing example feature definitions;
i.e., m/z ranges over which integrated intensity values are calculated to give feature values for use in classification.

Feature definitions (i.e., selection of features or m/z ranges to use for classification) were selected interactively by viewing the spectra. The left and right boundaries were assigned manually using an overlay of many spectra. The process was performed iteratively over batches to ensure that the boundaries and features were representative of the whole dataset. A final iteration was performed using the class labels assigned to the spectra of 'Relapse' and 'No Relapse' to ensure selected features were appropriately assigned considering these clinical groupings. A total of 329 features were identified to use in the new classifier development project. These feature definitions were applied to all spectra to create a feature table of feature values. An example of the selected features is shown in FIG. 18. The full list of feature definitions can be found in Example 3 Appendix A, table A1. After the feature definitions are assigned, a feature table is created by computing the integrated intensity value of the spectra over each of the features listed in the Example 3 Appendix A table A1.

Batch Correction of Spectra

SerumP3 Analysis

Two preparations of the reference sample, SerumP3, were plated at the beginning (1, 2) and end (3, 4) of each run. The purpose of these samples is to ensure that variations by batch due to slight changes in instrument performance (for example, aging of the detector) can be corrected for. The section below describes the batch correction procedure. To perform batch correction, one spectrum must serve as the reference for the batch which is an average of one of the preparations from the beginning and one from the end of the batch. A procedure for selecting the pair is first described.

The reference samples were preprocessed as described above. All 329 features were used to evaluate the possible combinations (1-3, 1-4, 2-3, 2-4). We compared each possible combination of replicates using the function:

$$A = \min(abs(1-ftrval1/ftrval2), abs(1-ftrval2/ftrval1))$$

where ftrval1 (ftrval2) is the value of a feature for the first (second) replicate of the replicate pair. This quantity A gives a measure of how similar the replicates of the pair are. For each feature, A is reported. If the value is >0.5, then the feature is determined to be discordant, or 'Bad'. A tally of the bad features is reported for each possible combination. If the value of A is <0.1, then the feature is determined to be concordant and reported as 'Good'. A tally of the Good features is reported for each possible combination. Using the tallies of Bad and Good features from each possible combination, we computed the ratio of Bad/Good. The combination with the lowest ratio was reported as the most similar combination and unlikely to contain any systematic or localized outlier behavior in either of the reference spectra. Finally, if no ratio can be found that is less than 0.25, then the batch is a failure. This threshold was easily met for all batches. The highest threshold was 0.125.

Batch Correction

Batch 1 was used as the baseline batch to correct all other batches. The reference sample was used to find the correction coefficients for each of the batches 2-6 by the following procedure.

Within each batch j ($2 \leq j \leq 6$), the ratio $$\hat{r}_i^j = \frac{A_i^j}{A_i^1}$$

and the average amplitude $\overline{A}_i^j = \frac{1}{2}(A_i^j + A_i^1)$ are defined for each $i^{th}$ feature centered at $(m/z)_i$, where $A_i^j$ is the average reference spectra amplitude of feature i in the batch being corrected and $A_i^1$ is the reference spectra amplitude of feature i in batch 1 (the reference standard). It is assumed that the ratio of amplitudes between two batches follows the dependence $$r(\overline{A}, (m/z)) = (a_0 + a_1 \ln(\overline{A})) + (b_0 + b_1 \ln(\overline{A}))(m/z) + c_0(m/z)^2.$$

On a batch to batch basis, a continuous fit is constructed by minimizing the sum of the square residuals, $\Delta^j = \Sigma_i (\hat{r}_i^j - $ $r^j(a_0, a_1, b_0, b_1, c_0))^2$, and using the experimental data of the reference sample. The SerumP3 reference samples are used to calculate the correction function. Steps were taken to not include outlier points in order to avoid bias in the parameter estimates. The values of the coefficients $a_0$, $a_1$, $b_0$, $b_1$ and $c_0$, obtained for the different batches are listed in Example 3 Appendix B (table B.1). The projection in the $\hat{r}_i^j$ versus $(m/z)_i$ plane of the points used to construct the fit for each batch of reference spectra, together with the surface defined by the fit itself, is shown in figure B.1 of Appendix B.

Once the final fit, $r^j(\overline{A}, m/z)$, is determined for each batch, the next step is to correct, for all the samples, all the features (with amplitude A at (m/z)) according to $$A_{corr} = \frac{A}{r^j(\overline{A}, (m/z))}.$$

After this correction, the corrected $(\overline{A}_i^j, (m/z)_i, \hat{r}_i^j)$ feature values calculated for reference spectra lie around the horizontal line defined by r=1, as shown in Figure B.2 of Example 3 Appendix B. Post correction coefficients are calculated to compare to quality control thresholds. These coefficients can be found in Example 3 Appendix B table B.2 and the corresponding plots in Figure B.2 of the appendix.

Final Feature Table Assembly

Normalization by Partial Ion Current (PIC) Method

The batch corrected feature table was examined to find regions on intrinsic stability to use as the final normalization windows. First, the univariate p values were found by comparing the clinical groups Relapse and No Relapse. Features with p values less than 0.15 were excluded from the PIC analysis as these features may contribute meaningful information in test development. A set of 188 features were used in the PIC analysis, of which 13 features were used in normalization (see table 19).

TABLE 19

Features used in the final normalization

PIC Features 4459
4718
4818
4856
6612
6634
8928
9430
9641
9721
12873
12968
13081

Partial ion current normalization of spectra is known in the art, see e.g., U.S. Pat. No. 7,736,905, therefore a detailed description is omitted for the sake of brevity.

Figure 19:
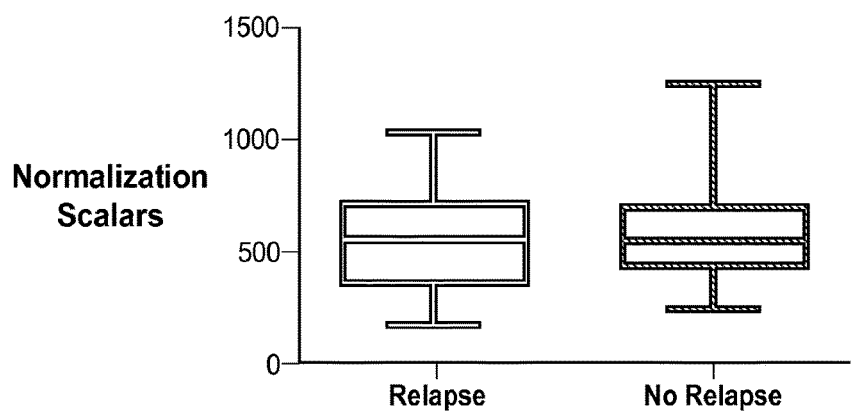
FIG. 19 is a box and whisker plot showing normalization scalars found by partial ion current normalization analysis comparison between clinical groups Relapse and No Relapse.

The normalization scalars computed using the features found in table 19 were compared by clinical group (Relapse, NoRelapse) to ensure normalization would not impede the new classifier development effort. As shown in FIG. 19, no association was found between the scalars and the clinical group.

Following PIC normalization, the feature table was finalized for use in the classifier development process described below. That is, integrated intensity values of the features selected for classification was computed and stored in a table for each of the spectra in the development set.

SerumP3 Analysis of Features

As a final assessment of the preprocessing procedure, the Serum P3 samples were analyzed across all batches in the initial feature table and following the PIC normalization. Prior to batch correction, the median and average CVs were 14.2% and 17.5% respectively. Following batch correction and the final normalization, the median and average CVs for the SerumP3 samples were 13.7% and 17.4%. These modest improvements reflect the relatively small role of batch correction in the processing of data and demonstrate that little variability is introduced across batches.

Classifier Development for Example 3

The new classifier development process was carried out using the platform/methodology shown in FIG. 1, and described previously at some length, which we have termed "Diagnostic Cortex"™. The methodology of FIG. 1 is particularly useful for constructing a classifier and building a prognostic test where it is not a priori obvious which patients should be assigned to the better or worse prognosis groups (Low and High Risk, or Early and Late relapse/progression, respectively in FIG. 1, blocks 1104 and 1106). The risk of overfitting to the data is minimized by regularization (step 1132) and the use of majority voting or average probability cutoff in the selection or definition of the final classifier at step 1144. Confidence in performance metrics for a classifier generated by the method of FIG. 1 is enhanced by the observation of many master classifiers (MCs) with similarly good performance and the use of out-of-bag estimates for performance metrics.

The classifier generation procedure is described in some detail in Examples 1 and 2 above. The reader is also directed to the US patent application publication no. 2015/0102216, H. Roder et al. inventors, for a further description and examples of the methodology. The following discussion will provide further explanations of the method in the present Example 3.

Definition of Class Labels

As shown in FIG. 1 step 1102, an initial class label assignment is made for each of the samples in the development set 1100, in this example the 124 blood-based samples that passed QC filtering and for which patient clinical data was available. In this example, we are trying to assign the correct class label for each sample, either Low Risk or High Risk (or, equivalently, Late or Early, respectively), with Low Risk or the equivalent signifying good prognosis, indolence, and late progression of disease and High Risk or the equivalent signifying relatively poor prognosis, aggressiveness of the prostate cancer, and early progression of disease. Time-to-event data, in this case time from sample collection to relapse after RPE was used for assigning the initial class label and classifier training. In this situation, class labels are not obvious and, as shown in FIG. 1, the method uses an iterative method to refine class labels at the same time as creating the classifier. See loop 1142. An initial guess is made for the class labels at step 1102. The samples are sorted on time to relapse and half of the samples with the lowest time-to-event outcome are assigned the "Early" class label (early relapse, i.e. poor outcome, high risk) while the other half are assigned the "Late" class label (late relapse, i.e. good outcome, low risk). A classifier is then constructed using the outcome data and these class labels. This classifier can then be used to generate classifications for all of the development set samples and these are then used as the new class labels for a second iteration of the classifier construction step. This process is iterated until convergence (i.e., the number of persistently misclassified samples is minimized at step 1140 after multiple iterations through the process of FIG. 1 including loop 1142).

Creation and Filtering of Mini-Classifiers (Steps 1120 and 1126)

The development set samples 1100 were split into training and test sets in multiple different random realizations. See Step 1108, FIG. 1 and loop 1136. Six hundred and twenty five realizations (iterations through loop 1136) were used.

In step 1120, many k-nearest neighbor (kNN) mini-classifiers (mCs) that use the training set as their reference set were constructed using subsets of features. In this project we tried two different approaches in terms of the nature of features used by the mini-classifiers. In approach (1), see description below, we used only mass spectral features while in approach (2), see description below, in addition to those mass spectral features, we also used age, PSA and % fPSA as features for classification by the mini-classifiers.

To be able to consider subsets of single, two, or three features and improve classifier performance, it was necessary to deselect features that were not useful for classification from the set of 329 features of Example 3 Appendix A. Feature deselection was carried out using the bagged method outlined in Example 3 Appendix C. In the case of approach (2), age, PSA and % fPSA did not pass the filtering criteria of the bagged method more times than the applied threshold, but we kept these three features for classifier training nevertheless. The methodology of deselection of features is disclosed in U.S. provisional application of J. Roder et al., Ser. No. 62/154,844 filed Apr. 30, 2015, the contents of which is incorporated by reference herein.

To target a final classifier that has certain performance characteristics, these mCs are filtered at step 1126. Each mC is applied to its training set and performance metrics are calculated from the resulting classifications of the training set. Only mCs that satisfy thresholds on these performance metrics pass filtering to be used further in the process. The mCs that fail filtering are discarded. For this project only hazard ratio filtering was used, i.e. the classifier was applied to the training set of samples and the hazard ratio calculated between the time to relapse for the two classification groups had to lie within a preset range for the mC to pass filtering. The filtering options used in this project are listed in table 20

TABLE 20

| | Filtering parameters used in step 1126 FIG. 1 | | | |
|---|---|---|---|---|
| | Approach (1) | | Approach (2) | |
| Iteration of loop 1142 of FIG. 1 | k | HR filtering range | k | HR filtering range |
| 0 | 7 | 3.0-10.0 | 7 | 3.0-10.0 |
| 1 | 7 | 2.5-10.0 | 7 | 2.0-10.0 |
| 2 | 7 | 2.5-10.0 | 7 | 2.5-10.0 |

Here in Table 20 and below, "iteration" means an exercise of classifier generation using the through the loop 1142 of FIG. 1 with "iteration 0" referring to an initial iteration through the process, "iteration 1" referring to a second iteration, etc. It will be appreciated that by experimenting with the parameters for the classifier generation process, such as for example filtering parameters for the mini-classifiers, the number of features used by the mini-classifiers, or inclusion of additional non-mass spectral features for classification such as PSA level, age, etc., and performing the process of FIG. 1 many times, one can explore the performance of classifiers generated using the process of FIG. 1 to find one that has optimal performance.

Combination of Mini-Classifiers Using Logistic Regression with Drop-Out

Once the filtering step 1126 is complete, at step 1130, the mini-classifiers are combined into one master classifier using logistic regression trained using the training set labels as indicated 1132 in FIG. 1. To help avoid overfitting the regression is regularized using extreme drop out with only a small number of the mCs chosen randomly for inclusion in each of the logistic regression iterations. The number of dropout iterations in step 1132 was selected based on the typical number of mCs passing filtering to ensure that each mC was likely to be included within the drop out process multiple times. For this project 10 mCs were randomly selected for each drop out iteration. The number of drop out iterations that were carried out in each iteration are listed in table 21.

TABLE 21

| Number of drop out iterations used | | |
|---|---|---|
| Iteration (of loop 1142 of FIG. 1) | Approach (1) | Approach (2) |
| 0 | 300,000 | 300,000 |
| 1 | 250,000 | 300,000 |
| 2 | 250,000 | 200,000 |

Training/Test Set Splits (Loop 1136)

The use of multiple training/test splits (loop 1136) and evaluation of Master Classifier (MC) performance on the new test set in each iteration) avoids selection of a single, particularly advantageous or difficult, training set for classifier creation and avoids bias in performance assessment from testing on a test set that could be especially easy or difficult to classify.

The output of the logistic regression performed at step 1132 that defines each MC is a probability of being in one of the two training classes (Early or Late). During the iterative classifier construction and label refinement process, classifications were assigned by majority vote of the individual MC labels obtained with a cutoff of 0.5 applied to the logistic regression output. This process was modified to incorporate only MCs where the sample was not in the training set (modified, or "out-of-bag" majority vote, MMV).

Example 3 Results

The performance of the classifiers was assessed using Kaplan-Meier plots of time to relapse (time between sample collection and relapse after RPE), TTR, of samples classified as Early and Late, together with corresponding hazard ratios (HRs) and log-rank p values. Kaplan-Meier plots corresponding to the data in table 22 are shown in FIG. 20. The classifications per sample are listed in Example 3 Appendix E. Note in FIG. 20 that the classifiers generated in both approaches show a clear separation in time to relapse between the Early and Late class label groups. The results are summarized in table 22.

TABLE 22

Performance summary for time to relapse (Early vs Late)

| | #Early/#Late | HR (95% CI) | log-rank p |
|---|---|---|---|
| Approach (1) | 56/68 | 2.38 (1.08-5.73) | 0.035 |
| Approach (2) | 55/69 | 2.49 (1.13-6.07) | 0.026 |

TABLE 23

Percent relapse free for each classification risk group at 3, 4 and 5 years after sample collection

| Time on study [years] | Approach (1) Early (%) | Approach (1) Late (%) | Approach (2) Early (%) | Approach (2) Late (%) |
|---|---|---|---|---|
| 3 | 81 | 94 | 81 | 94 |
| 4 | 79 | 92 | 79 | 92 |
| 5 | 77 | 92 | 77 | 92 |
| 10 | 59 | 83 | 59 | 83 |

TABLE 24

Multivariate analysis of time to relapse

| Covariate | Approach (1) HR (95% CI) | Approach (1) P value | Approach (2) HR (95% CI) | Approach (2) P value |
|---|---|---|---|---|
| Late vs Early | 2.41 (1.00-5.82) | 0.050 | 2.64 (1.08-6.44) | 0.033 |
| PSA | 1.18 (0.94-1.47) | 0.150 | 1.18 (0.95-1.48) | 0.142 |
| fPSA | 1.00 (0.94-1.06) | 0.983 | 1.00 (0.94-1.06) | 0.955 |
| Age (50-59) .vs. <50) | 0.94 (0.12-7.59) | 0.955 | 0.98 (0.12-7.88) | 0.984 |
| Age (60-69) .vs. <50) | 0.65 (0.08-5.67) | 0.699 | 0.62 (0.07-5.41) | 0.665 |
| Age (>70 .vs. <50) | 0.59 (0.05-7.08) | 0.673 | 0.57 (0.05-6.86) | 0.656 |

Baseline clinical characteristics are summarized by classification group in table 25.

TABLE 25

Clinical characteristics by classification group

| | | Approach (1) Early (N = 56) | Approach (1) Late (N = 68) | Approach (2) Early (N = 55) | Approach (2) Late (N = 69) |
|---|---|---|---|---|---|
| | | | Median (Range) | | |
| PSA | | 3.96 (165-8.72) | 3.67 (1.3-8.4) | 3.99 (165-8.72) | 3.7 (1.3-8.4) |
| % fPSA | | 15.18 (6.2-47.1) | 15.88 (5.7-33.1) | 15.5 (6.2-47.1) | 15.85 (5.7-33.1) |
| Age at diagnosis | | 62.0 (46.8-74.3) | 59.5 (42.9-72.2) | 62.2 (46.8-74.3) | 59.5 (42.9-72.2) |
| | | | n (%) | | |
| Total Gleason Score (biopsy) | 2 | 1 (2) | 0 (0) | 1 (2) | 0 (0) |
| | 3 | 0 (0) | 0 (0) | 0 (0) | 0 (0) |
| | 4 | 0 (0) | 1 (1) | 0 (0) | 1 (1) |
| | 5 | 1 (2) | 2 (3) | 1 (2) | 2 (3) |
| | 6 | 54 (96) | 65 (96) | 53 (96) | 66 (96) |
| Gleason Score 1 (biopsy) | 1 | 1 (2) | 0 (0) | 1 (2) | 0 (0) |
| | 2 | 1 (2) | 2 (3) | 1 (2) | 2 (3) |
| | 3 | 54 (96) | 66 (97) | 53 (96) | 67 (97) |
| Gleason Score 2 (biopsy) | 1 | 1 (2) | 0 (0) | 1 (2) | 0 (0) |
| | 2 | 0 (0) | 2 (3) | 0 (0) | 2 (3) |
| | 3 | 55 (98) | 66 (97) | 54 (98) | 67 (97) |
| Total Gleason Score (RPE) | 4 | 0 (0) | 1 (1) | 0 (0) | 1 (1) |
| | 5 | 8 (14) | 16 (24) | 9 (16) | 15 (22) |
| | 6 | 16 (29) | 24 (35) | 15 (27) | 25 (36) |
| | 7 | 27 (48) | 24 (35) | 26 (47) | 25 (36) |
| | 8 | 5 (9) | 1 (1) | 5 (9) | 1 (1) |
| | 9 | 0 (0) | 1 (1) | 0 (0) | 1 (1) |
| | NA | 0 (0) | 1 (1) | 0 (0) | 1 (1) |
| Gleason Score 1 (RPE) | 2 | 2 (4) | 5 (7) | 2 (4) | 5 (7) |
| | 3 | 48 (86) | 60 (88) | 47 (85) | 61 (88) |
| | 4 | 6 (11) | 2 (3) | 6 (11) | 2 (3) |
| | NA | 0 (0) | 1 (1) | 0 (0) | 1 (1) |
| Gleason Score 2 (RPE) | 2 | 6 (11) | 14 (21) | 7 (13) | 13 (19) |
| | 3 | 22 (39) | 26 (38) | 21 (38) | 27 (39) |
| | 4 | 25 (45) | 24 (35) | 24 (44) | 25 (36) |
| | 5 | 3 (5) | 2 (3) | 3 (5) | 2 (3) |
| | NA | 0 (0) | 2 (3) | 0 (0) | 2 (3) |
| pT Staging (RPE) | 2a | 5 (9) | 13 (19) | 5 (9) | 13 (19) |
| | 2b | 2 (4) | 1 (1) | 2 (4) | 1 (1) |
| | 2c | 42 (75) | 43 (63) | 41 (75) | 44 (64) |
| | 3a | 7 (13) | 10 (15) | 7 (13) | 10 (14) |
| | NA | 0 (0) | 1 (1) | 0 (0) | 1 (1) |

The sample classifications were identical for the two approaches except for three samples which swapped classifications between the two. Inclusion of PSA, % fPSA and age may improve classification (Approach 2), but any improvement seems to be quite marginal. This is consistent with the lack of significance of PSA, % fPSA, and age as predictive factors for outcome in the multivariate analysis of table 25. Test classification remains a significant predictor of TTR and is the only available significantly predictive factor of TTR in multivariate analysis. While there is an indication that patients with higher TGS from RPE tend to be assigned an Early classification (5/6 patients with TGS 8 from RPE are classified as Early), larger sample numbers would be required to demonstrate this conclusively. As the vast majority of patients in this study had TGS by biopsy of 6, it is clear that the classifications obtained from the mass spectral analysis provide information in addition to Gleason score at time of diagnosis, before additional, more reliable tumor staging can be obtained after RPE. Furthermore, this information is independent of PSA and % fPSA measurements as shown by Mann-Whitney tests performed to assess association between these variables and the classification groups (table 26).

TABLE 26

| | Mann-Whitney test p-values | |
|---|---|---|
| | Approach (1) | Approach (2) |
| PSA | 0.105 | 0.118 |
| % fPSA | 0.474 | 0.767 |
| age | 0.111 | 0.052 |

Conclusions and Clinical Significance of Classifier Generated in Example 3

Applying the procedure of FIG. 1 to the feature table obtained from Deep MALDI spectra generated from serum samples collected from low risk prostate cancer patients and associated outcome data, it was possible to create a test able to stratify patients into two groups with better and worse prognosis following RPE, thus differentiating indolent from aggressive prostate cancer using a blood-based sample prior to RPE. The difference in TTR between the two classification groups was statistically significant and clinically meaningful, with a hazard ratio of around 2.5. See FIG. 20 and Tables 22-25. Slightly less than half of the patients were assigned to the poor prognosis group (Early). Five years after sample collection (at least 4 years after RPE), 92% of the patients in the good prognosis group were disease free compared with only 77% in the poor prognosis group (Late). This difference increased at ten years post sample collection, with 83% of patients relapse-free in the good prognosis group compared with 59% in the poor prognosis group.

The next step in the development of this potentially clinically useful test is to validate the current results in an independent cohort of patients in a similar indication. (See FIG. 1 step 1148). This is planned using an additional sample set collected from patients in the TPCSDP.

These results are in line with previous work on low risk prostate cancer based on plasma samples collected from patients in a watchful waiting protocol. See Examples 1 and 2. In the case of Example 2 (cohort of patients on watchful waiting with TGS of 7 or lower) at five years after sample collection, 88% of patients were progression-free in the good prognosis group compared with 69% of patients in the poor prognosis group, and the hazard ratio for time to progression between good and poor prognosis groups was 2.95 (95% CI: 1.13-5.83). In the present study, the indication was similar (low risk prostate cancer with Gleason score of 6 or below); however, in this present cohort all patients underwent RPE soon after diagnosis. As one would expect that this latter treatment paradigm should improve outcomes for the poor prognosis group more than the good prognosis group, one would expect that the hazard ratio in the present setting should be smaller than that in the watchful waiting setting. The consistency between the two development projects adds to our confidence in the classifiers described in this disclosure and their performance estimates.

As watchful waiting or active surveillance protocols are now becoming more widely applied to these "low risk" prostate cancer patients (see Klotz L, Zhang L, Lam A, et al, Long-term follow up of a large active surveillance cohort of patients with prostate cancer J. Clin. Oncol. 2015 (33):272-277; Morash C, Tey R, Agbassi C, et al., Can Urol Assoc 2015: 9(5-6): 171-178) and there are recognized issues determining whether all these patients should be considered as really "low risk" (see Cooperberg M., Long-Term Active Surveillance for Prostate Cancer: Answers and Questions. J. Clin. Oncol. 2015: 33 (3): 238-240), it would seem that clinical utility of the test in Example 3 may lie more in the prediction of outcomes following diagnosis of prostate cancer with Gleason score from biopsy of 6 or lower in an active surveillance setting, than in prediction of outcomes following RPE in this population. The test could indicate which patients in this "low risk" setting are really good candidates for active surveillance/watchful waiting and which patients should go straight on to more aggressive treatment regimens such as immediate RPE. Acquiring a set of serum samples from an active surveillance population to test performance of this test in that setting is therefore an important next step. As explained above, one might expect an even better separation in outcomes between classification groups in the active surveillance setting.

In addition, as this test is prognostic of relapse following RPE, it could be useful to predict prognosis of patients with higher risk prostate cancer who undergo immediate RPE. Presumably the test should still have some predictive power for time to relapse even in the setting of patients with higher biopsy Gleason scores and it may be able to provide additional information to physicians trying to assess how aggressive a patient's prostate cancer is prior to RPE and possibly indicate the need for additional supportive therapies.

Testing System

After a classifier for predicting indolence or aggressiveness of prostate cancer has been generated and defined as explained in Examples 1-3 (including specifying the feature table with intensity values, final classifier definition, mini-classifier parameters including filtering etc.), it is now ready for use to classify a blood-based sample from a prostate cancer patient to assign a class label for the sample as either Early (high risk of relapse/aggressive) or Late (low risk/indolence). The class label is provided to the medical practitioner ordering the test. The class label can be used to guide treatment, for example initiating more aggressive treatment if the class label is Early or the equivalent.

Figure 21:
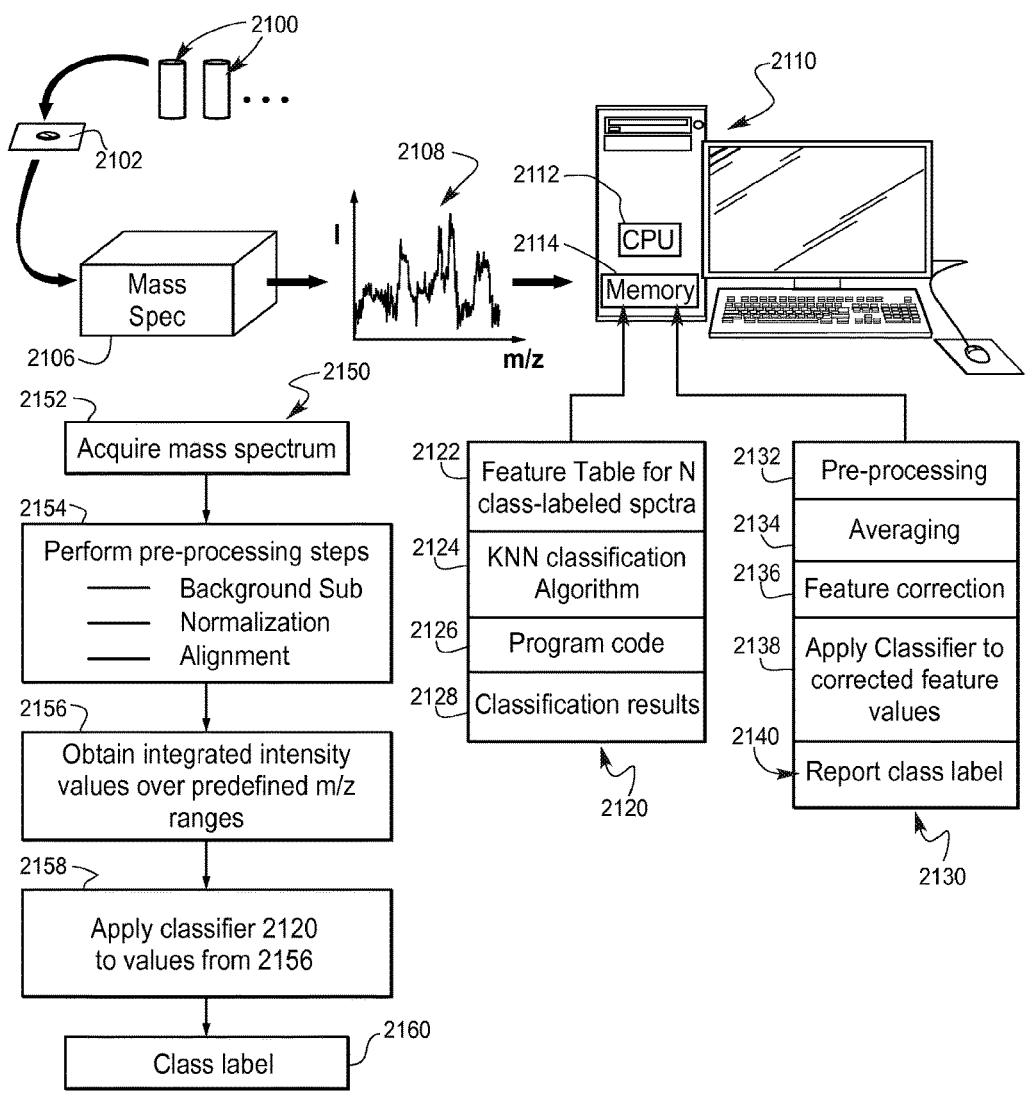
FIG. 21 is an illustration of a testing process and system for conducting a test on a blood-based sample of a prostate cancer patient to predict indolence or aggressiveness of the cancer.

FIG. 21 is an illustration of a system for processing a test sample (in this example a blood-based sample from a prostate cancer patient) using a classifier generated in accordance with FIG. 1. The system includes a mass spectrometer 2106 and a general purpose computer 2110 implementing a final classifier 2120 coded as machine-readable instructions and a constitutive mass spectral data set including a feature table 2122 of class-labeled mass spectrometry data stored in memory 2114. It will be appreciated that the mass spectrometer 2106 and computer 2110 of FIG. 21 could be used to generate the classifier in accordance with the classifier development process of FIG. 1.

The operation of the system of FIG. 21 will be described in the context of a predictive test for indolence or aggressiveness of prostate cancer as explained in the above Examples, but it will be appreciated that the methodology described in this section can be used in other examples.

The system of FIG. 21 obtains a multitude of samples 2100, e.g., blood-based samples (serum or plasma) from diverse prostate cancer patients. The samples 2100 are used by the classifier (implemented in the computer 2110) to make predictions as to whether the patient providing the sample is likely to have aggressive or indolent prostate cancer, and typically will be have just been diagnosed with "low risk" prostate cancer (TGS <7) with the physician deciding whether watchful waiting/active surveillance is an appropriate treatment protocol or maybe in an indication ready to undergo RPE and the physician may require additional prognostic information to plan additional supportive therapy post RPE. The outcome of the test is a binary class label, such as Low Risk, Low, Late, or the equivalent, or High Risk, High, Early or the equivalent, with Low or the equivalent indicating that the patient is likely to have an indolent form of the cancer and High meaning that the patient is likely to have an aggressive form of the cancer. The particularly moniker for the class label is not important and could be in accordance any binary system.

The samples may be obtained on serum cards or the like in which the blood-based sample is blotted onto a cellulose or other type card. The obtaining of the mass spectra and the pre-processing of the spectra will normally follow the methods used in generating the classifier in accordance with FIG. 1 and described in the Examples. As one possible example, in which typical "Dilute and Shoot" ~2000 shot spectra are acquired for each sample, three aliquots of the sample are obtained. The three aliquots of the sample are spotted onto a MALDI-ToF sample "plate" 2102 and the plate inserted into a MALDI-ToF mass spectrometer 2106. The mass spectrometer 2106 acquires a mass spectrum 2108 from each of the three aliquots of the sample. The mass spectra are represented in digital form and supplied to a programmed general purpose computer 2110. The computer 2110 includes a central processing unit 2112 executing programmed instructions. The memory 2114 stores the data representing the mass spectra 2108.

The memory 2114 also stores a final classifier 2120 defined as per the procedure of Figure at step 1144, which includes a) a constitutive mass spectral data set 2122 in the form of a feature table of N class-labeled spectra, where N is some integer number, in this example a development set used to develop the classifier as explained in Examples 1-3. The final classifier 2120 includes b) code 2124 representing a KNN classification algorithm (which is implemented in the mini-classifiers as explained above in FIG. 1, as well as values defining the parameters of the mini-classifiers such as features to use, etc.), c) program code 2126 for executing the final classifier generated in accordance with FIG. 1 on the mass spectra of patients, including logistic regression weights and data representing master classifier(s) forming the final classifier, and d) a data structure 2128 for storing classification results, including a final class label for the test sample. The memory 2114 also stores program code 2130 for implementing the processing shown at 2150, including code (not shown) for acquiring the mass spectral data from the mass spectrometer in step 2152; a pre-processing routine 2132 for implementing the background subtraction, normalization and alignment step 2154 (details explained above), a module (not shown) for calculating integrated intensity values at predefined m/Z positions in the background subtracted, normalized and aligned spectrum (step 2156), and a code routine 2138 for implementing the final classifier 2120 using the dataset 2122 on the values obtained at step 2156. The process 2158 produces a class label at step 2160. The module 2140 reports the class label as indicated at 2160 (i.e., "low", "Late" or the equivalent).

The program code 2130 can include additional and optional modules, for example a feature correction function code 2136 (described in co-pending U.S. patent application Ser. No. 14/486,442) for correcting fluctuations in performance of the mass spectrometer, a set of routines for processing the spectrum from a reference sample to define a feature correction function, a module storing feature dependent noise characteristics and generating noisy feature value realizations and classifying such noisy feature value realizations, modules storing statistical algorithms for obtaining statistical data on the performance of the classifier on the noisy feature value realizations, or modules to combine class labels defined from multiple individual replicate testing of a sample to produce a single class label for that sample. Still other optional software modules could be included as will be apparent to persons skilled in the art.

The system of FIG. 21 can be implemented as a laboratory test processing center obtaining a multitude of patient samples from oncologists, patients, clinics, etc., and generating a class label for the patient samples as a fee-for-service. The mass spectrometer 2106 need not be physically located at the laboratory test center but rather the computer 2110 could obtain the data representing the mass spectra of the test sample over a computer network.

Further Considerations:

Deep-MALDI Spectra

As explained in Example 3, it is possible to obtain much more spectral information from the samples used in generation of the classifier using the techniques termed "Deep-MALDI" described in the pending application of Roder et al., Ser. No. 13/836,436 filed Mar. 15, 2013, the content of which is incorporated by reference herein. In that technique, more than 100,000 laser shots, and potentially hundreds of thousands or even millions of laser shots, are applied to the MALDI plate spot containing the sample (or as a sum from shots on several such MALDI plate spots). This technique produces a vastly increased amount of spectral information than obtained from typical 2,000 shot "dilute and shoot" spectra. If this technique is used, during the classifier development process there may be many dozens, if not hundreds or even thousands of potential m/z features which can be used for classifier generation. All of these features may be used for classifier development, or a statistical analysis of the features may be performed to identify those features that are most discriminatory or differentially expressed in the Low and High risk patients. If Deep MALDI is used for generating the classifier then the same procedures are used for obtaining spectral data from the sample under test. For example, the methods described in Example 3 are used in both classifier generation and in the testing environment at FIG. 21, step 2150, and in the pre-processing steps 2154.

Reselection of Feature Values During Iterative Development of the Classifier

We have found from other exercises of classifier development using the procedure of FIG. 1 that when we have a feature space with a large number of features (typically hundreds or even thousands, as is often the case particular when you use Deep MALDI) and where there is some inherent ambiguity or uncertainty in the initial definition of the class labels during classifier development (as here), it can be advantageous to not only perform label flipping during iterations of the classifier development process of FIG. 1 (step 1140) but also at the same time use the new class label groupings to reselect features from the available feature space for classification (again, using the statistical methods for feature selection). This technique is explained in some detail in the related U.S. application Ser. No. 14/486,442 filed Sep. 15, 2014. In essence, and with reference to FIG. 1, when the loop 1142 is entered and new groupings defined at the new iteration of step 1102, at the same time new features are selected in the feature space of available mass spectrometry features using statistical analysis of the features for each of the group labels in the development set. Then, in the subsequent iteration of the step 1120 the mini-classifiers are constructed and executed using the redefined group labels and new features. Repeated iteration of this process tends to converge on a generalizable and unique definition of both group labels and classification features.

m/z Features

Note that, in the above classifier development process and in applying a final classifier to a test sample, we have not found it necessary to correlate the m/z features we use for classification to particular proteins or biomarkers circulating in blood. The validity of the classifier is established by whether it works or not and whether it is generalizable to new samples. The methods we have described demonstrate that the classifier works and is generalizable.

Constitutive Set for Classification of Test Samples

Once the classifier generation process of FIG. 1 is followed and a final classifier defined for future testing, the data set of class-labeled spectra used in generating the classifier (and in particular a feature table of intensity values at particular m/z ranges) is stored and then used as a reference set for classification using the testing procedure of FIG. 21. As noted, this "constitutive set" of spectra is obtained from blood-based samples of humans diagnosed with prostate cancer and includes patients both with indolent cancer and with aggressive cancer. This constitutive set can consist of spectra from all of the samples in a classifier development sample set (1100) or some subset thereof.

The appended claims are offered as further descriptions of the disclosed inventions.

Appendices

Example 1 Appendix A: Feature Definitions Used in New Classifier Development for Prostate Cancer

All feature definitions

| Left m/z | Center m/z | Right m/z |
|---|---|---|
| 3081.583 | 3090.249 | 3098.915 |
| 3308.621 | 3329.648 | 3350.675 |
| 4145.045 | 4160.911 | 4176.776 |
| 4177.923 | 4197.23 | 4216.536 |
| 4446.822 | 4468.04 | 4489.258 |
| 4556.927 | 4572.41 | 4587.894 |
| 4694.939 | 4717.304 | 4739.669 |
| 4772.094 | 4790.636 | 4809.178 |
| 4809.56 | 4824.661 | 4839.762 |
| 4846.644 | 4860.598 | 4874.552 |
| 4880.493 | 4896.55 | 4912.607 |
| 5053.678 | 5071.264 | 5088.85 |
| 5090.762 | 5109.303 | 5127.845 |
| 5279.182 | 5292.874 | 5306.565 |
| 6376.924 | 6430.949 | 6484.973 |
| 6576.342 | 6590.984 | 6605.625 |
| 6606.408 | 6652.759 | 6699.111 |
| 6782.803 | 6797.117 | 6811.43 |
| 6822.441 | 6835.653 | 6848.866 |
| 6849.6 | 6859.632 | 6869.663 |
| 6870.397 | 6891.073 | 6911.748 |
| 6928.141 | 6946.736 | 6965.332 |
| 7018.671 | 7055.25 | 7091.829 |
| 7370.816 | 7387.447 | 7404.077 |
| 7405.224 | 7419.56 | 7433.897 |
| 7514.946 | 7556.617 | 7598.289 |
| 7658.311 | 7681.058 | 7703.805 |
| 7893.703 | 7945.124 | 7996.544 |
| 7999.22 | 8034.583 | 8069.947 |
| 8181.751 | 8209.468 | 8237.185 |
| 8551.43 | 8562.293 | 8573.157 |
| 8574.723 | 8589.795 | 8604.867 |
| 8666.721 | 8691.776 | 8716.831 |

| | | |
|---|---|---|
| 8730.019 | 8759.869 | 8789.72 |
| 8792.411 | 8818.347 | 8844.283 |
| 8859.941 | 8870.798 | 8881.656 |
| 8883.796 | 8923.25 | 8962.704 |
| 9043.529 | 9067.232 | 9090.935 |
| 9092.465 | 9154.245 | 9216.026 |
| 9265.334 | 9282.308 | 9299.283 |
| 9324.362 | 9346.077 | 9367.792 |
| 9368.098 | 9381.861 | 9395.624 |
| 9398.071 | 9433.855 | 9469.639 |
| 9471.168 | 9487.836 | 9504.505 |
| 9617.762 | 9641.159 | 9664.556 |
| 9690.553 | 9717.467 | 9744.382 |
| 9777.537 | 9793.747 | 9809.957 |
| 9902.628 | 9935.506 | 9968.385 |
| 10325.87 | 10347.13 | 10368.38 |
| 10430.11 | 10453.51 | 10476.9 |
| 11502.59 | 11525.29 | 11547.99 |
| 11642.19 | 11673.55 | 11704.91 |
| 11709.09 | 11730.3 | 11751.51 |
| 12525.06 | 12571.66 | 12618.25 |
| 12808.63 | 12864.18 | 12919.74 |
| 13676.71 | 13706.17 | 13735.63 |
| 13737.77 | 13758.42 | 13779.07 |
| 13781.02 | 13797.76 | 13814.5 |
| 13825.46 | 13839.55 | 13853.64 |
| 13855.09 | 13877.11 | 13899.13 |
| 13899.72 | 13913.81 | 13927.91 |
| 13928.52 | 13939.29 | 13950.05 |
| 13958.08 | 13970.19 | 13982.3 |
| 14026.12 | 14041.39 | 14056.66 |
| 14056.69 | 14066.96 | 14077.23 |
| 14612.46 | 14676.26 | 14740.06 |
| 15010.07 | 15126.44 | 15242.8 |
| 15269.09 | 15291.55 | 15314.01 |
| 15315.44 | 15345.55 | 15375.65 |
| 15724.22 | 15852.06 | 15979.89 |
| 16008.09 | 16031.26 | 16054.44 |
| 16056.83 | 16093.15 | 16129.47 |
| 16605.01 | 16682.66 | 16760.32 |
| 17091.97 | 17138.56 | 17185.16 |
| 17223.02 | 17266.27 | 17309.52 |

| | | |
|---|---|---|
| 17333.41 | 17393.86 | 17454.31 |
| 17563.93 | 17601.92 | 17639.91 |
| 18598.12 | 18640.3 | 18682.49 |
| 21007.96 | 21074.42 | 21140.87 |
| 21949.42 | 22238.76 | 22528.1 |
| 27742.59 | 27978.55 | 28214.5 |
| 28227.94 | 28314.56 | 28401.17 |
| 28793.87 | 28909.23 | 29024.6 |
| 29572.29 | 29667.12 | 29761.95 |

Example 1 Appendix B: Samples from the Oregon Prostate Cancer data set used in Classifier Development

Samples used in the Classifier Development and clinical data available

| Patient ID | Primary Gleason Score | Secondary Gleason Score | Total Gleason Score |
|---|---|---|---|
| 2 | 3 | 3 | 6 |
| 3 | 3 | 3 | 6 |
| 9 | 3 | 3 | 6 |
| 10 | 3 | 3 | 6 |
| 15 | 3 | 3 | 6 |
| 18 | 3 | 3 | 6 |
| 19 | 3 | 3 | 6 |
| 20 | 3 | 3 | 6 |
| 21 | 3 | 3 | 6 |
| 26 | 3 | 3 | 6 |
| 29 | 3 | 3 | 6 |
| 32 | 3 | 3 | 6 |
| 22--EB | 3 | 3 | 6 |
| N--04--1 | 3 | 3 | 6 |
| N--06--0 | 3 | 3 | 6 |
| N--15--0 | 3 | 3 | 6 |
| N--18--0 | 3 | 3 | 6 |
| OET | 3 | 3 | 6 |
| 5 | 3 | 4 | 7 |
| 6 | 3 | 4 | 7 |
| 7 | 3 | 4 | 7 |
| 11 | 3 | 4 | 7 |
| 13 | 3 | 4 | 7 |
| 14 | 3 | 4 | 7 |

| | | | |
|---|---|---|---|
| 16 | 3 | 4 | 7 |
| 17 | 3 | 4 | 7 |
| 25 | 3 | 4 | 7 |
| 27 | 3 | 4 | 7 |
| 13 --WFG | 3 | 4 | 7 |
| N--07--0 | 3 | 4 | 7 |
| N--08--0 | 3 | 4 | 7 |
| N--19--1 | 3 | 4 | 7 |
| N--22--0 | 3 | 4 | 7 |
| N--27--0 | 3 | 4 | 7 |
| N--31--1 | 3 | 4 | 7 |
| N--39--1 | 3 | 4 | 7 |
| UW-01 | 3 | 4 | 7 |
| UW-12 | 3 | 4 | 7 |
| KP-02 | 4 | 3 | 7 |
| KP-03 | 4 | 3 | 7 |
| KP-04 | 4 | 3 | 7 |
| N--03--0 | 4 | 3 | 7 |
| N--23--0 | 4 | 3 | 7 |
| UW-09 | 4 | 3 | 7 |
| UW-10 | 4 | 3 | 7 |
| UW-11 | 4 | 3 | 7 |
| 8 | 4 | 4 | 8 |
| 33 | 4 | 4 | 8 |
| N--01--0 | 4 | 4 | 8 |
| N--02--0 | 4 | 4 | 8 |
| N--10--0 | 5 | 3 | 8 |
| N--13--1 | 4 | 4 | 8 |
| N--16--1 | 4 | 4 | 8 |
| N--21--0 | 4 | 4 | 8 |
| N--24--0 | 4 | 4 | 8 |
| N--32--1 | 4 | 4 | 8 |
| N--35--1 | 4 | 4 | 8 |
| N--36--1 | 3 | 5 | 8 |
| UW-06 | 5 | 3 | 8 |
| UW-08 | 4 | 4 | 8 |
| UW-16 | 4 | 4 | 8 |
| UW-17 | 4 | 4 | 8 |
| 1 | 4 | 5 | 9 |
| 23 | 4 | 5 | 9 |
| N--11--0 | 4 | 5 | 9 |
| N--14--1 | 4 | 5 | 9 |
| N--25--0 | 4 | 5 | 9 |

| | | | |
|---|---|---|---|
| N--28--0 | 4 | 5 | 9 |
| N--34--0 | 4 | 5 | 9 |
| N--5--1 | 5 | 4 | 9 |
| UW-03 | 4 | 5 | 9 |
| UW-07 | 4 | 5 | 9 |
| UW-13 | 4 | 5 | 9 |
| UW-18 | 4 | 5 | 9 |
| KP-05 | 5 | 5 | 10 |

Example 1 Appendix C: MMV labels attributed to each patient after 3 label flips

Risk levels as defined in Table 1 are also included.

| Patient ID | Final MMV Label | Definition (as in Table 1) |
|---|---|---|
| 1 | High | High |
| 10 | Low | Low |
| 11 | High | Int |
| 13 | Low | Int |
| 13-WFG | Low | Int |
| 14 | Low | Int |
| 15 | High | Low |
| 16 | Low | Int |
| 17 | Low | Int |
| 18 | Low | Low |
| 19 | Low | Low |
| 2 | High | Low |
| 20 | High | Low |
| 21 | Low | Low |
| 22-EB | Low | Low |
| 23 | High | High |
| 25 | Low | Int |
| 26 | Low | Low |
| 27 | High | Int |
| 29 | High | Low |
| 3 | High | Low |
| 32 | High | Low |
| 33 | High | High |
| 5 | Low | Int |
| 6 | Low | Int |
| 7 | High | Int |

|  |  |  |
|---|---|---|
| 8 | High | High |
| 9 | Low | Low |
| KP-02 | High | Int |
| KP-03 | High | Int |
| KP-04 | Low | Int |
| KP-05 | Low | High |
| N-01-0 | Low | High |
| N-02-0 | High | High |
| N-03-0 | Low | Int |
| N-04-1 | High | Low |
| N-06-0 | Low | Low |
| N-07-0 | High | Int |
| N-08-0 | Low | Int |
| N-10-0 | Low | High |
| N-11-0 | Low | High |
| N-13-1 | Low | High |
| N-14-1 | Low | High |
| N-15-0 | Low | Low |
| N-16-1 | High | High |
| N-18-0 | High | Low |
| N-19-1 | Low | Int |
| N-21-0 | High | High |
| N-22-0 | High | Int |
| N-23-0 | Low | Int |
| N-24-0 | High | High |
| N-25-0 | High | High |
| N-27-0 | High | Int |
| N-28-0 | Low | High |
| N-31-1 | High | Int |
| N-32-1 | High | High |
| N-34-1 | High | High |
| N-35-1 | High | High |
| N-36-1 | High | High |
| N-39-1 | High | Int |
| N-5-1 | Low | High |
| OET | Low | Low |
| UW-01 | Low | Int |
| UW-03 | High | High |
| UW-06 | High | High |
| UW-07 | Low | High |
| UW-08 | Low | High |
| UW-09 | High | Int |
| UW-10 | High | Int |

| | | |
|---|---|---|
| UW-11 | Low | Int |
| UW-12 | Low | Int |
| UW-13 | High | High |
| UW-16 | High | High |
| UW-17 | High | High |
| UW-18 | High | High |

Example 2 appendices

Appendix A: Feature Definitions Used in New Classifier Development for Prostate Cancer

All feature definitions

| Left m/z | Center m/z | Right m/z |
|---|---|---|
| 3153.208 | 3164.868 | 3176.529 |
| 3353.837 | 3372.531 | 3391.224 |
| 3419.727 | 3442.492 | 3465.257 |
| 3473.03 | 3490.798 | 3508.566 |
| 4055.23 | 4068.741 | 4082.252 |
| 4137.036 | 4153.693 | 4170.351 |
| 4170.721 | 4190.155 | 4209.588 |
| 4698.8 | 4712.168 | 4725.537 |
| 4759.221 | 4802.16 | 4845.099 |
| 4983.911 | 5008.526 | 5033.142 |
| 5053.501 | 5069.418 | 5085.336 |
| 5090.443 | 5104.695 | 5118.946 |
| 5121.167 | 5133.938 | 5146.708 |
| 5525.044 | 5570.204 | 5615.365 |
| 5843.444 | 5879.72 | 5915.996 |
| 5978.924 | 6000.949 | 6022.974 |
| 6366.989 | 6387.348 | 6407.707 |
| 6409.047 | 6457.28 | 6505.514 |
| 6518.615 | 6532 | 6545.385 |
| 6623.863 | 6631.566 | 6639.268 |
| 6566.766 | 6632.507 | 6698.248 |
| 6785.31 | 6794.313 | 6803.315 |
| 6826.591 | 6838.081 | 6849.57 |
| 6850.447 | 6859.449 | 6868.452 |
| 6870.181 | 6882.263 | 6894.346 |

| | | |
|---|---|---|
| 6916.615 | 6940.779 | 6964.943 |
| 7459.185 | 7488.68 | 7518.175 |
| 7526.229 | 7562.357 | 7598.486 |
| 7601.624 | 7617.379 | 7633.133 |
| 7657.771 | 7674.354 | 7690.938 |
| 7887.538 | 7929.737 | 7971.936 |
| 7976.674 | 7990.148 | 8003.622 |
| 8005.695 | 8033.827 | 8061.96 |
| 8188.822 | 8205.257 | 8221.693 |
| 8226.727 | 8238.276 | 8249.825 |
| 8651.726 | 8684.856 | 8717.985 |
| 8726.499 | 8759.074 | 8791.648 |
| 8797.941 | 8827.554 | 8857.167 |
| 8887.061 | 8931.11 | 8975.16 |
| 9041.789 | 9061.223 | 9080.657 |
| 9084.787 | 9147.53 | 9210.273 |
| 9281.714 | 9303.369 | 9325.024 |
| 9329.466 | 9346.308 | 9363.151 |
| 9366.482 | 9382.584 | 9398.686 |
| 9400.788 | 9437.805 | 9474.821 |
| 9623.278 | 9643.606 | 9663.934 |
| 9693.159 | 9709.261 | 9725.363 |
| 9727.954 | 9747.388 | 9766.821 |
| 9917.122 | 9933.965 | 9950.807 |
| 10045.12 | 10073.81 | 10102.5 |
| 10130.62 | 10227.42 | 10324.21 |
| 10326.06 | 10342.54 | 10359.01 |
| 10409.79 | 10460.69 | 10511.59 |
| 10610.05 | 10649.29 | 10688.53 |
| 10778.11 | 10838.26 | 10898.41 |
| 11501.77 | 11535.78 | 11569.79 |
| 11653.08 | 11680.38 | 11707.67 |
| 11713.23 | 11736.36 | 11759.5 |
| 12524.61 | 12570.59 | 12616.58 |
| 12768.69 | 12848.51 | 12928.32 |
| 13256.1 | 13278.08 | 13300.06 |
| 13490.6 | 13556.3 | 13622.01 |
| 13660.37 | 13699.01 | 13737.65 |
| 13740.89 | 13760.09 | 13779.29 |
| 13781.6 | 13794.79 | 13807.98 |
| 13825.56 | 13840.37 | 13855.17 |
| 13857.95 | 13878.31 | 13898.67 |
| 13901.91 | 13915.09 | 13928.28 |

| | | |
|---|---|---|
| 13928.74 | 13942.62 | 13956.51 |
| 13960.21 | 13979.18 | 13998.15 |
| 14020.82 | 14048.12 | 14075.42 |
| 14078.2 | 14103.42 | 14128.63 |
| 14130.48 | 14156.63 | 14182.77 |
| 14339.49 | 14402.65 | 14465.81 |
| 14830.89 | 14885.25 | 14939.62 |
| 14941.47 | 14989.6 | 15037.72 |
| 15039.57 | 15067.33 | 15095.09 |
| 15096.02 | 15155.01 | 15214.01 |
| 15270.23 | 15291.74 | 15313.26 |
| 15314.65 | 15346.57 | 15378.5 |
| 15705.12 | 15736.59 | 15768.05 |
| 15769.44 | 15801.13 | 15832.83 |
| 15833.76 | 15867.07 | 15900.39 |
| 15901.31 | 15925.14 | 15948.97 |
| 15951.75 | 15981.59 | 16011.43 |
| 16014.21 | 16034.34 | 16054.47 |
| 16055.85 | 16088.94 | 16122.02 |
| 16125.23 | 16148 | 16170.78 |
| 16175.11 | 16204.76 | 16234.4 |
| 16600.22 | 16666.38 | 16732.53 |
| 17222.34 | 17246.92 | 17271.5 |
| 17272.23 | 17288.13 | 17304.04 |
| 17358.26 | 17377.42 | 17396.58 |
| 17398.03 | 17417.91 | 17437.79 |
| 17852.61 | 17901.41 | 17950.21 |
| 18594.98 | 18622.82 | 18650.65 |
| 18652.82 | 18677.4 | 18701.98 |
| 20902.69 | 20954.66 | 21006.62 |
| 21011.14 | 21064.46 | 21117.78 |
| 23258.31 | 23571.9 | 23885.49 |
| 27660.21 | 27839.26 | 28018.31 |
| 28019.44 | 28098.51 | 28177.59 |
| 28227.29 | 28315.97 | 28404.65 |
| 28815.5 | 28888.93 | 28962.36 |

Example 2

Appendix B: Samples from the Oregon Prostate Cancer data set used in Classifier Development

Samples used in the Classifier development and clinical data available

| PatientID | Code | TGS | PSA baseline | TimeToProgression [days] | Censor | Set |
|---|---|---|---|---|---|---|
| WW001354 | 8 | 7 | 4.69 | 714 | 0 | Development |
| WW001537 | 99 | 6 | 5.85 | 824 | 1 | Development |
| WW001578 | 8 | 6 | 10.43 | 83 | 0 | Development |
| WW001636 | 99 | Unknown | 3.75 | 985 | 1 | Development |
| WW001826 | 99 | 6 | 19.88 | 207 | 1 | Development |
| WW001883 | 8 | 5 | Unknown | 1325 | 0 | Development |
| WW001990 | 99 | 7 | Unknown | 1279 | 1 | Development |
| WW002048 | 99 | 6 | Unknown | 644 | 1 | Development |
| WW002055 | 99 | 3 | Unknown | 917 | 1 | Development |
| WW002063 | 8 | 6 | Unknown | 412 | 0 | Development |
| WW002089 | 99 | 6 | Unknown | 99 | 1 | Development |
| WW002097 | 99 | 5 | Unknown | 810 | 1 | Development |
| WW040139 | 8 | 6 | 8.11 | 1918 | 0 | Development |
| WW040220 | 8 | 6 | 6.6 | 1286 | 0 | Development |
| WW040238 | 8 | 6 | 6.3 | 1106 | 0 | Development |
| WW040261 | 8 | 6 | 6.7 | 1895 | 0 | Development |
| WW040295 | 8 | 5 | 1 | 91 | 0 | Development |
| WW040303 | 8 | 6 | 9.2 | 1726 | 0 | Development |
| WW040311 | 8 | 6 | 7.9 | 1820 | 0 | Development |
| WW040360 | 8 | 6 | 14.1 | 165 | 0 | Development |
| WW040386 | 8 | 6 | 10 | 1650 | 0 | Development |
| WW040444 | 99 | 6 | 4.4 | 350 | 1 | Development |
| WW040451 | 99 | 6 | 8.6 | 986 | 1 | Development |
| WW040469 | 99 | 6 | Unknown | 461 | 1 | Development |
| WW040527 | 8 | 4 | 8.6 | 1701 | 0 | Development |
| WW040543 | 8 | 7 | 3.1 | 1705 | 0 | Development |
| WW040550 | 99 | 6 | 24.8 | 889 | 1 | Development |
| WW040683 | 99 | 3 | 5.5 | 769 | 1 | Development |
| WW040709 | 8 | 6 | 3.1 | 1509 | 0 | Development |
| WW040717 | 99 | 6 | 10.5 | 1210 | 1 | Development |
| WW040790 | 8 | 6 | 11.5 | 1432 | 0 | Development |
| WW040873 | 8 | 6 | 4.1 | 1363 | 0 | Development |

| WW040899 | 99 | 6 | 9.1 | 455 | 1 | Development |
| --- | --- | --- | --- | --- | --- | --- |
| WW040907 | 99 | 6 | 1.7 | 355 | 1 | Development |
| WW040931 | 8 | 5 | 7.8 | 362 | 0 | Development |
| WW040980 | 99 | 6 | 6 | 1013 | 1 | Development |
| WW041020 | 8 | 6 | 4.7 | 1098 | 0 | Development |
| WW041046 | 8 | 6 | 8.8 | 90 | 0 | Development |
| WW041053 | 99 | 6 | 5.4 | 909 | 1 | Development |
| WW041145 | 8 | 6 | 4 | 96 | 0 | Development |
| WW041194 | 8 | 5 | 0.4 | 912 | 0 | Development |
| WW001180 | 99 | 6 | 26.6 | 609 | 1 | Development |
| WW001198 | 99 | 6 | 13.82 | 581 | 1 | Development |
| WW001313 | 99 | 7 | 12.68 | 512 | 1 | Development |
| WW001438 | 8 | 5 | 9.7 | 447 | 0 | Development |
| WW001495 | 99 | 6 | 7.5 | 1365 | 1 | Development |
| WW001958 | 8 | 6 | Unknown | 1573 | 0 | Development |
| WW001966 | 8 | 6 | Unknown | 560 | 0 | Development |
| WW040030 | 99 | 6 | 18.6 | 176 | 1 | Development |
| WW040758 | 8 | 6 | 8.2 | 275 | 0 | Development |
| WW001016 | 90 | 5 | 2.75 | 1813 | 0 | Development |
| WW001131 | 90 | 6 | 15.36 | 1723 | 0 | Development |
| WW001719 | 90 | 5 | 8.14 | 1825 | 0 | Development |
| WW001727 | 90 | 6 | 8.8 | 1638 | 0 | Development |
| WW001909 | 90 | 6 | 0.5 | 1840 | 0 | Development |
| WW001982 | 90 | 4 | Unknown | 1832 | 0 | Development |
| WW002014 | 90 | 4 | Unknown | 1819 | 0 | Development |
| WW002071 | 90 | 5 | Unknown | 1807 | 0 | Development |
| WW040014 | 90 | 6 | 1.35 | 1714 | 0 | Development |
| WW040097 | 90 | 5 | 6.93 | 2010 | 0 | Development |
| WW040345 | 8 | 6 | 6.2 | 1826 | 0 | Development |
| WW001115 | 8 | 6 | 10.21 | 1018 | 0 | Development |
| WW001214 | 8 | 6 | 8.92 | 801 | 0 | Development |
| WW001222 | 8 | 6 | 15.06 | 761 | 0 | Development |
| WW001230 | 8 | 5 | 9.11 | 71 | 0 | Development |
| WW001255 | 90 | 4 | 9.29 | 1736 | 0 | Development |
| WW001339 | 8 | 6 | 6.96 | 506 | 0 | Development |
| WW001396 | 90 | 6 | 7.33 | 1911 | 0 | Development |
| WW001404 | 8 | 3 | 1.84 | 490 | 0 | Development |
| WW001446 | 90 | 5 | 10.13 | 1818 | 0 | Development |
| WW001487 | 90 | 6 | 2.8 | 1897 | 0 | Development |
| WW001503 | 8 | 7 | 8.89 | 303 | 0 | Development |
| WW001545 | 8 | Unknown | 2.12 | 1553 | 0 | Development |
| WW001586 | 90 | 6 | 8.32 | 1817 | 0 | Development |
| WW001594 | 8 | 6 | 4.71 | 1204 | 0 | Development |

| | | | | | | |
|---|---|---|---|---|---|---|
| WW001701 | 90 | 6 | 4.31 | 1748 | 0 | Development |
| WW001735 | 90 | 6 | 10.48 | 1839 | 0 | Development |
| WW001768 | 90 | 6 | 8.07 | 1900 | 0 | Development |
| WW001792 | 90 | 6 | 4.28 | 1871 | 0 | Development |
| WW001875 | 90 | 4 | 0.76 | 1827 | 0 | Development |
| WW002105 | 90 | 4 | Unknown | 1846 | 0 | Development |
| WW040022 | 90 | 6 | 11.4 | 1826 | 0 | Development |
| WW040048 | 8 | 6 | 5.34 | 1034 | 0 | Development |
| WW040188 | 8 | 6 | 25.7 | 295 | 0 | Development |
| WW040352 | 8 | 7 | 9.2 | 1367 | 0 | Development |
| WW040436 | 8 | 7 | 5.4 | 1722 | 0 | Development |
| WW040634 | 8 | 6 | 0.5 | 1672 | 0 | Development |
| WW040642 | 8 | 5 | 8.3 | 1469 | 0 | Development |
| WW040667 | 8 | 6 | 4.9 | 999 | 0 | Development |
| WW040725 | 8 | 7 | 9.1 | 1461 | 0 | Development |
| WW001800 | 8 | 5 | 2.98 | 91 | 0 | Validation |
| WW001842 | 8 | 5 | 3.41 | 442 | 0 | Validation |
| WW002006 | 8 | 5 | Unknown | 119 | 0 | Validation |
| WW002030 | 8 | 5 | Unknown | 507 | 0 | Validation |
| WW002113 | 8 | 6 | 13.9 | 1654 | 0 | Validation |
| WW040055 | 8 | 4 | 2.26 | 1981 | 0 | Validation |
| WW040121 | 8 | 6 | 8.67 | 364 | 0 | Validation |
| WW040170 | 8 | 6 | 12.8 | 909 | 0 | Validation |
| WW040246 | 8 | 6 | 16.3 | 1728 | 0 | Validation |
| WW040287 | 8 | 5 | 4.4 | 1872 | 0 | Validation |
| WW040337 | 8 | 6 | 6.6 | 1848 | 0 | Validation |
| WW040378 | 8 | 6 | 5.4 | 555 | 0 | Validation |
| WW040493 | 8 | 7 | 15.1 | 1715 | 0 | Validation |
| WW040501 | 8 | 7 | 12.1 | 761 | 0 | Validation |
| WW040519 | 8 | 6 | 15.2 | 1716 | 0 | Validation |
| WW040659 | 8 | 6 | 4.5 | 1597 | 0 | Validation |
| WW040691 | 8 | 6 | 5.3 | 1286 | 0 | Validation |
| WW040733 | 8 | Unknown | 6.1 | 629 | 0 | Validation |
| WW040741 | 8 | 6 | 3.7 | 652 | 0 | Validation |
| WW040816 | 8 | 7 | 5.9 | 1426 | 0 | Validation |
| WW040915 | 8 | 6 | 1.1 | 1363 | 0 | Validation |
| WW040949 | 8 | 6 | 1.8 | 292 | 0 | Validation |
| WW040972 | 8 | 6 | 13.4 | 95 | 0 | Validation |
| WW041103 | 8 | 6 | 6.1 | 186 | 0 | Validation |
| WW041129 | 8 | 4 | 1.2 | 93 | 0 | Validation |
| WW041152 | 8 | 6 | 6.5 | 97 | 0 | Validation |
| WW041186 | 8 | 6 | 4.3 | 1096 | 0 | Validation |
| WW001321 | 8 | 6 | 6.74 | 1485 | 0 | Validation |

| | | | | | | |
|---|---|---|---|---|---|---|
| WW001420 | 8 | 6 | 9.81 | 763 | 0 | Validation |
| WW001511 | 8 | 5 | 11.29 | 1406 | 0 | Validation |
| WW001644 | 8 | 6 | 19.47 | 476 | 0 | Validation |
| WW001677 | 8 | 6 | 6.17 | 1825 | 0 | Validation |
| WW001859 | 8 | 7 | 3.5 | 1658 | 0 | Validation |
| WW001917 | 8 | 6 | Unknown | 1099 | 0 | Validation |
| WW001974 | 8 | 3 | Unknown | 368 | 0 | Validation |
| WW040105 | 8 | 6 | 7.1 | 1903 | 0 | Validation |
| WW040147 | 8 | 6 | 7.12 | 87 | 0 | Validation |
| WW040162 | 8 | 6 | 4.68 | 1967 | 0 | Validation |
| WW040600 | 8 | 6 | 5 | 1003 | 0 | Validation |
| WW040618 | 8 | 6 | 19.1 | 1568 | 0 | Validation |
| WW040675 | 8 | 7 | 5.5 | 442 | 0 | Validation |
| WW040824 | 8 | 7 | 3 | 1281 | 0 | Validation |
| WW040832 | 8 | 6 | 3.3 | 1279 | 0 | Validation |
| WW041038 | 8 | 5 | 5.8 | 1181 | 0 | Validation |
| WW041095 | 8 | 6 | 0.8 | 1197 | 0 | Validation |
| WW041160 | 8 | 6 | 7.1 | 1026 | 0 | Validation |

Example 3

Appendix A: Feature Definitions

Table A.1 Feature definitions n=329

| Left | Center | Right |
|---|---|---|
| 3073.625 | 3085.665 | 3097.705 |
| 3098.586 | 3109.891 | 3121.197 |
| 3123.546 | 3138.669 | 3153.793 |
| 3190.793 | 3210.615 | 3230.436 |
| 3230.73 | 3242.623 | 3254.516 |
| 3255.103 | 3264.647 | 3274.191 |
| 3296.802 | 3316.77 | 3336.739 |
| 3349.072 | 3363.608 | 3378.144 |
| 3380.2 | 3391.946 | 3403.692 |
| 3405.16 | 3420.283 | 3435.407 |
| 3435.7 | 3445.097 | 3454.494 |
| 3454.788 | 3465.359 | 3475.931 |
| 3490.725 | 3508.305 | 3525.884 |
| 3531.431 | 3553.896 | 3576.36 |
| 3581.059 | 3593.099 | 3605.138 |
| 3665.631 | 3679.286 | 3692.941 |
| 3693.94 | 3712.036 | 3730.132 |
| 3745.211 | 3754.755 | 3764.299 |
| 3764.592 | 3775.604 | 3786.616 |
| 3798.592 | 3814.263 | 3829.933 |
| 3831.545 | 3841.53 | 3851.514 |
| 3876.474 | 3887.486 | 3898.499 |
| 3898.583 | 3906.18 | 3913.777 |
| 3914.356 | 3928.158 | 3941.959 |
| 3942.253 | 3953.412 | 3964.571 |
| 3994.23 | 4008.619 | 4023.008 |
| 4024.182 | 4031.67 | 4039.159 |
| 4039.452 | 4050.464 | 4061.476 |
| 4086.437 | 4098.77 | 4111.104 |
| 4111.308 | 4118.525 | 4125.742 |
| 4126.043 | 4133.109 | 4140.176 |
| 4198.812 | 4209.788 | 4220.764 |
| 4241.573 | 4249.445 | 4257.316 |
| 4258.28 | 4265.83 | 4273.38 |
| 4273.837 | 4286.166 | 4298.495 |
| 4328.264 | 4340.217 | 4352.17 |
| 4352.32 | 4360.815 | 4369.31 |
| 4369.611 | 4380.962 | 4392.314 |
| 4393.817 | 4408.627 | 4423.436 |
| 4424.789 | 4431.179 | 4437.569 |
| 4437.87 | 4459.22 | 4480.57 |
| 4496.507 | 4506.58 | 4516.654 |
| 4552.738 | 4564.991 | 4577.245 |
| 4577.384 | 4592.602 | 4607.819 |
| 4616.938 | 4625.282 | 4633.627 |
| 4633.927 | 4643.324 | 4652.721 |
| 4664.148 | 4675.274 | 4686.4 |
| 4690.609 | 4717.673 | 4744.736 |
| 4746.54 | 4756.162 | 4765.785 |
| 4766.386 | 4773.152 | 4779.918 |
| 4780.218 | 4791.194 | 4802.17 |
| 4802.621 | 4817.881 | 4833.142 |
| 4836.299 | 4855.995 | 4875.691 |
| 4880.953 | 4891.177 | 4901.401 |
| 4909.52 | 4918.316 | 4927.111 |
| 4927.261 | 4937.636 | 4948.01 |
| 4948.16 | 4963.045 | 4977.93 |
| 4987.552 | 4998.979 | 5010.405 |
| 5011.007 | 5020.103 | 5029.199 |
| 5029.65 | 5041.077 | 5052.504 |
| 5053.556 | 5067.839 | 5082.123 |
| 5087.535 | 5104.074 | 5120.613 |
| 5121.383 | 5134.355 | 5147.326 |
| 5149.837 | 5156.322 | 5162.808 |
| 5164.9 | 5181.637 | 5198.375 |
| 5209.77 | 5223.753 | 5237.736 |
| 5238.036 | 5247.734 | 5257.432 |

| | | |
|---|---|---|
| 5275.624 | 5289.757 | 5303.89 |
| 5347.191 | 5358.543 | 5369.894 |
| 5370.646 | 5377.186 | 5383.726 |
| 5383.877 | 5389.815 | 5395.754 |
| 5395.905 | 5403.422 | 5410.94 |
| 5411.09 | 5416.277 | 5421.464 |
| 5421.615 | 5429.809 | 5438.003 |
| 5439.807 | 5449.204 | 5458.601 |
| 5463.713 | 5472.057 | 5480.402 |
| 5481.454 | 5495.813 | 5510.171 |
| 5510.472 | 5521.222 | 5531.972 |
| 5535.439 | 5557.829 | 5580.219 |
| 5663.828 | 5675.387 | 5686.946 |
| 5696.097 | 5709.823 | 5723.549 |
| 5740.923 | 5748.044 | 5755.165 |
| 5756.127 | 5762.381 | 5768.636 |
| 5769.502 | 5776.671 | 5783.84 |
| 5787.496 | 5795.483 | 5803.469 |
| 5803.95 | 5815.979 | 5828.007 |
| 5828.68 | 5842.055 | 5855.431 |
| 5856.297 | 5867.218 | 5878.14 |
| 5879.39 | 5889.157 | 5898.924 |
| 5899.02 | 5910.808 | 5922.595 |
| 5924.106 | 5934.47 | 5944.834 |
| 5946.068 | 5961.861 | 5977.654 |
| 5978.694 | 5997.458 | 6016.222 |
| 6016.895 | 6026.806 | 6036.717 |
| 6052.178 | 6074.758 | 6097.337 |
| 6099.552 | 6108.597 | 6117.642 |
| 6161.136 | 6170.373 | 6179.611 |
| 6184.807 | 6192.938 | 6201.069 |
| 6201.261 | 6209.585 | 6217.908 |
| 6218.004 | 6226.039 | 6234.074 |
| 6245.993 | 6254.58 | 6263.166 |
| 6273.718 | 6283.244 | 6292.771 |
| 6292.867 | 6301.238 | 6309.61 |
| 6321.927 | 6331.742 | 6341.556 |
| 6349.371 | 6357.324 | 6365.277 |
| 6379.18 | 6386.108 | 6393.037 |
| 6393.229 | 6399.965 | 6406.7 |
| 6408.625 | 6437.829 | 6467.033 |
| 6467.129 | 6485.171 | 6503.214 |
| 6520.161 | 6531.72 | 6543.279 |
| 6548.095 | 6556.042 | 6563.989 |
| 6577.691 | 6589.431 | 6601.17 |
| 6603.961 | 6611.61 | 6619.26 |
| 6620.319 | 6634.319 | 6648.32 |
| 6648.512 | 6657.076 | 6665.64 |
| 6668.623 | 6680.651 | 6692.68 |
| 6700.438 | 6707.101 | 6713.764 |
| 6719.237 | 6731.65 | 6744.063 |
| 6744.599 | 6755.677 | 6766.754 |
| 6767.638 | 6773.171 | 6778.704 |
| 6786.982 | 6792.762 | 6798.542 |
| 6799.97 | 6808.919 | 6817.868 |
| 6824.892 | 6836.679 | 6848.467 |
| 6848.948 | 6859.629 | 6870.31 |
| 6873.797 | 6881.433 | 6889.07 |
| 6890.609 | 6897.599 | 6904.589 |
| 6914.565 | 6921.586 | 6928.606 |
| 6933.102 | 6941.477 | 6949.853 |
| 6950.469 | 6956.75 | 6963.032 |
| 6963.34 | 6970.545 | 6977.75 |
| 6978.92 | 6992.222 | 7005.524 |
| 7014.269 | 7022.06 | 7029.85 |
| 7029.912 | 7034.592 | 7039.272 |
| 7039.395 | 7045.154 | 7050.912 |
| 7067.293 | 7073.79 | 7080.287 |
| 7119.824 | 7147.228 | 7174.633 |
| 7177.589 | 7188.951 | 7200.314 |
| 7232.783 | 7257.933 | 7283.084 |
| 7292.812 | 7300.633 | 7308.454 |
| 7316.187 | 7321.946 | 7327.705 |
| 7327.772 | 7333.817 | 7339.863 |
| 7339.896 | 7346.093 | 7352.29 |
| 7352.819 | 7360.754 | 7368.688 |
| 7379.768 | 7393.009 | 7406.249 |
| 7406.3 | 7419.793 | 7433.287 |
| 7433.608 | 7447.584 | 7461.56 |
| 7463.692 | 7479.362 | 7495.032 |
| 7497.824 | 7510.356 | 7522.889 |
| 7731.041 | 7738.801 | 7746.561 |

| | | |
|---|---|---|
| 7761.341 | 7779.077 | 7796.813 |
| 7808.996 | 7828.02 | 7847.044 |
| 7849.362 | 7871.424 | 7893.485 |
| 7904.954 | 7912.836 | 7920.719 |
| 8007.424 | 8015.07 | 8022.717 |
| 8134.028 | 8157.158 | 8180.287 |
| 8195.752 | 8206.991 | 8218.23 |
| 8238.737 | 8253.917 | 8269.098 |
| 8304.472 | 8328.669 | 8352.866 |
| 8353.406 | 8363.536 | 8373.667 |
| 8380.133 | 8391.495 | 8402.857 |
| 8404.767 | 8413.388 | 8422.01 |
| 8422.133 | 8430.231 | 8438.33 |
| 8457.421 | 8464.072 | 8470.723 |
| 8470.846 | 8477.558 | 8484.271 |
| 8497.292 | 8508.651 | 8520.011 |
| 8520.544 | 8531.198 | 8541.852 |
| 8554.723 | 8564.761 | 8574.799 |
| 8575.476 | 8585.268 | 8595.06 |
| 8618.77 | 8631.702 | 8644.635 |
| 8649.87 | 8660.554 | 8671.239 |
| 8671.855 | 8696.119 | 8720.383 |
| 8720.568 | 8728.512 | 8736.456 |
| 8736.518 | 8745.817 | 8755.116 |
| 8756.348 | 8770.604 | 8784.861 |
| 8791.574 | 8796.962 | 8802.351 |
| 8802.474 | 8822.181 | 8841.887 |
| 8861.964 | 8871.848 | 8881.732 |
| 8883.826 | 8890.538 | 8897.251 |
| 8897.436 | 8901.654 | 8905.873 |
| 8905.934 | 8928.258 | 8950.582 |
| 8967.272 | 8974.415 | 8981.559 |
| 8988.149 | 8997.971 | 9007.794 |
| 9010.011 | 9020.295 | 9030.58 |
| 9030.764 | 9038.216 | 9045.668 |
| 9055.367 | 9062.134 | 9068.902 |
| 9069.184 | 9079.194 | 9089.205 |
| 9091.547 | 9097.798 | 9104.049 |
| 9115.171 | 9134.336 | 9153.501 |
| 9196.082 | 9206.437 | 9216.792 |
| 9217.991 | 9226.317 | 9234.643 |
| 9234.742 | 9244.546 | 9254.35 |
| 9254.941 | 9263.932 | 9272.924 |
| 9273.256 | 9291.73 | 9310.203 |
| 9310.761 | 9318.865 | 9326.969 |
| 9344.962 | 9359.289 | 9373.615 |
| 9387.662 | 9395.293 | 9402.923 |
| 9410.817 | 9430.014 | 9449.211 |
| 9475.524 | 9484.41 | 9493.296 |
| 9494.536 | 9504.042 | 9513.549 |
| 9520.898 | 9534.803 | 9548.707 |
| 9559.484 | 9576.179 | 9592.874 |
| 9615.006 | 9641.179 | 9667.352 |
| 9689.387 | 9720.901 | 9752.414 |
| 9784.265 | 9793.021 | 9801.777 |
| 9840.895 | 9862.594 | 9884.294 |
| 9908.49 | 9918.931 | 9929.371 |
| 9929.66 | 9941.495 | 9953.331 |
| 10002.41 | 10012.36 | 10022.32 |
| 10066.88 | 10079.24 | 10091.61 |
| 10091.7 | 10102.24 | 10112.77 |
| 10120.09 | 10135.29 | 10150.49 |
| 10150.78 | 10162.62 | 10174.45 |
| 10174.65 | 10185.23 | 10195.82 |
| 10195.91 | 10210.35 | 10224.78 |
| 10225.16 | 10236.04 | 10246.91 |
| 10250.09 | 10263.03 | 10275.97 |
| 10276.55 | 10285.11 | 10293.68 |
| 10295 | 10313.15 | 10331.3 |
| 10333.03 | 10346.26 | 10359.49 |
| 10359.69 | 10365.85 | 10372 |
| 10408.98 | 10420.87 | 10432.75 |
| 10436.76 | 10448.55 | 10460.34 |
| 10472.41 | 10480.21 | 10488.01 |
| 10488.32 | 10503.84 | 10519.36 |
| 10521.66 | 10532.67 | 10543.68 |
| 10543.99 | 10551.18 | 10558.36 |
| 10573.66 | 10589.18 | 10604.71 |
| 10615.84 | 10636.81 | 10657.79 |
| 10705.55 | 10734.07 | 10762.59 |
| 10773.07 | 10782.59 | 10792.12 |
| 10792.19 | 10804.96 | 10817.72 |

| | | | | | | |
|---|---|---|---|---|---|---|
| 10827.72 | 10846.77 | 10865.83 | | 13703.7 | 13721.07 | 13738.44 |
| 10912.98 | 10923.56 | 10934.15 | | 13740.45 | 13762.16 | 13783.88 |
| 10954.02 | 10965.58 | 10977.14 | | 13784.55 | 13798.24 | 13811.94 |
| 11035.47 | 11057.93 | 11080.38 | | 13826.64 | 13842.84 | 13859.05 |
| 11092.07 | 11107.19 | 11122.31 | | 13864.06 | 13882.93 | 13901.81 |
| 11137.08 | 11149.06 | 11161.04 | | 13903.15 | 13916.01 | 13928.87 |
| 11288.09 | 11306.44 | 11324.78 | | 13929.87 | 13943.07 | 13956.27 |
| 11357.26 | 11375.9 | 11394.54 | | 13958.61 | 13983.66 | 14008.72 |
| 11396.27 | 11410.09 | 11423.9 | | 14015.73 | 14042.8 | 14069.86 |
| 11425.13 | 11447.54 | 11469.96 | | 14076.2 | 14097.59 | 14118.97 |
| 11505.19 | 11532.05 | 11558.92 | | 14124.31 | 14149.03 | 14173.76 |
| 11613 | 11627.24 | 11641.47 | | 14178.77 | 14198.98 | 14219.19 |
| 11642.18 | 11654.28 | 11666.38 | | 14231.55 | 14254.61 | 14277.66 |
| 11666.74 | 11688.44 | 11710.15 | | 14281.33 | 14306.56 | 14331.78 |
| 11712.08 | 11733.43 | 11754.78 | | 14461.45 | 14515 | 14568.55 |
| 11756.23 | 11786.66 | 11817.09 | | 14751.73 | 14784.47 | 14817.21 |
| 11817.93 | 11834.77 | 11851.61 | | 14857.63 | 14884.53 | 14911.42 |
| 11868.93 | 11898.52 | 11928.11 | | 14949.73 | 14975.44 | 15001.15 |
| 11928.7 | 11944.87 | 11961.05 | | 15009.14 | 15028.79 | 15048.44 |
| 12143.52 | 12158.28 | 12173.04 | | 15527.48 | 15563.22 | 15598.97 |
| 12271.47 | 12290.85 | 12310.22 | | 15713.63 | 15753.95 | 15794.27 |
| 12400.43 | 12412.62 | 12424.81 | | 16465.93 | 16502.17 | 16538.42 |
| 12433.83 | 12457.39 | 12480.94 | | 16610.92 | 16630.13 | 16649.34 |
| 12489.93 | 12507.27 | 12524.61 | | 16999.46 | 17032.54 | 17065.61 |
| 12536.4 | 12565.8 | 12595.2 | | 17104.03 | 17148.13 | 17192.23 |
| 12597.2 | 12613.41 | 12629.61 | | 17225.64 | 17270.91 | 17316.18 |
| 12647.98 | 12674.21 | 12700.44 | | 17318.65 | 17335.6 | 17352.55 |
| 12716.47 | 12738.02 | 12759.57 | | 17359.48 | 17401.7 | 17443.93 |
| 12761.24 | 12785.79 | 12810.35 | | 17445.13 | 17476.37 | 17507.61 |
| 12829.73 | 12873.16 | 12916.59 | | 17569.08 | 17604.33 | 17639.57 |
| 12935.63 | 12967.54 | 12999.44 | | 17774.54 | 17815.47 | 17856.39 |
| 13051.23 | 13080.96 | 13110.69 | | 17982.34 | 18031.12 | 18079.9 |
| 13117.71 | 13134.41 | 13151.12 | | 18232.58 | 18275.34 | 18318.1 |
| 13225.86 | 13241.27 | 13256.68 | | 18593.72 | 18636.99 | 18680.25 |
| 13258.69 | 13274.73 | 13290.77 | | 18816.22 | 18850.13 | 18884.04 |
| 13304.99 | 13318.16 | 13331.32 | | 19339.07 | 19373.15 | 19407.22 |
| 13347.56 | 13364.6 | 13381.64 | | 19407.56 | 19463.85 | 19520.15 |
| 13402.57 | 13413.92 | 13425.28 | | 19522.82 | 19575.27 | 19627.72 |
| 13510.26 | 13524.96 | 13539.66 | | 20740.85 | 20811.99 | 20883.14 |
| 13551.35 | 13567.72 | 13584.09 | | 20886.89 | 20945.69 | 21004.49 |
| 13597.13 | 13624.17 | 13651.21 | | 21005.16 | 21061.95 | 21118.75 |

| | | |
|---|---|---|
| 21119.42 | 21170.37 | 21221.31 |
| 21221.98 | 21275.44 | 21328.89 |
| 21330.89 | 21377.17 | 21423.44 |
| 21428.09 | 21475.32 | 21522.55 |
| 21642.26 | 21687.7 | 21733.13 |
| 21733.61 | 21755.74 | 21777.87 |
| 21778.15 | 21807.79 | 21837.44 |
| 21837.72 | 21862.69 | 21887.65 |
| 21887.93 | 21917.15 | 21946.37 |
| 22967.23 | 23036.05 | 23104.87 |
| 23110.29 | 23160.86 | 23211.44 |
| 23212.98 | 23256.28 | 23299.59 |
| 23407.68 | 23468.85 | 23530.03 |
| 27630.18 | 27715.9 | 27801.62 |
| 27874.33 | 27944.17 | 28014.01 |
| 28015.03 | 28082.32 | 28149.61 |

Example 3 Appendix B: Batch Correction

Table B.1 Batch correction coefficients

| Model | A0 | A1 | B0 | B1 | C |
|---|---|---|---|---|---|
| Batch2 | 7.86E-01 | 1.97E-02 | 3.04E-05 | -1.53E-06 | -7.82E-10 |
| Batch3 | 8.76E-01 | 6.70E-03 | 2.45E-05 | -7.89E-07 | -6.40E-10 |
| Batch4 | 8.41E-01 | -4.54E-03 | 2.64E-05 | -6.29E-08 | -6.92E-10 |
| Batch5 | 8.69E-01 | 2.57E-02 | 2.87E-05 | -3.49E-06 | -8.96E-10 |
| Batch6 | 8.43E-01 | -1.51E-02 | 3.66E-05 | 1.52E-06 | -1.23E-09 |

Figure B.1 Batch correction plots pre-correction
Batch 2 Pre Correction
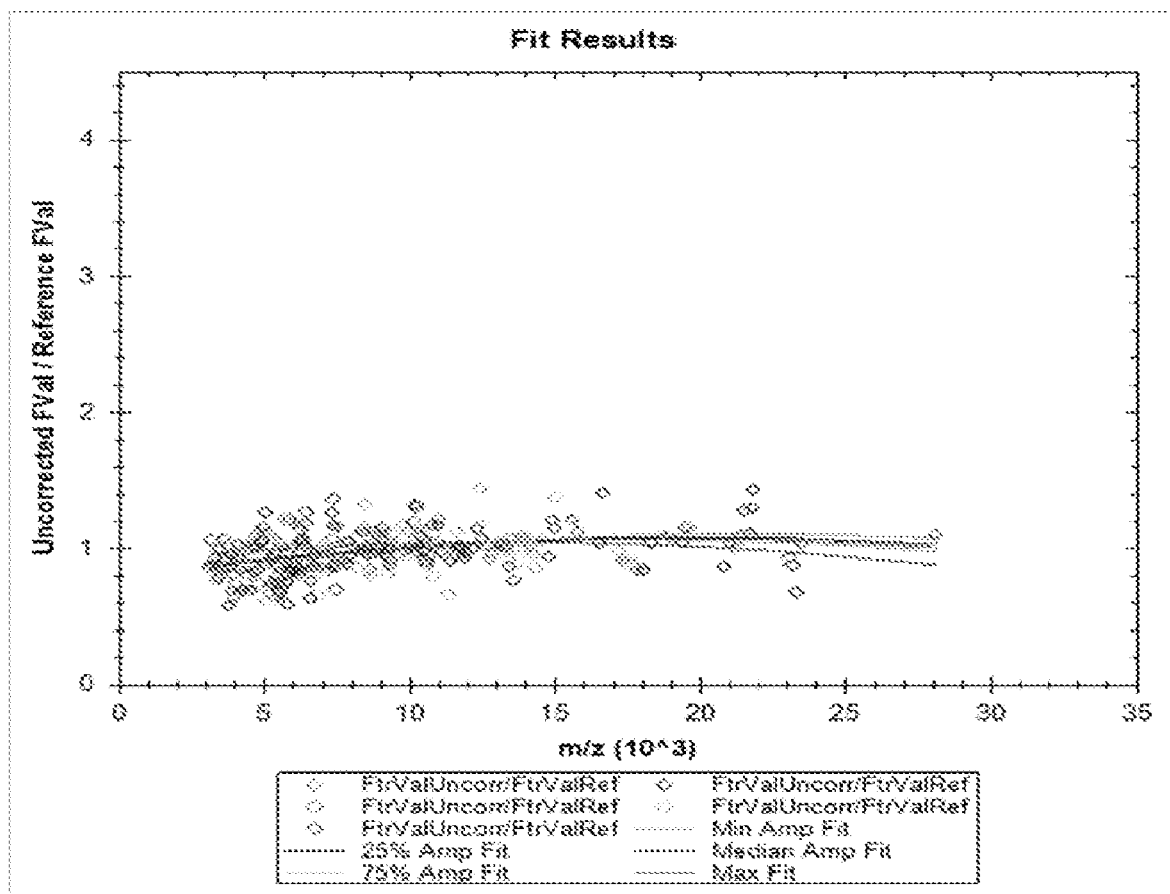

Batch 3 Pre Correction
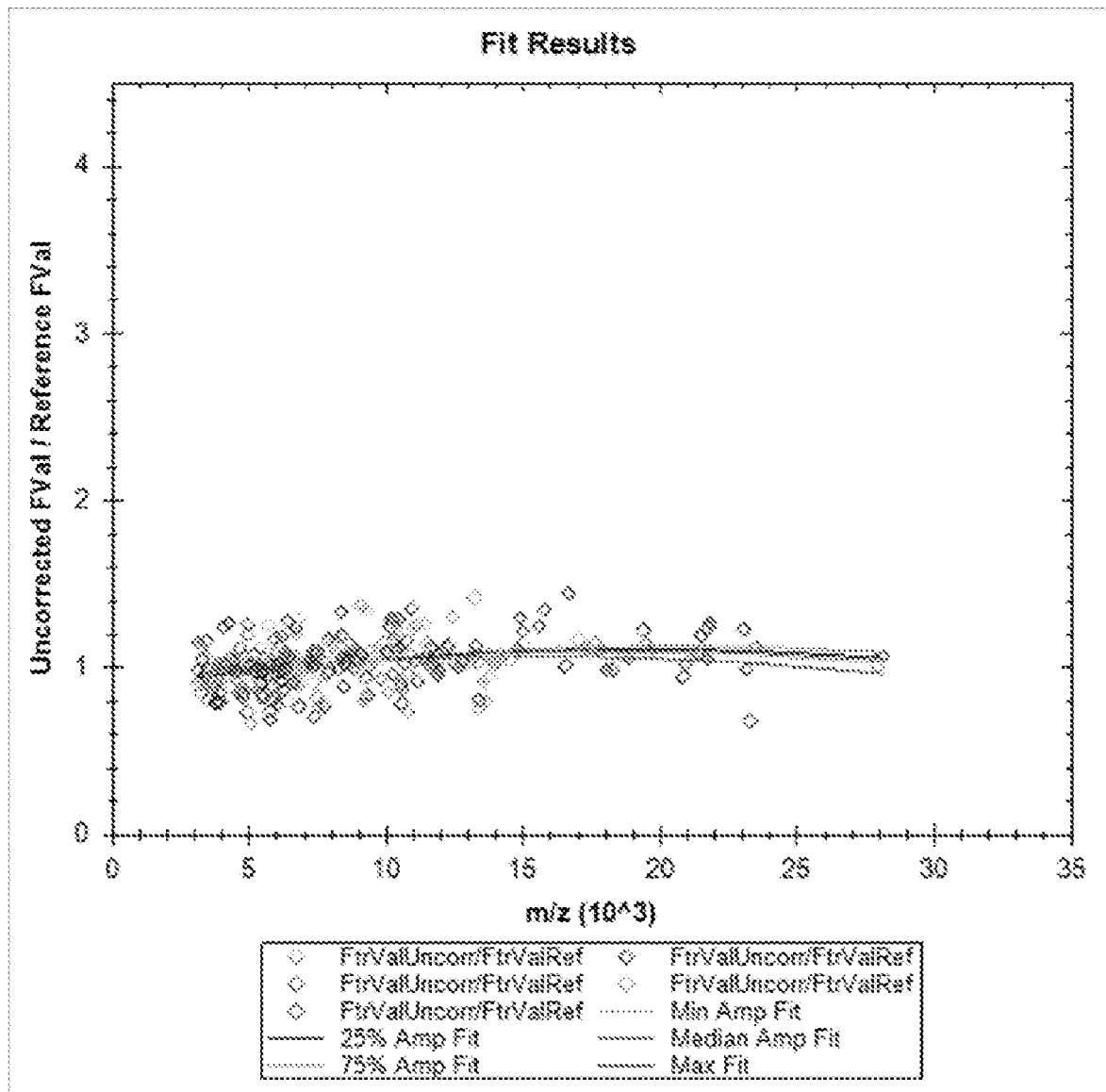

Batch 4 Pre Correction
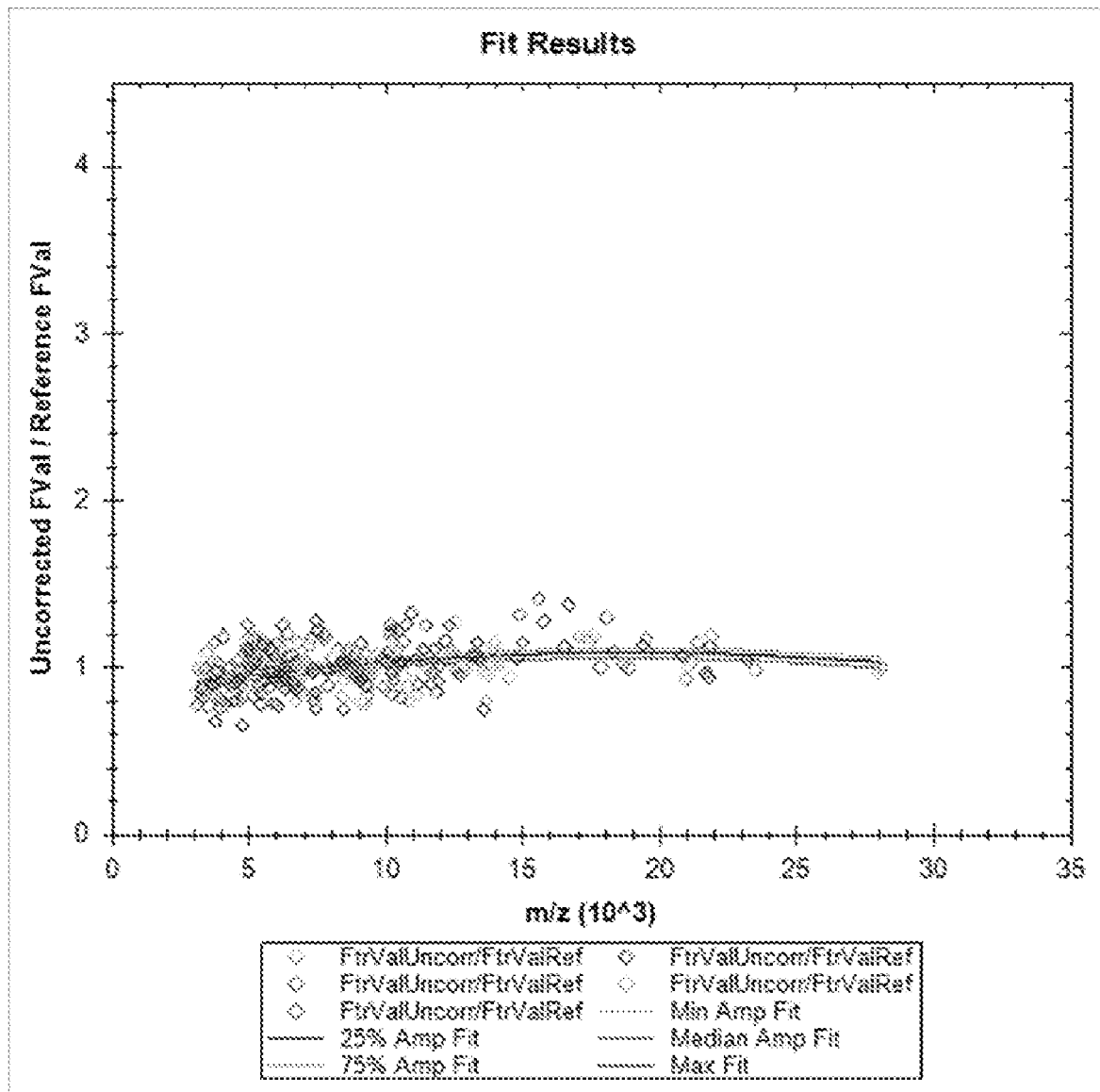

Batch 5 Pre Correction
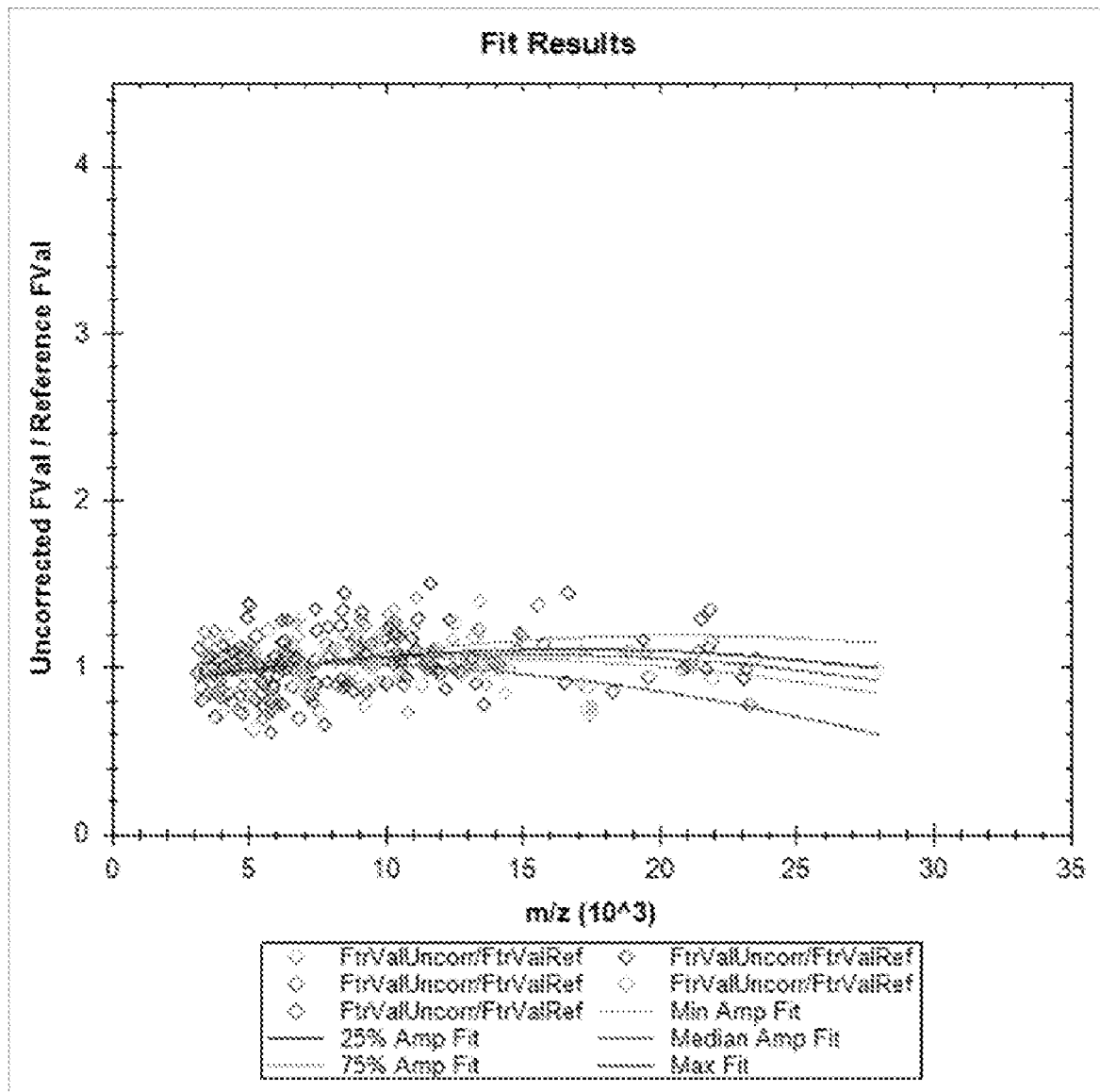

Batch 6 Pre Correction
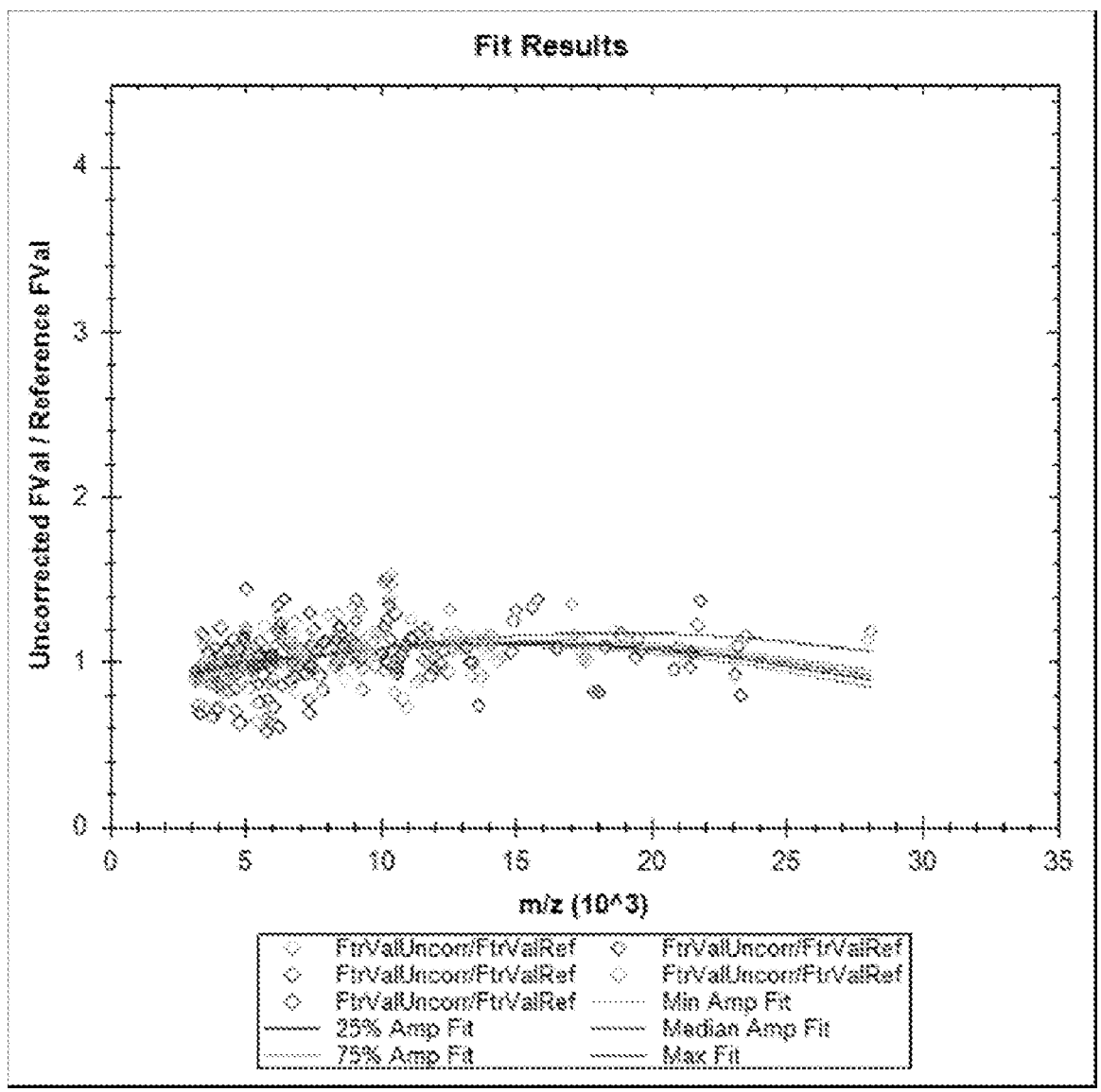
Table B.2 Batch correction coefficients on corrected tables
| Model  | A0       | A1        | B0        | B1        | C         | ResSD    |
|--------|----------|-----------|-----------|-----------|-----------|----------|
| Batch2 | 1.00E+00 | -7.90E-05 | -4.00E-07 | 7.28E-08  | 2.14E-11  | 1.40E-01 |
| Batch3 | 1.01E+00 | 8.79E-04  | -2.03E-06 | 3.78E-08  | 7.00E-11  | 1.23E-01 |
| Batch4 | 9.95E-01 | -5.85E-04 | 8.10E-07  | 4.13E-08  | -2.76E-11 | 1.15E-01 |
| Batch5 | 1.03E+00 | -1.12E-02 | -5.79E-06 | 1.06E-06  | 2.03E-10  | 1.50E-01 |
| Batch6 | 9.90E-01 | -2.56E-04 | 2.06E-06  | -1.19E-07 | -5.97E-11 | 1.41E-01 |

Figure B.2 Batch correction plots post-correction
Batch 2 Post Correction
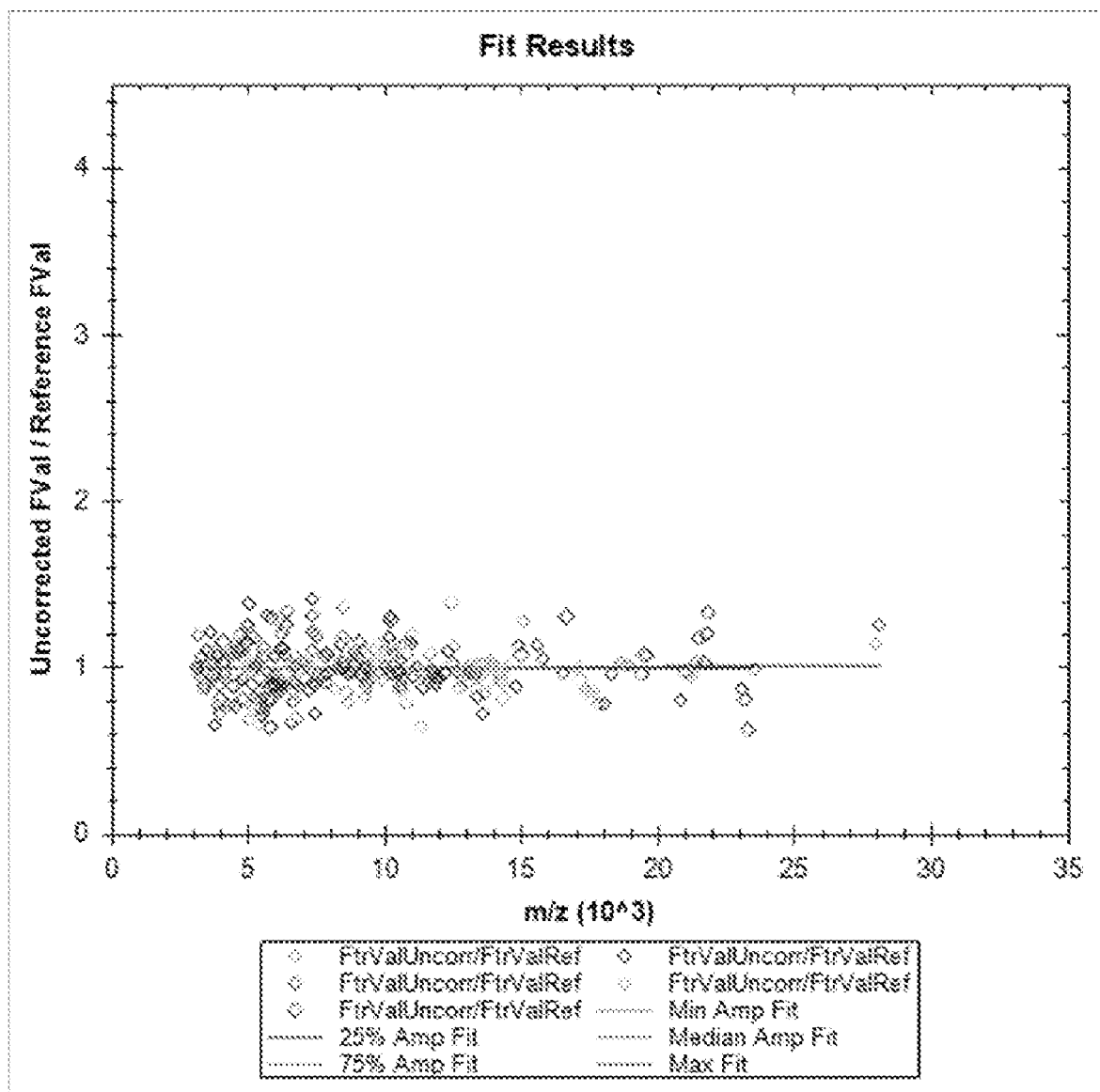

Batch 3 Post Correction
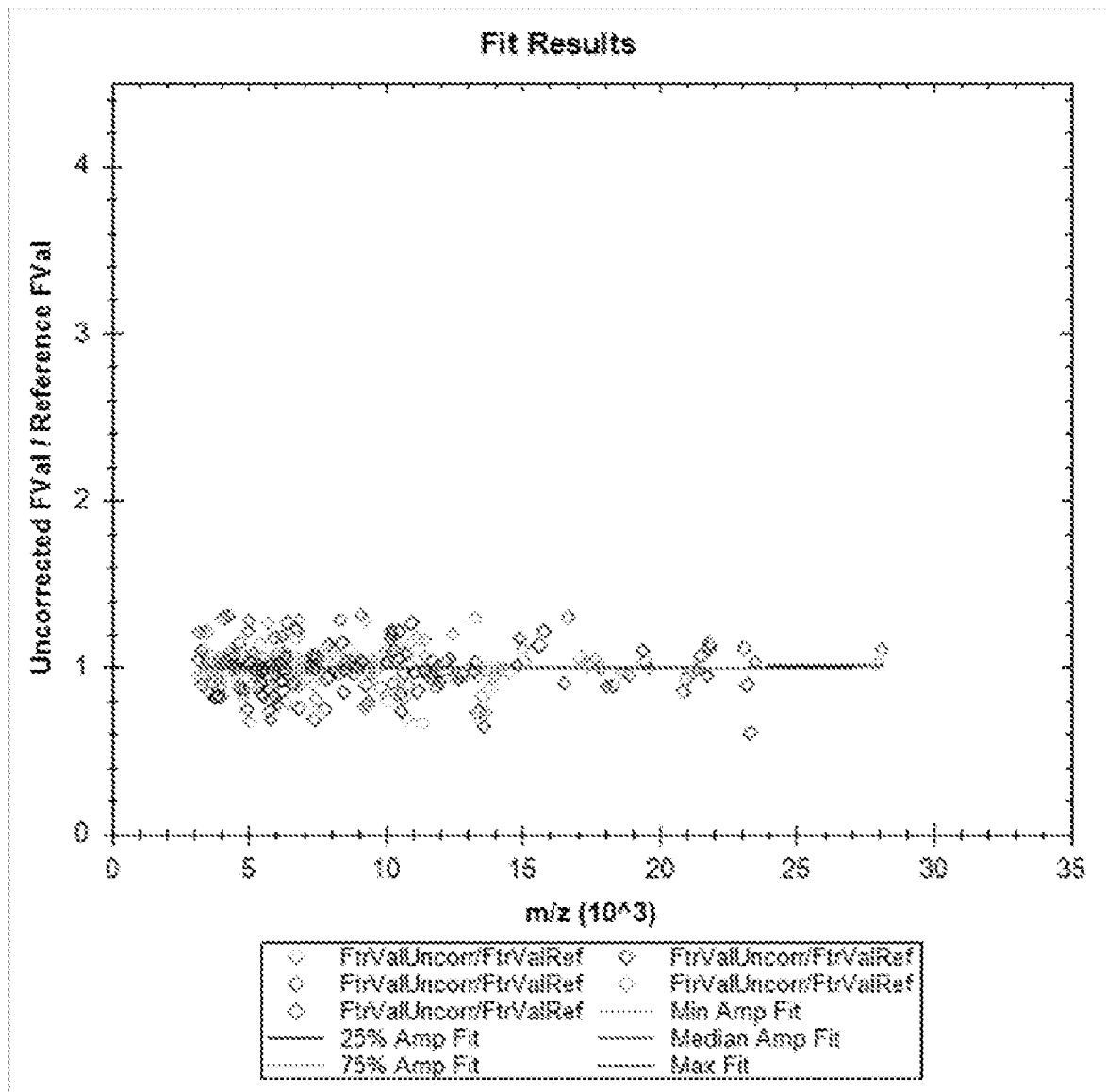

Batch 4 Post Correction
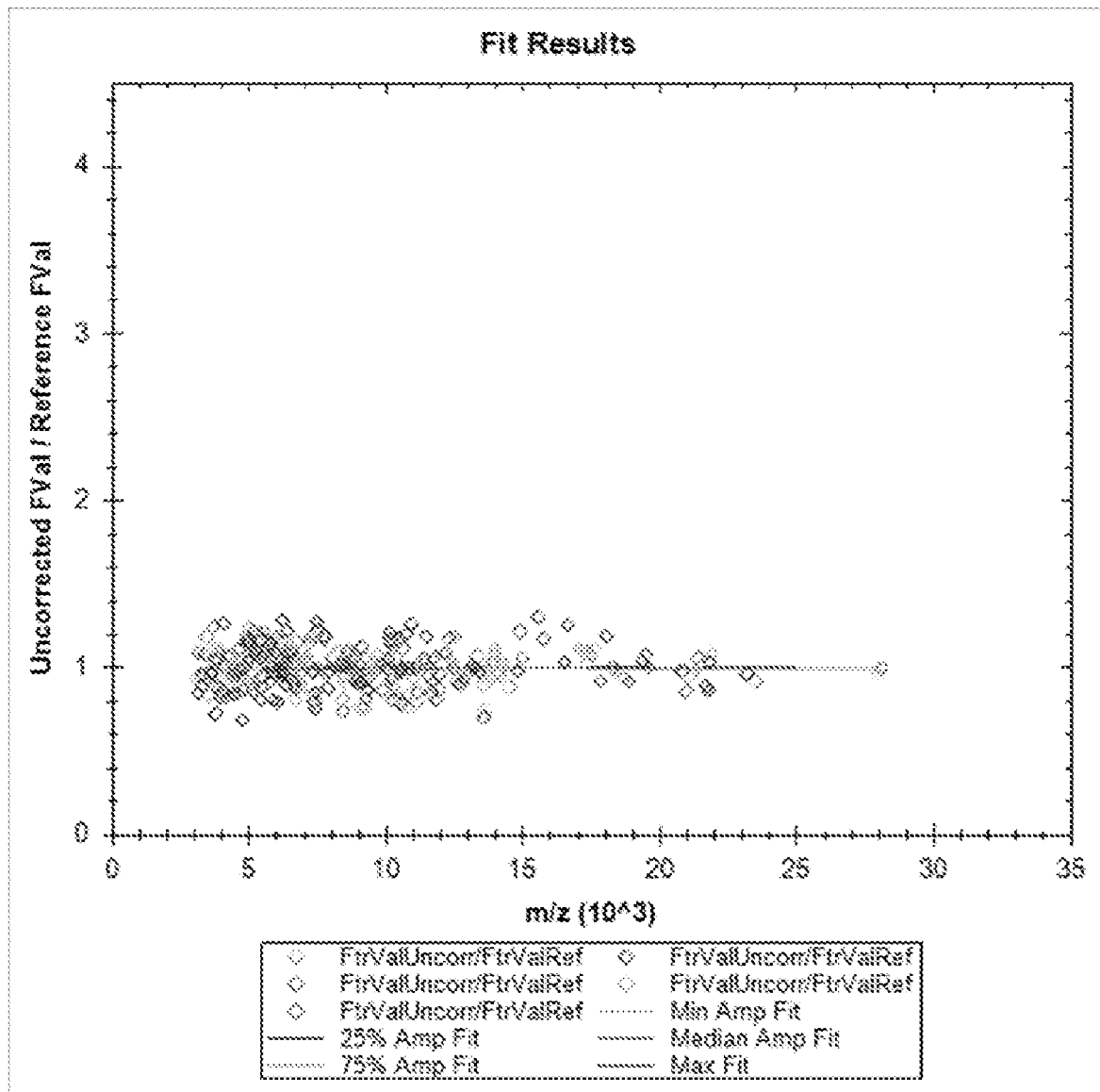

Batch 5 Post Correction
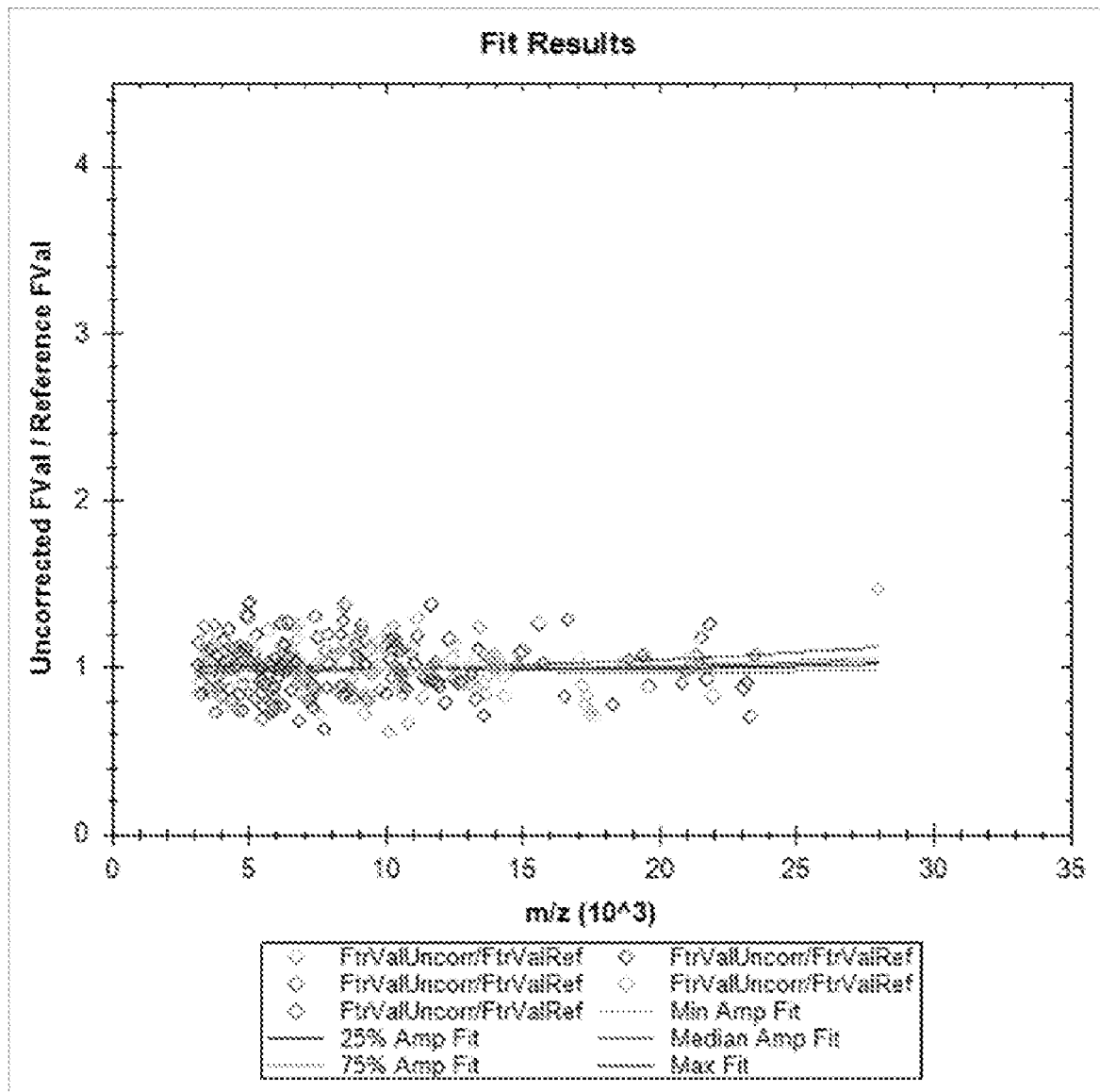

Batch 6 Post Correction

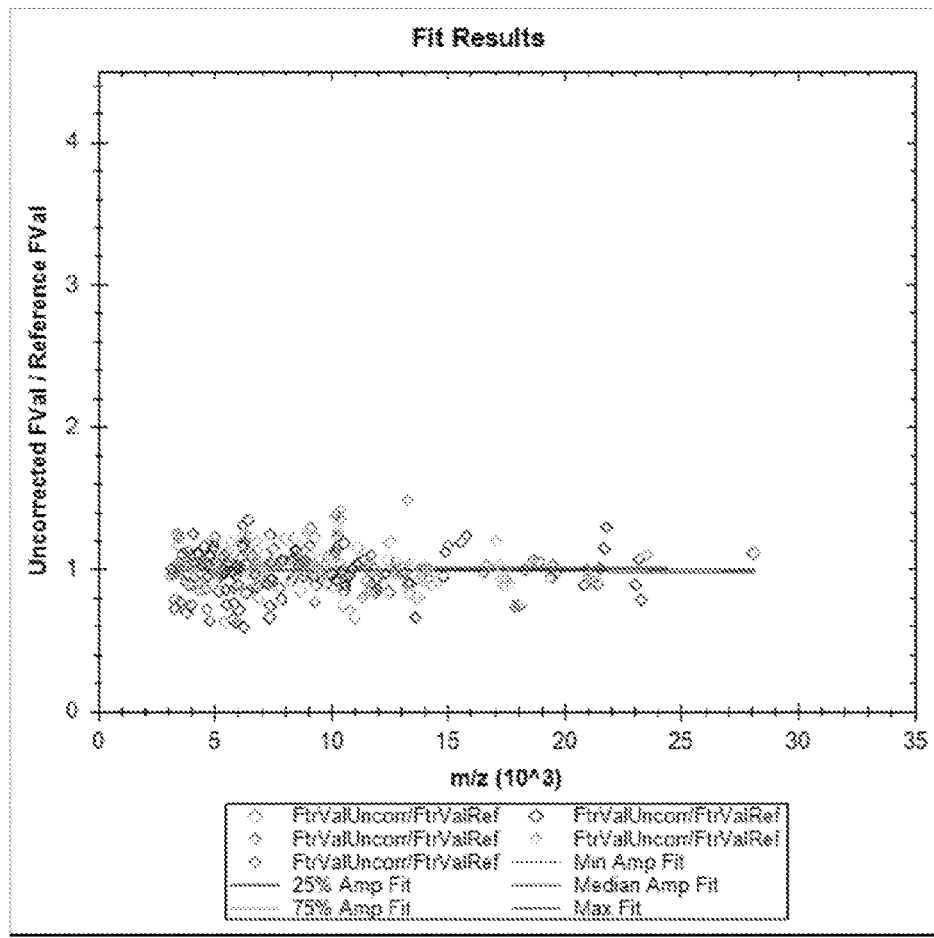
Example 3

Appendix C: Feature Deselection Method

A multitude of splits (a total of 625) of the development set samples into two subsets is created. One of the subsets is used for feature (de)selection and the remainder is left aside.

For each split a kNN classifier is created using the given subset as the training set of the classifier and one single feature. For this project k = 7 was used. The created classifier is applied to the training subset and the classifier performance is assessed in terms of hazard ratio between classification groups (Early vs Late). A filter is applied to these performance estimates, such that the feature only passes filtering if the classifier using this sample subset for training has adequate performance. For the approaches used in this report, the feature deselection step used K = 7 for the kNN classifiers and a hazard ratio range for filtering between 2.5 and 10.0, for both approaches in all label flip iterations.

All features that pass filtering for a given subset choice are added to a list. This is repeated for all the subset realizations generated. The lists of features passing filtering are then compiled across the subset realizations to determine how often a feature passes filtering. Features that pass filtering in most of the subsets are likely to be useful and robust for the question being addressed, as they are not dependent on any particular sample subset. Features that pass filtering for very few subset realizations are likely to have been overfitted to those few subsets and are not likely to be useful.

Figure C.1 shows an example of the distribution of how many features pass filtering in how many subset realizations.

It is apparent that the distribution falls off quite quickly with a tail containing features that occur in a relatively large proportion of subset realizations, which are those which are likely to be most useful for classifier development.

Figure C.1: Number of features passing filtering for a given number of subset realizations (y axis) vs. the number of subset realizations. (Red line shows the cut off for which features were deselected for that specific iteration)

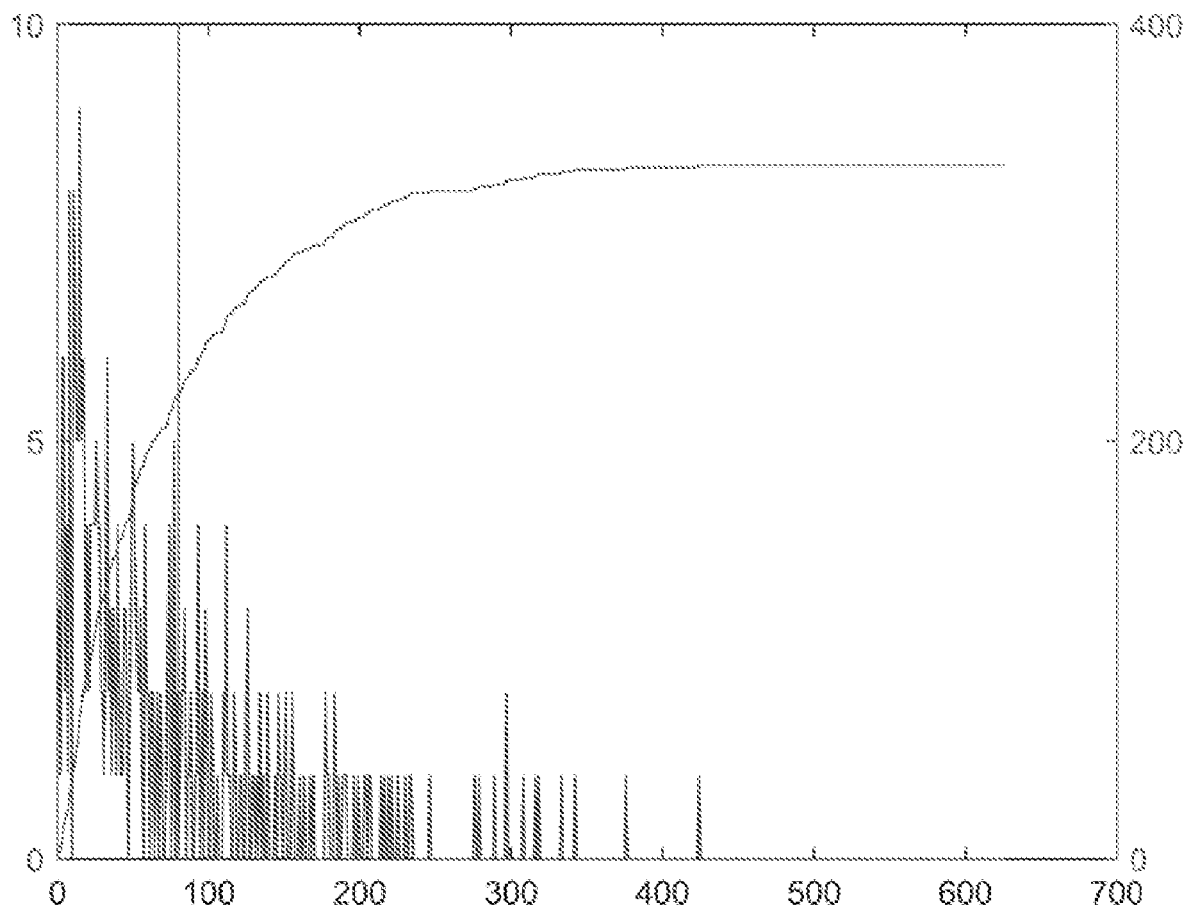

Example 3 Appendix D: Features used in final classifiers

| Approach (1) | Approach (2) |
|---|---|
| 3110 | 3110 |
| 3211 | 3243 |
| 3243 | 3265 |
| 3265 | 3317 |
| 3317 | 3554 |
| 3554 | 3755 |
| 3755 | 3776 |
| 3776 | 3887 |
| 3887 | 4099 |
| 3953 | 4266 |
| 4099 | 4286 |
| 4266 | 4431 |
| 4286 | 4643 |
| 4431 | 4718 |
| 4593 | 4756 |
| 4718 | 4891 |
| 4756 | 4918 |
| 4891 | 4938 |
| 4938 | 5068 |
| 5041 | 5156 |
| 5068 | 5182 |
| 5156 | 5224 |
| 5182 | 5675 |
| 5224 | 5710 |
| 5675 | 5748 |
| 5710 | 5777 |
| 5748 | 5816 |
| 5777 | 5997 |
| 5816 | 6210 |
| 5997 | 6332 |
| 6109 | 6634 |
| 6210 | 6657 |
| 6283 | 6773 |
| 6332 | 6860 |
| 6438 | 6881 |
| 6634 | 6898 |
| 6657 | 6971 |
| 6756 | 6992 |
| 6773 | 7074 |
| 6793 | 7258 |

| | |
|---|---|
| 6860 | 7322 |
| 6881 | 7334 |
| 6898 | 7346 |
| 6971 | 7420 |
| 6992 | 7448 |
| 7074 | 7779 |
| 7258 | 7871 |
| 7322 | 8391 |
| 7334 | 8464 |
| 7346 | 8509 |
| 7420 | 8531 |
| 7448 | 8565 |
| 7479 | 8632 |
| 7779 | 8661 |
| 7871 | 8729 |
| 8391 | 8746 |
| 8464 | 8771 |
| 8509 | 8902 |
| 8531 | 8998 |
| 8565 | 9079 |
| 8632 | 9206 |
| 8661 | 9264 |
| 8696 | 9359 |
| 8729 | 9430 |
| 8746 | 10079 |
| 8771 | 10421 |
| 8891 | 10533 |
| 8902 | 10734 |
| 8998 | 11306 |
| 9079 | 12507 |
| 9098 | 12613 |
| 9206 | 13275 |
| 9264 | 13624 |
| 9359 | 13943 |
| 9430 | 13984 |
| 9641 | 14043 |
| 9721 | 15029 |
| 9793 | 17033 |
| 10079 | 17148 |
| 10421 | 17271 |
| 10449 | 17336 |
| 10533 | 18850 |
| 10734 | 19464 |

| | |
|---|---|
| 11306 | 19575 |
| 11448 | 20812 |
| 11945 | 20946 |
| 12507 | 21062 |
| 12613 | 21917 |
| 13275 | 23036 |
| 13624 | 27716 |
| 13883 | 27944 |
| 13943 | 28082 |
| 13984 | 30001 * |
| 14043 | 30002 * |
| 14199 | 30003 * |
| 14784 | |
| 15029 | |
| 16630 | |
| 17033 | |
| 17148 | |
| 17271 | |
| 17336 | |
| 18850 | |
| 19464 | |
| 19575 | |
| 20812 | |
| 20946 | |
| 21062 | |
| 21475 | |
| 23036 | |
| 23256 | |
| 27716 | |
| 27944 | |
| 28082 | |

\* 30001: Age at diagnosis; 30002: PSA (ng / ml); 30003: fPSA (%). All other features refer to m/z values.

Example 3 Appendix E: Classifications by sample

| Filename | SampleID | Classification (Approach (1)) | Classification (Approach (2)) |
|---|---|---|---|
| Average_00001_100070597.txt | 100070597 | Early | Early |
| Average_00001_101051627.txt | 101051627 | Late | Late |
| Average_00001_108429555.txt | 108429555 | Late | Late |
| Average_00001_112805.txt | 112805 | Early | Early |
| Average_00001_118508.txt | 118508 | Early | Early |
| Average_00001_157578.txt | 157578 | Late | Late |
| Average_00001_157590.txt | 157590 | Late | Late |
| Average_00001_158292.txt | 158292 | Late | Late |
| Average_00001_180920.txt | 180920 | Late | Late |
| Average_00001_182834.txt | 182834 | Late | Late |
| Average_00001_183488.txt | 183488 | Early | Early |
| Average_00001_190911.txt | 190911 | Late | Late |
| Average_00001_209775.txt | 209775 | Early | Early |
| Average_00001_223900.txt | 223900 | Late | Late |
| Average_00001_224788.txt | 224788 | Late | Late |
| Average_00001_226786.txt | 226786 | Late | Late |
| Average_00001_226987.txt | 226987 | Early | Early |
| Average_00001_228905.txt | 228905 | Late | Late |
| Average_00001_229360.txt | 229360 | Early | Early |
| Average_00001_239074.txt | 239074 | Late | Late |
| Average_00001_241112.txt | 241112 | Late | Late |
| Average_00001_241121.txt | 241121 | Late | Late |
| Average_00001_241122.txt | 241122 | Late | Late |
| Average_00001_255951.txt | 255951 | Late | Late |
| Average_00001_255985.txt | 255985 | Early | Early |
| Average_00001_260476.txt | 260476 | Early | Early |
| Average_00001_273316.txt | 273316 | Early | Early |
| Average_00001_274982.txt | 274982 | Late | Late |
| Average_00001_278636.txt | 278636 | Early | Early |
| Average_00001_286982.txt | 286982 | Early | Early |
| Average_00001_287874.txt | 287874 | Early | Early |
| Average_00001_287880.txt | 287880 | Late | Late |
| Average_00001_289609.txt | 289609 | Late | Late |
| Average_00001_294677.txt | 294677 | Early | Early |
| Average_00001_294981.txt | 294981 | Late | Late |
| Average_00001_296404.txt | 296404 | Late | Early |
| Average_00001_296417.txt | 296417 | Late | Late |
| Average_00001_296898.txt | 296898 | Late | Late |

| | | | |
|---|---|---|---|
| Average_00001_296944.txt | 296944 | Late | Late |
| Average_00001_307920.txt | 307920 | Early | Early |
| Average_00001_310070.txt | 310070 | Late | Late |
| Average_00001_310370.txt | 310370 | Early | Early |
| Average_00001_312967.txt | 312967 | Late | Late |
| Average_00001_313197.txt | 313197 | Early | Early |
| Average_00001_313595.txt | 313595 | Early | Early |
| Average_00001_316897.txt | 316897 | Late | Late |
| Average_00001_319783.txt | 319783 | Early | Early |
| Average_00001_319933.txt | 319933 | Early | Early |
| Average_00001_319953.txt | 319953 | Early | Early |
| Average_00001_319978.txt | 319978 | Late | Late |
| Average_00001_323657.txt | 323657 | Late | Late |
| Average_00001_323670.txt | 323670 | Early | Late |
| Average_00001_323914.txt | 323914 | Early | Early |
| Average_00001_325081.txt | 325081 | Late | Late |
| Average_00001_326057.txt | 326057 | Early | Early |
| Average_00001_326060.txt | 326060 | Early | Early |
| Average_00001_326316.txt | 326316 | Late | Late |
| Average_00001_326450.txt | 326450 | Late | Late |
| Average_00001_327622.txt | 327622 | Early | Early |
| Average_00001_327684.txt | 327684 | Early | Early |
| Average_00001_328489.txt | 328489 | Early | Early |
| Average_00001_328957.txt | 328957 | Late | Late |
| Average_00001_329385.txt | 329385 | Late | Late |
| Average_00001_330169.txt | 330169 | Early | Early |
| Average_00001_332082.txt | 332082 | Late | Late |
| Average_00001_332578.txt | 332578 | Late | Late |
| Average_00001_334141.txt | 334141 | Early | Early |
| Average_00001_334255.txt | 334255 | Early | Early |
| Average_00001_336363.txt | 336363 | Late | Late |
| Average_00001_336955.txt | 336955 | Early | Early |
| Average_00001_339433.txt | 339433 | Late | Late |
| Average_00001_341209.txt | 341209 | Late | Late |
| Average_00001_341734.txt | 341734 | Late | Late |
| Average_00001_341925.txt | 341925 | Late | Late |
| Average_00001_342099.txt | 342099 | Early | Early |
| Average_00001_342860.txt | 342860 | Late | Late |
| Average_00001_342985.txt | 342985 | Late | Late |
| Average_00001_343874.txt | 343874 | Late | Late |
| Average_00001_344282.txt | 344282 | Late | Late |
| Average_00001_344289.txt | 344289 | Late | Late |
| Average_00001_344939.txt | 344939 | Late | Late |

| | | | |
|---|---|---|---|
| Average_00001_345168.txt | 345168 | Early | Early |
| Average_00001_346821.txt | 346821 | Late | Late |
| Average_00001_347163.txt | 347163 | Early | Early |
| Average_00001_348382.txt | 348382 | Early | Early |
| Average_00001_350235.txt | 350235 | Early | Early |
| Average_00001_353843.txt | 353843 | Late | Late |
| Average_00001_354225.txt | 354225 | Early | Early |
| Average_00001_354400.txt | 354400 | Late | Late |
| Average_00001_355346.txt | 355346 | Early | Early |
| Average_00001_355914.txt | 355914 | Late | Late |
| Average_00001_361015.txt | 361015 | Late | Late |
| Average_00001_363529.txt | 363529 | Early | Early |
| Average_00001_363749.txt | 363749 | Late | Late |
| Average_00001_370511.txt | 370511 | Early | Early |
| Average_00001_371762.txt | 371762 | Early | Early |
| Average_00001_5704021811.txt | 5704021811 | Early | Early |
| Average_00001_5802062717.txt | 5802062717 | Late | Late |
| Average_00001_5836060014.txt | 5836060014 | Early | Early |
| Average_00001_5913033212.txt | 5913033212 | Late | Late |
| Average_00001_601870.txt | 601870 | Early | Early |
| Average_00001_610232.txt | 610232 | Late | Late |
| Average_00001_610772.txt | 610772 | Late | Late |
| Average_00001_613294.txt | 613294 | Early | Early |
| Average_00001_622251.txt | 622251 | Late | Late |
| Average_00001_623716.txt | 623716 | Early | Early |
| Average_00001_626399.txt | 626399 | Early | Early |
| Average_00001_628652.txt | 628652 | Late | Late |
| Average_00001_630085.txt | 630085 | Late | Late |
| Average_00001_636662.txt | 636662 | Late | Late |
| Average_00001_637317.txt | 637317 | Early | Late |
| Average_00001_640612.txt | 640612 | Late | Late |
| Average_00001_640794.txt | 640794 | Early | Early |
| Average_00001_641548.txt | 641548 | Late | Late |
| Average_00001_649071.txt | 649071 | Late | Late |
| Average_00001_660326.txt | 660326 | Early | Early |
| Average_00001_661812.txt | 661812 | Late | Late |
| Average_00001_662523.txt | 662523 | Early | Early |
| Average_00001_663348.txt | 663348 | Early | Early |
| Average_00001_665928.txt | 665928 | Late | Late |
| Average_00001_669710.txt | 669710 | Early | Early |
| Average_00001_672480.txt | 672480 | Early | Early |
| Average_00001_676629.txt | 676629 | Early | Early |
| Average_00001_89287.txt | 89287 | Late | Late |

------ end of appendices ------

We claim:
1. A system for prostate cancer aggressiveness or indolence prediction, comprising:
a computer system including a memory storing a final classifier in memory defined from one or more master classifiers generated by conducting logistic regression with extreme drop-out on a multitude of mini-classifiers which meet predefined filtering criteria, wherein the mini-classifiers execute a K-nearest neighbor classification algorithm on a set of features selected from the list of features set forth below

| Left m/z | Center m/z | Right m/z |
|---|---|---|
| 3081.583 | 3090.249 | 3098.915 |
| 3308.621 | 3329.648 | 3350.675 |
| 4145.045 | 4160.911 | 4176.776 |
| 4177.923 | 4197.23 | 4216.536 |
| 4446.822 | 4468.04 | 4489.258 |
| 4556.927 | 4572.41 | 4587.894 |
| 4694.939 | 4717.304 | 4739.669 |
| 4772.094 | 4790.636 | 4809.178 |
| 4809.56 | 4824.661 | 4839.762 |
| 4846.644 | 4860.598 | 4874.552 |
| 4880.493 | 4896.55 | 4912.607 |
| 5053.678 | 5071.264 | 5088.85 |
| 5090.762 | 5109.303 | 5127.845 |
| 5279.182 | 5292.874 | 5306.565 |
| 6376.924 | 6430.949 | 6484.973 |
| 6576.342 | 6590.984 | 6605.625 |
| 6606.408 | 6652.759 | 6699.111 |
| 6782.803 | 6797.117 | 6811.43 |
| 6822.441 | 6835.653 | 6848.866 |
| 6849.6 | 6859.632 | 6869.663 |
| 6870.397 | 6891.073 | 6911.748 |
| 6928.141 | 6946.736 | 6965.332 |
| 7018.671 | 7055.25 | 7091.829 |
| 7370.816 | 7387.447 | 7404.077 |
| 7405.224 | 7419.56 | 7433.897 |
| 7514.946 | 7556.617 | 7598.289 |
| 7658.311 | 7681.058 | 7703.805 |
| 7893.703 | 7945.124 | 7996.544 |
| 7999.22 | 8034.583 | 8069.947 |
| 8181.751 | 8209.468 | 8237.185 |
| 8551.43 | 8562.293 | 8573.157 |
| 8574.723 | 8589.795 | 8604.867 |
| 8666.721 | 8691.776 | 8716.831 |
| 8730.019 | 8759.869 | 8789.72 |
| 8792.411 | 8818.347 | 8844.283 |
| 8859.941 | 8870.798 | 8881.656 |
| 8883.796 | 8923.25 | 8962.704 |
| 9043.529 | 9067.232 | 9090.935 |
| 9092.465 | 9154.245 | 9216.026 |
| 9265.334 | 9282.308 | 9299.283 |
| 9324.362 | 9346.077 | 9367.792 |
| 9368.098 | 9381.861 | 9395.624 |
| 9398.071 | 9433.855 | 9469.639 |
| 9471.168 | 9487.836 | 9504.505 |
| 9617.762 | 9641.159 | 9664.556 |
| 9690.553 | 9717.467 | 9744.382 |
| 9777.537 | 9793.747 | 9809.957 |
| 9902.628 | 9935.506 | 9968.385 |
| 10325.87 | 10347.13 | 10368.38 |
| 10430.11 | 10453.51 | 10476.9 |
| 11502.59 | 11525.29 | 11547.99 |
| 11642.19 | 11673.55 | 11704.91 |
| 11709.09 | 11730.3 | 11751.51 |
| 12525.06 | 12571.66 | 12618.25 |
| 12808.63 | 12864.18 | 12919.74 |
| 13676.71 | 13706.17 | 13735.63 |
| 13737.77 | 13758.42 | 13779.07 |
| 13781.02 | 13797.76 | 13814.5 |
| 13825.46 | 13839.55 | 13853.64 |
| 13855.09 | 13877.11 | 13899.13 |
| 13899.72 | 13913.81 | 13927.91 |
| 13928.52 | 13939.29 | 13950.05 |
| 13958.08 | 13970.19 | 13982.3 |
| 14026.12 | 14041.39 | 14056.66 |

-continued

| Left m/z | Center m/z | Right m/z |
|---|---|---|
| 14056.69 | 14066.96 | 14077.23 |
| 14612.46 | 14676.26 | 14740.06 |
| 15010.07 | 15126.44 | 15242.8 |
| 15269.09 | 15291.55 | 15314.01 |
| 15315.44 | 15345.55 | 15375.65 |
| 15724.22 | 15852.06 | 15979.89 |
| 16008.09 | 16031.26 | 16054.44 |
| 16056.83 | 16093.15 | 16129.47 |
| 16605.01 | 16682.66 | 16760.32 |
| 17091.97 | 17138.56 | 17185.16 |
| 17223.02 | 17266.27 | 17309.52 |
| 17333.41 | 17393.86 | 17454.31 |
| 17563.93 | 17601.92 | 17639.91 |
| 18598.12 | 18640.3 | 18682.49 |
| 21007.96 | 21074.42 | 21140.87 |
| 21949.42 | 22238.76 | 22528.1 |
| 27742.59 | 27978.55 | 28214.5 |
| 28227.94 | 28314.56 | 28401.17 |
| 28793.87 | 28909.23 | 29024.6 |
| 29572.29 | 29667.12 | 29761.95 |
| 3153.208 | 3164.868 | 3176.529 |
| 3353.837 | 3372.531 | 3391.224 |
| 3419.727 | 3442.492 | 3465.257 |
| 3473.03 | 3490.798 | 3508.566 |
| 4055.23 | 4068.741 | 4082.252 |
| 4137.036 | 4153.693 | 4170.351 |
| 4170.721 | 4190.155 | 4209.588 |
| 4698.8 | 4712.168 | 4725.537 |
| 4759.221 | 4802.16 | 4845.099 |
| 4983.911 | 5008.526 | 5033.142 |
| 5053.501 | 5069.418 | 5085.336 |
| 5090.443 | 5104.695 | 5118.946 |
| 5121.167 | 5133.938 | 5146.708 |
| 5525.044 | 5570.204 | 5615.365 |
| 5843.444 | 5879.72 | 5915.996 |
| 5978.924 | 6000.949 | 6022.974 |
| 6366.989 | 6387.348 | 6407.707 |
| 6409.047 | 6457.28 | 6505.514 |
| 6518.615 | 6532 | 6545.385 |
| 6623.863 | 6631.566 | 6639.268 |
| 6566.766 | 6632.507 | 6698.248 |
| 6785.31 | 6794.313 | 6803.315 |
| 6826.591 | 6838.081 | 6849.57 |
| 6850.447 | 6859.449 | 6868.452 |
| 6870.181 | 6882.263 | 6894.346 |
| 6916.615 | 6940.779 | 6964.943 |
| 7459.185 | 7488.68 | 7518.175 |
| 7526.229 | 7562.357 | 7598.486 |
| 7601.624 | 7617.379 | 7633.133 |
| 7657.771 | 7674.354 | 7690.938 |
| 7887.538 | 7929.737 | 7971.936 |
| 7976.674 | 7990.148 | 8003.622 |
| 8005.695 | 8033.827 | 8061.96 |
| 8188.822 | 8205.257 | 8221.693 |
| 8226.727 | 8238.276 | 8249.825 |
| 8651.726 | 8684.856 | 8717.985 |
| 8726.499 | 8759.074 | 8791.648 |
| 8797.941 | 8827.554 | 8857.167 |
| 8887.061 | 8931.11 | 8975.16 |
| 9041.789 | 9061.223 | 9080.657 |
| 9084.787 | 9147.53 | 9210.273 |
| 9281.714 | 9303.369 | 9325.024 |
| 9329.466 | 9346.308 | 9363.151 |
| 9366.482 | 9382.584 | 9398.686 |
| 9400.788 | 9437.805 | 9474.821 |
| 9623.278 | 9643.606 | 9663.934 |
| 9693.159 | 9709.261 | 9725.363 |
| 9727.954 | 9747.388 | 9766.821 |
| 9917.122 | 9933.965 | 9950.807 |
| 10045.12 | 10073.81 | 10102.5 |
| 10130.62 | 10227.42 | 10324.21 |
| 10326.06 | 10342.54 | 10359.01 |
| 10409.79 | 10460.69 | 10511.59 |
| 10610.05 | 10649.29 | 10688.53 |
| 10778.11 | 10838.26 | 10898.41 |
| 11501.77 | 11535.78 | 11569.79 |
| 11653.08 | 11680.38 | 11707.67 |

| Left m/z | Center m/z | Right m/z |
|---|---|---|
| 11713.23 | 11736.36 | 11759.5 |
| 12524.61 | 12570.59 | 12616.58 |
| 12768.69 | 12848.51 | 12928.32 |
| 13256.1 | 13278.08 | 13300.06 |
| 13490.6 | 13556.3 | 13622.01 |
| 13660.37 | 13699.01 | 13737.65 |
| 13740.89 | 13760.09 | 13779.29 |
| 13781.6 | 13794.79 | 13807.98 |
| 13825.56 | 13840.37 | 13855.17 |
| 13857.95 | 13878.31 | 13898.67 |
| 13901.91 | 13915.09 | 13928.28 |
| 13928.74 | 13942.62 | 13956.51 |
| 13960.21 | 13979.18 | 13998.15 |
| 14020.82 | 14048.12 | 14075.42 |
| 14078.2 | 14103.42 | 14128.63 |
| 14130.48 | 14156.63 | 14182.77 |
| 14339.49 | 14402.65 | 14465.81 |
| 14830.89 | 14885.25 | 14939.62 |
| 14941.47 | 14989.6 | 15037.72 |
| 15039.57 | 15067.33 | 15095.09 |
| 15096.02 | 15155.01 | 15214.01 |
| 15270.23 | 15291.74 | 15313.26 |
| 15314.65 | 15346.57 | 15378.5 |
| 15705.12 | 15736.59 | 15768.05 |
| 15769.44 | 15801.13 | 15832.83 |
| 15833.76 | 15867.07 | 15900.39 |
| 15901.31 | 15925.14 | 15948.97 |
| 15951.75 | 15981.59 | 16011.43 |
| 16014.21 | 16034.34 | 16054.47 |
| 16055.85 | 16088.94 | 16122.02 |
| 16125.23 | 16148 | 16170.78 |
| 16175.11 | 16204.76 | 16234.4 |
| 16600.22 | 16666.38 | 16732.53 |
| 17222.34 | 17246.92 | 17271.5 |
| 17272.23 | 17288.13 | 17304.04 |
| 17358.26 | 17377.42 | 17396.58 |
| 17398.03 | 17417.91 | 17437.79 |
| 17852.61 | 17901.41 | 17950.21 |
| 18594.98 | 18622.82 | 18650.65 |
| 18652.82 | 18677.4 | 18701.98 |
| 20902.69 | 20954.66 | 21006.62 |
| 21011.14 | 21064.46 | 21117.78 |
| 23258.31 | 23571.9 | 23885.49 |
| 27660.21 | 27839.26 | 28018.31 |
| 28019.44 | 28098.51 | 28177.59 |
| 28227.29 | 28315.97 | 28404.65 |
| 28815.5 | 28888.93 | 28962.36 |
| 3073.625 | 3085.665 | 3097.705 |
| 3098.586 | 3109.891 | 3121.197 |
| 3123.546 | 3138.669 | 3153.793 |
| 3190.793 | 3210.615 | 3230.436 |
| 3230.73 | 3242.623 | 3254.516 |
| 3255.103 | 3264.647 | 3274.191 |
| 3296.802 | 3316.77 | 3336.739 |
| 3349.072 | 3363.608 | 3378.144 |
| 3380.2 | 3391.946 | 3403.692 |
| 3405.16 | 3420.283 | 3435.407 |
| 3435.7 | 3445.097 | 3454.494 |
| 3454.788 | 3465.359 | 3475.931 |
| 3490.725 | 3508.305 | 3525.884 |
| 3531.431 | 3553.896 | 3576.36 |
| 3581.059 | 3593.099 | 3605.138 |
| 3665.631 | 3679.286 | 3692.941 |
| 3693.94 | 3712.036 | 3730.132 |
| 3745.211 | 3754.755 | 3764.299 |
| 3764.592 | 3775.604 | 3786.616 |
| 3798.592 | 3814.263 | 3829.933 |
| 3831.545 | 3841.53 | 3851.514 |
| 3876.474 | 3887.486 | 3898.499 |
| 3898.583 | 3906.18 | 3913.777 |
| 3914.356 | 3928.158 | 3941.959 |
| 3942.253 | 3953.412 | 3964.571 |
| 3994.23 | 4008.619 | 4023.008 |
| 4024.182 | 4031.67 | 4039.159 |
| 4039.452 | 4050.464 | 4061.476 |
| 4086.437 | 4098.77 | 4111.104 |
| 4111.308 | 4118.525 | 4125.742 |

| Left m/z | Center m/z | Right m/z |
|---|---|---|
| 4126.043 | 4133.109 | 4140.176 |
| 4198.812 | 4209.788 | 4220.764 |
| 4241.573 | 4249.445 | 4257.316 |
| 4258.28 | 4265.83 | 4273.38 |
| 4273.837 | 4286.166 | 4298.495 |
| 4328.264 | 4340.217 | 4352.17 |
| 4352.32 | 4360.815 | 4369.31 |
| 4369.611 | 4380.962 | 4392.314 |
| 4393.817 | 4408.627 | 4423.436 |
| 4424.789 | 4431.179 | 4437.569 |
| 4437.87 | 4459.22 | 4480.57 |
| 4496.507 | 4506.58 | 4516.654 |
| 4552.738 | 4564.991 | 4577.245 |
| 4577.384 | 4592.602 | 4607.819 |
| 4616.938 | 4625.282 | 4633.627 |
| 4633.927 | 4643.324 | 4652.721 |
| 4664.148 | 4675.274 | 4686.4 |
| 4690.609 | 4717.673 | 4744.736 |
| 4746.54 | 4756.162 | 4765.785 |
| 4766.386 | 4773.152 | 4779.918 |
| 4780.218 | 4791.194 | 4802.17 |
| 4802.621 | 4817.881 | 4833.142 |
| 4836.299 | 4855.995 | 4875.691 |
| 4880.953 | 4891.177 | 4901.401 |
| 4909.52 | 4918.316 | 4927.111 |
| 4927.261 | 4937.636 | 4948.01 |
| 4948.16 | 4963.045 | 4977.93 |
| 4987.552 | 4998.979 | 5010.405 |
| 5011.007 | 5020.103 | 5029.199 |
| 5029.65 | 5041.077 | 5052.504 |
| 5053.556 | 5067.839 | 5082.123 |
| 5087.535 | 5104.074 | 5120.613 |
| 5121.383 | 5134.355 | 5147.326 |
| 5149.837 | 5156.322 | 5162.808 |
| 5164.9 | 5181.637 | 5198.375 |
| 5209.77 | 5223.753 | 5237.736 |
| 5238.036 | 5247.734 | 5257.432 |
| 5275.624 | 5289.757 | 5303.89 |
| 5347.191 | 5358.543 | 5369.894 |
| 5370.646 | 5377.186 | 5383.726 |
| 5383.877 | 5389.815 | 5395.754 |
| 5395.905 | 5403.422 | 5410.94 |
| 5411.09 | 5416.277 | 5421.464 |
| 5421.615 | 5429.809 | 5438.003 |
| 5439.807 | 5449.204 | 5458.601 |
| 5463.713 | 5472.057 | 5480.402 |
| 5481.454 | 5495.813 | 5510.171 |
| 5510.472 | 5521.222 | 5531.972 |
| 5535.439 | 5557.829 | 5580.219 |
| 5663.828 | 5675.387 | 5686.946 |
| 5696.097 | 5709.823 | 5723.549 |
| 5740.923 | 5748.044 | 5755.165 |
| 5756.127 | 5762.381 | 5768.636 |
| 5769.502 | 5776.671 | 5783.84 |
| 5787.496 | 5795.483 | 5803.469 |
| 5803.95 | 5815.979 | 5828.007 |
| 5828.68 | 5842.055 | 5855.431 |
| 5856.297 | 5867.218 | 5878.14 |
| 5879.39 | 5889.157 | 5898.924 |
| 5899.02 | 5910.808 | 5922.595 |
| 5924.106 | 5934.47 | 5944.834 |
| 5946.068 | 5961.861 | 5977.654 |
| 5978.694 | 5997.458 | 6016.222 |
| 6016.895 | 6026.806 | 6036.717 |
| 6052.178 | 6074.758 | 6097.337 |
| 6099.552 | 6108.597 | 6117.642 |
| 6161.136 | 6170.373 | 6179.611 |
| 6184.807 | 6192.938 | 6201.069 |
| 6201.261 | 6209.585 | 6217.908 |
| 6218.004 | 6226.039 | 6234.074 |
| 6245.993 | 6254.58 | 6263.166 |
| 6273.718 | 6283.244 | 6292.771 |
| 6292.867 | 6301.238 | 6309.61 |
| 6321.927 | 6331.742 | 6341.556 |
| 6349.371 | 6357.324 | 6365.277 |
| 6379.18 | 6386.108 | 6393.037 |
| 6393.229 | 6399.965 | 6406.7 |

| Left m/z | Center m/z | Right m/z |
|---|---|---|
| 6408.625 | 6437.829 | 6467.033 |
| 6467.129 | 6485.171 | 6503.214 |
| 6520.161 | 6531.72 | 6543.279 |
| 6548.095 | 6556.042 | 6563.989 |
| 6577.691 | 6589.431 | 6601.17 |
| 6603.961 | 6611.61 | 6619.26 |
| 6620.319 | 6634.319 | 6648.32 |
| 6648.512 | 6657.076 | 6665.64 |
| 6668.623 | 6680.651 | 6692.68 |
| 6700.438 | 6707.101 | 6713.764 |
| 6719.237 | 6731.65 | 6744.063 |
| 6744.599 | 6755.677 | 6766.754 |
| 6767.638 | 6773.171 | 6778.704 |
| 6786.982 | 6792.762 | 6798.542 |
| 6799.97 | 6808.919 | 6817.868 |
| 6824.892 | 6836.679 | 6848.467 |
| 6848.948 | 6859.629 | 6870.31 |
| 6873.797 | 6881.433 | 6889.07 |
| 6890.609 | 6897.599 | 6904.589 |
| 6914.565 | 6921.586 | 6928.606 |
| 6933.102 | 6941.477 | 6949.853 |
| 6950.469 | 6956.75 | 6963.032 |
| 6963.34 | 6970.545 | 6977.75 |
| 6978.92 | 6992.222 | 7005.524 |
| 7014.269 | 7022.06 | 7029.85 |
| 7029.912 | 7034.592 | 7039.272 |
| 7039.395 | 7045.154 | 7050.912 |
| 7067.293 | 7073.79 | 7080.287 |
| 7119.824 | 7147.228 | 7174.633 |
| 7177.589 | 7188.951 | 7200.314 |
| 7232.783 | 7257.933 | 7283.084 |
| 7292.812 | 7300.633 | 7308.454 |
| 7316.187 | 7321.946 | 7327.705 |
| 7327.772 | 7333.817 | 7339.863 |
| 7339.896 | 7346.093 | 7352.29 |
| 7352.819 | 7360.754 | 7368.688 |
| 7379.768 | 7393.009 | 7406.249 |
| 7406.3 | 7419.793 | 7433.287 |
| 7433.608 | 7447.584 | 7461.56 |
| 7463.692 | 7479.362 | 7495.032 |
| 7497.824 | 7510.356 | 7522.889 |
| 7731.041 | 7738.801 | 7746.561 |
| 7761.341 | 7779.077 | 7796.813 |
| 7808.996 | 7828.02 | 7847.044 |
| 7849.362 | 7871.424 | 7893.485 |
| 7904.954 | 7912.836 | 7920.719 |
| 8007.424 | 8015.07 | 8022.717 |
| 8134.028 | 8157.158 | 8180.287 |
| 8195.752 | 8206.991 | 8218.23 |
| 8238.737 | 8253.917 | 8269.098 |
| 8304.472 | 8328.669 | 8352.866 |
| 8353.406 | 8363.536 | 8373.667 |
| 8380.133 | 8391.495 | 8402.857 |
| 8404.767 | 8413.388 | 8422.01 |
| 8422.133 | 8430.231 | 8438.33 |
| 8457.421 | 8464.072 | 8470.723 |
| 8470.846 | 8477.558 | 8484.271 |
| 8497.292 | 8508.651 | 8520.011 |
| 8520.544 | 8531.198 | 8541.852 |
| 8554.723 | 8564.761 | 8574.799 |
| 8575.476 | 8585.268 | 8595.06 |
| 8618.77 | 8631.702 | 8644.635 |
| 8649.87 | 8660.554 | 8671.239 |
| 8671.855 | 8696.119 | 8720.383 |
| 8720.568 | 8728.512 | 8736.456 |
| 8736.518 | 8745.817 | 8755.116 |
| 8756.348 | 8770.604 | 8784.861 |
| 8791.574 | 8796.962 | 8802.351 |
| 8802.474 | 8822.181 | 8841.887 |
| 8861.964 | 8871.848 | 8881.732 |
| 8883.826 | 8890.538 | 8897.251 |
| 8897.436 | 8901.654 | 8905.873 |
| 8905.934 | 8928.258 | 8950.582 |
| 8967.272 | 8974.415 | 8981.559 |
| 8988.149 | 8997.971 | 9007.794 |
| 9010.011 | 9020.295 | 9030.58 |
| 9030.764 | 9038.216 | 9045.668 |

| Left m/z | Center m/z | Right m/z |
|---|---|---|
| 9055.367 | 9062.134 | 9068.902 |
| 9069.184 | 9079.194 | 9089.205 |
| 9091.547 | 9097.798 | 9104.049 |
| 9115.171 | 9134.336 | 9153.501 |
| 9196.082 | 9206.437 | 9216.792 |
| 9217.991 | 9226.317 | 9234.643 |
| 9234.742 | 9244.546 | 9254.35 |
| 9254.941 | 9263.932 | 9272.924 |
| 9273.256 | 9291.73 | 9310.203 |
| 9310.761 | 9318.865 | 9326.969 |
| 9344.962 | 9359.289 | 9373.615 |
| 9387.662 | 9395.293 | 9402.923 |
| 9410.817 | 9430.014 | 9449.211 |
| 9475.524 | 9484.41 | 9493.296 |
| 9494.536 | 9504.042 | 9513.549 |
| 9520.898 | 9534.803 | 9548.707 |
| 9559.484 | 9576.179 | 9592.874 |
| 9615.006 | 9641.179 | 9667.352 |
| 9689.387 | 9720.901 | 9752.414 |
| 9784.265 | 9793.021 | 9801.777 |
| 9840.895 | 9862.594 | 9884.294 |
| 9908.49 | 9918.931 | 9929.371 |
| 9929.66 | 9941.495 | 9953.331 |
| 10002.41 | 10012.36 | 10022.32 |
| 10066.88 | 10079.24 | 10091.61 |
| 10091.7 | 10102.24 | 10112.77 |
| 10120.09 | 10135.29 | 10150.49 |
| 10150.78 | 10162.62 | 10174.45 |
| 10174.65 | 10185.23 | 10195.82 |
| 10195.91 | 10210.35 | 10224.78 |
| 10225.16 | 10236.04 | 10246.91 |
| 10250.09 | 10263.03 | 10275.97 |
| 10276.55 | 10285.11 | 10293.68 |
| 10295 | 10313.15 | 10331.3 |
| 10333.03 | 10346.26 | 10359.49 |
| 10359.69 | 10365.85 | 10372 |
| 10408.98 | 10420.87 | 10432.75 |
| 10436.76 | 10448.55 | 10460.34 |
| 10472.41 | 10480.21 | 10488.01 |
| 10488.32 | 10503.84 | 10519.36 |
| 10521.66 | 10532.67 | 10543.68 |
| 10543.99 | 10551.18 | 10558.36 |
| 10573.66 | 10589.18 | 10604.71 |
| 10615.84 | 10636.81 | 10657.79 |
| 10705.55 | 10734.07 | 10762.59 |
| 10773.07 | 10782.59 | 10792.12 |
| 10792.19 | 10804.96 | 10817.72 |
| 10827.72 | 10846.77 | 10865.83 |
| 10912.98 | 10923.56 | 10934.15 |
| 10954.02 | 10965.58 | 10977.14 |
| 11035.47 | 11057.93 | 11080.38 |
| 11092.07 | 11107.19 | 11122.31 |
| 11137.08 | 11149.06 | 11161.04 |
| 11288.09 | 11306.44 | 11324.78 |
| 11357.26 | 11375.9 | 11394.54 |
| 11396.27 | 11410.09 | 11423.9 |
| 11425.13 | 11447.54 | 11469.96 |
| 11505.19 | 11532.05 | 11558.92 |
| 11613 | 11627.24 | 11641.47 |
| 11642.18 | 11654.28 | 11666.38 |
| 11666.74 | 11688.44 | 11710.15 |
| 11712.08 | 11733.43 | 11754.78 |
| 11756.23 | 11786.66 | 11817.09 |
| 11817.93 | 11834.77 | 11851.61 |
| 11868.93 | 11898.52 | 11928.11 |
| 11928.7 | 11944.87 | 11961.05 |
| 12143.52 | 12158.28 | 12173.04 |
| 12271.47 | 12290.85 | 12310.22 |
| 12400.43 | 12412.62 | 12424.81 |
| 12433.83 | 12457.39 | 12480.94 |
| 12489.93 | 12507.27 | 12524.61 |
| 12536.4 | 12565.8 | 12595.2 |
| 12597.2 | 12613.41 | 12629.61 |
| 12647.98 | 12674.21 | 12700.44 |
| 12716.47 | 12738.02 | 12759.57 |
| 12761.24 | 12785.79 | 12810.35 |
| 12829.73 | 12873.16 | 12916.59 |

-continued

| Left m/z | Center m/z | Right m/z |
|---|---|---|
| 12935.63 | 12967.54 | 12999.44 |
| 13051.23 | 13080.96 | 13110.69 |
| 13117.71 | 13134.41 | 13151.12 |
| 13225.86 | 13241.27 | 13256.68 |
| 13258.69 | 13274.73 | 13290.77 |
| 13304.99 | 13318.16 | 13331.32 |
| 13347.56 | 13364.6 | 13381.64 |
| 13402.57 | 13413.92 | 13425.28 |
| 13510.26 | 13524.96 | 13539.66 |
| 13551.35 | 13567.72 | 13584.09 |
| 13597.13 | 13624.17 | 13651.21 |
| 13703.7 | 13721.07 | 13738.44 |
| 13740.45 | 13762.16 | 13783.88 |
| 13784.55 | 13798.24 | 13811.94 |
| 13826.64 | 13842.84 | 13859.05 |
| 13864.06 | 13882.93 | 13901.81 |
| 13903.15 | 13916.01 | 13928.87 |
| 13929.87 | 13943.07 | 13956.27 |
| 13958.61 | 13983.66 | 14008.72 |
| 14015.73 | 14042.8 | 14069.86 |
| 14076.2 | 14097.59 | 14118.97 |
| 14124.31 | 14149.03 | 14173.76 |
| 14178.77 | 14198.98 | 14219.19 |
| 14231.55 | 14254.61 | 14277.66 |
| 14281.33 | 14306.56 | 14331.78 |
| 14461.45 | 14515 | 14568.55 |
| 14751.73 | 14784.47 | 14817.21 |
| 14857.63 | 14884.53 | 14911.42 |
| 14949.73 | 14975.44 | 15001.15 |
| 15009.14 | 15028.79 | 15048.44 |
| 15527.48 | 15563.22 | 15598.97 |
| 15713.63 | 15753.95 | 15794.27 |
| 16465.93 | 16502.17 | 16538.42 |
| 16610.92 | 16630.13 | 16649.34 |
| 16999.46 | 17032.54 | 17065.61 |
| 17104.03 | 17148.13 | 17192.23 |
| 17225.64 | 17270.91 | 17316.18 |
| 17318.65 | 17335.6 | 17352.55 |
| 17359.48 | 17401.7 | 17443.93 |
| 17445.13 | 17476.37 | 17507.61 |
| 17569.08 | 17604.33 | 17639.57 |
| 17774.54 | 17815.47 | 17856.39 |
| 17982.34 | 18031.12 | 18079.9 |
| 18232.58 | 18275.34 | 18318.1 |
| 18593.72 | 18636.99 | 18680.25 |
| 18816.22 | 18850.13 | 18884.04 |
| 19339.07 | 19373.15 | 19407.22 |
| 19407.56 | 19463.85 | 19520.15 |
| 19522.82 | 19575.27 | 19627.72 |
| 20740.85 | 20811.99 | 20883.14 |
| 20886.89 | 20945.69 | 21004.49 |
| 21005.16 | 21061.95 | 21118.75 |
| 21119.42 | 21170.37 | 21221.31 |
| 21221.98 | 21275.44 | 21328.89 |
| 21330.89 | 21377.17 | 21423.44 |
| 21428.09 | 21475.32 | 21522.55 |
| 21642.26 | 21687.7 | 21733.13 |
| 21733.61 | 21755.74 | 21777.87 |
| 21778.15 | 21807.79 | 21837.44 |
| 21837.72 | 21862.69 | 21887.65 |
| 21887.93 | 21917.15 | 21946.37 |
| 22967.23 | 23036.05 | 23104.87 |
| 23110.29 | 23160.86 | 23211.44 |
| 23212.98 | 23256.28 | 23299.59 |
| 23407.68 | 23468.85 | 23530.03 |
| 27630.18 | 27715.9 | 27801.62 |
| 27874.33 | 27944.17 | 28014.01 |
| 28015.03 | 28082.32 | 28149.61, | a set of mass spectrometry feature values for a constitutive set for classification, the set of mass spectrometry feature values obtained from blood-based samples of prostate cancer patients, a classification algorithm and a set of logistic regression weighting coefficients derived from a combination of filtered mini-classifiers with dropout regularization; the computer system including program code for executing the final classifier on a set of mass spectrometry feature values obtained from mass spectrometry of a blood-based sample of a human with prostate cancer.

2. The computer system of claim 1, wherein non-mass spectral information for each prostate cancer patient whose blood-based samples are in the constitutive set is stored in the memory, including at least one of age, PSA and % fPSA.

3. The computer system of claim 1, wherein each prostate cancer patient whose sample is a member of the constitutive set supplied the sample after diagnosis with prostate cancer but before radical prostatectomy (RPE).

4. The computer system of claim 1, wherein each prostate cancer patient whose sample is a member of the constitutive set has a Total Gleason Score of 6 or lower at the time the blood-based sample from such patient was obtained.

5. A laboratory test system for conducting a test on a blood-based sample from a prostate cancer patient to predict aggressiveness or indolence of the prostate cancer comprising, in combination:
a mass spectrometer conducting mass spectrometry of the blood-based sample with a mass spectrometer and thereby obtaining mass spectral data including intensity values at a multitude of m/z features in a spectrum produced by the mass spectrometer; and
a programmed computer including code for performing pre-processing operations on the mass spectral data and classifying the sample with a final classifier defined by one or more master classifiers generated as a combination of filtered mini-classifiers with regularization, the final classifier operating on the intensity values of the sample after the pre-processing operations are performed and a set of stored values of m/z features from a constitutive set of mass spectra obtained from blood-based samples of prostate cancer patients, wherein the m/z features are selected from the list of features comprising those shown below:

| Left m/z | Center m/z | Right m/z |
|---|---|---|
| 3081.583 | 3090.249 | 3098.915 |
| 3308.621 | 3329.648 | 3350.675 |
| 4145.045 | 4160.911 | 4176.776 |
| 4177.923 | 4197.23 | 4216.536 |
| 4446.822 | 4468.04 | 4489.258 |
| 4556.927 | 4572.41 | 4587.894 |
| 4694.939 | 4717.304 | 4739.669 |
| 4772.094 | 4790.636 | 4809.178 |
| 4809.56 | 4824.661 | 4839.762 |
| 4846.644 | 4860.598 | 4874.552 |
| 4880.493 | 4896.55 | 4912.607 |
| 5053.678 | 5071.264 | 5088.85 |
| 5090.762 | 5109.303 | 5127.845 |
| 5279.182 | 5292.874 | 5306.565 |
| 6376.924 | 6430.949 | 6484.973 |
| 6576.342 | 6590.984 | 6605.625 |
| 6606.408 | 6652.759 | 6699.111 |
| 6782.803 | 6797.117 | 6811.43 |
| 6822.441 | 6835.653 | 6848.866 |
| 6849.6 | 6859.632 | 6869.663 |
| 6870.397 | 6891.073 | 6911.748 |
| 6928.141 | 6946.736 | 6965.332 |
| 7018.671 | 7055.25 | 7091.829 |
| 7370.816 | 7387.447 | 7404.077 |
| 7405.224 | 7419.56 | 7433.897 |
| 7514.946 | 7556.617 | 7598.289 |
| 7658.311 | 7681.058 | 7703.805 |
| 7893.703 | 7945.124 | 7996.544 |
| 7999.22 | 8034.583 | 8069.947 |
| 8181.751 | 8209.468 | 8237.185 |
| 8551.43 | 8562.293 | 8573.157 |

129
-continued

| Left m/z | Center m/z | Right m/z |
|---|---|---|
| 8574.723 | 8589.795 | 8604.867 |
| 8666.721 | 8691.776 | 8716.831 |
| 8730.019 | 8759.869 | 8789.72 |
| 8792.411 | 8818.347 | 8844.283 |
| 8859.941 | 8870.798 | 8881.656 |
| 8883.796 | 8923.25 | 8962.704 |
| 9043.529 | 9067.232 | 9090.935 |
| 9092.465 | 9154.245 | 9216.026 |
| 9265.334 | 9282.308 | 9299.283 |
| 9324.362 | 9346.077 | 9367.792 |
| 9368.098 | 9381.861 | 9395.624 |
| 9398.071 | 9433.855 | 9469.639 |
| 9471.168 | 9487.836 | 9504.505 |
| 9617.762 | 9641.159 | 9664.556 |
| 9690.553 | 9717.467 | 9744.382 |
| 9777.537 | 9793.747 | 9809.957 |
| 9902.628 | 9935.506 | 9968.385 |
| 10325.87 | 10347.13 | 10368.38 |
| 10430.11 | 10453.51 | 10476.9 |
| 11502.59 | 11525.29 | 11547.99 |
| 11642.19 | 11673.55 | 11704.91 |
| 11709.09 | 11730.3 | 11751.51 |
| 12525.06 | 12571.66 | 12618.25 |
| 12808.63 | 12864.18 | 12919.74 |
| 13676.71 | 13706.17 | 13735.63 |
| 13737.77 | 13758.42 | 13779.07 |
| 13781.02 | 13797.76 | 13814.5 |
| 13825.46 | 13839.55 | 13853.64 |
| 13855.09 | 13877.11 | 13899.13 |
| 13899.72 | 13913.81 | 13927.91 |
| 13928.52 | 13939.29 | 13950.05 |
| 13958.08 | 13970.19 | 13982.3 |
| 14026.12 | 14041.39 | 14056.66 |
| 14056.69 | 14066.96 | 14077.23 |
| 14612.46 | 14676.26 | 14740.06 |
| 15010.07 | 15126.44 | 15242.8 |
| 15269.09 | 15291.55 | 15314.01 |
| 15315.44 | 15345.55 | 15375.65 |
| 15724.22 | 15852.06 | 15979.89 |
| 16008.09 | 16031.26 | 16054.44 |
| 16056.83 | 16093.15 | 16129.47 |
| 16605.01 | 16682.66 | 16760.32 |
| 17091.97 | 17138.56 | 17185.16 |
| 17223.02 | 17266.27 | 17309.52 |
| 17333.41 | 17393.86 | 17454.31 |
| 17563.93 | 17601.92 | 17639.91 |
| 18598.12 | 18640.3 | 18682.49 |
| 21007.96 | 21074.42 | 21140.87 |
| 21949.42 | 22238.76 | 22528.1 |
| 27742.59 | 27978.55 | 28214.5 |
| 28227.94 | 28314.56 | 28401.17 |
| 28793.87 | 28909.23 | 29024.6 |
| 29572.29 | 29667.12 | 29761.95 |
| 3153.208 | 3164.868 | 3176.529 |
| 3353.837 | 3372.531 | 3391.224 |
| 3419.727 | 3442.492 | 3465.257 |
| 3473.03 | 3490.798 | 3508.566 |
| 4055.23 | 4068.741 | 4082.252 |
| 4137.036 | 4153.693 | 4170.351 |
| 4170.721 | 4190.155 | 4209.588 |
| 4698.8 | 4712.168 | 4725.537 |
| 4759.221 | 4802.16 | 4845.099 |
| 4983.911 | 5008.526 | 5033.142 |
| 5053.501 | 5069.418 | 5085.336 |
| 5090.443 | 5104.695 | 5118.946 |
| 5121.167 | 5133.938 | 5146.708 |
| 5525.044 | 5570.204 | 5615.365 |
| 5843.444 | 5879.72 | 5915.996 |
| 5978.924 | 6000.949 | 6022.974 |
| 6366.989 | 6387.348 | 6407.707 |
| 6409.047 | 6457.28 | 6505.514 |
| 6518.615 | 6532 | 6545.385 |
| 6623.863 | 6631.566 | 6639.268 |
| 6566.766 | 6632.507 | 6698.248 |
| 6785.31 | 6794.313 | 6803.315 |
| 6826.591 | 6838.081 | 6849.57 |
| 6850.447 | 6859.449 | 6868.452 |

130
-continued

| Left m/z | Center m/z | Right m/z |
|---|---|---|
| 6870.181 | 6882.263 | 6894.346 |
| 6916.615 | 6940.779 | 6964.943 |
| 7459.185 | 7488.68 | 7518.175 |
| 7526.229 | 7562.357 | 7598.486 |
| 7601.624 | 7617.379 | 7633.133 |
| 7657.771 | 7674.354 | 7690.938 |
| 7887.538 | 7929.737 | 7971.936 |
| 7976.674 | 7990.148 | 8003.622 |
| 8005.695 | 8033.827 | 8061.96 |
| 8188.822 | 8205.257 | 8221.693 |
| 8226.727 | 8238.276 | 8249.825 |
| 8651.726 | 8684.856 | 8717.985 |
| 8726.499 | 8759.074 | 8791.648 |
| 8797.941 | 8827.554 | 8857.167 |
| 8887.061 | 8931.11 | 8975.16 |
| 9041.789 | 9061.223 | 9080.657 |
| 9084.787 | 9147.53 | 9210.273 |
| 9281.714 | 9303.369 | 9325.024 |
| 9329.466 | 9346.308 | 9363.151 |
| 9366.482 | 9382.584 | 9398.686 |
| 9400.788 | 9437.805 | 9474.821 |
| 9623.278 | 9643.606 | 9663.934 |
| 9693.159 | 9709.261 | 9725.363 |
| 9727.954 | 9747.388 | 9766.821 |
| 9917.122 | 9933.965 | 9950.807 |
| 10045.12 | 10073.81 | 10102.5 |
| 10130.62 | 10227.42 | 10324.21 |
| 10326.06 | 10342.54 | 10359.01 |
| 10409.79 | 10460.69 | 10511.59 |
| 10610.05 | 10649.29 | 10688.53 |
| 10778.11 | 10838.26 | 10898.41 |
| 11501.77 | 11535.78 | 11569.79 |
| 11653.08 | 11680.38 | 11707.67 |
| 11713.23 | 11736.36 | 11759.5 |
| 12524.61 | 12570.59 | 12616.58 |
| 12768.69 | 12848.51 | 12928.32 |
| 13256.1 | 13278.08 | 13300.06 |
| 13490.6 | 13556.3 | 13622.01 |
| 13660.37 | 13699.01 | 13737.65 |
| 13740.89 | 13760.09 | 13779.29 |
| 13781.6 | 13794.79 | 13807.98 |
| 13825.56 | 13840.37 | 13855.17 |
| 13857.95 | 13878.31 | 13898.67 |
| 13901.91 | 13915.09 | 13928.28 |
| 13928.74 | 13942.62 | 13956.51 |
| 13960.21 | 13979.18 | 13998.15 |
| 14020.82 | 14048.12 | 14075.42 |
| 14078.2 | 14103.42 | 14128.63 |
| 14130.48 | 14156.63 | 14182.77 |
| 14339.49 | 14402.65 | 14465.81 |
| 14830.89 | 14885.25 | 14939.62 |
| 14941.47 | 14989.6 | 15037.72 |
| 15039.57 | 15067.33 | 15095.09 |
| 15096.02 | 15155.01 | 15214.01 |
| 15270.23 | 15291.74 | 15313.26 |
| 15314.65 | 15346.57 | 15378.5 |
| 15705.12 | 15736.59 | 15768.05 |
| 15769.44 | 15801.13 | 15832.83 |
| 15833.76 | 15867.07 | 15900.39 |
| 15901.31 | 15925.14 | 15948.97 |
| 15951.75 | 15981.59 | 16011.43 |
| 16014.21 | 16034.34 | 16054.47 |
| 16055.85 | 16088.94 | 16122.02 |
| 16125.23 | 16148 | 16170.78 |
| 16175.11 | 16204.76 | 16234.4 |
| 16600.22 | 16666.38 | 16732.53 |
| 17222.34 | 17246.92 | 17271.5 |
| 17272.23 | 17288.13 | 17304.04 |
| 17358.26 | 17377.42 | 17396.58 |
| 17398.03 | 17417.91 | 17437.79 |
| 17852.61 | 17901.41 | 17950.21 |
| 18594.98 | 18622.82 | 18650.65 |
| 18652.82 | 18677.4 | 18701.98 |
| 20902.69 | 20954.66 | 21006.62 |
| 21011.14 | 21064.46 | 21117.78 |
| 23258.31 | 23571.9 | 23885.49 |
| 27660.21 | 27839.26 | 28018.31 |

| Left m/z | Center m/z | Right m/z | | Left m/z | Center m/z | Right m/z |
|---|---|---|---|---|---|---|
| 28019.44 | 28098.51 | 28177.59 | | 5439.807 | 5449.204 | 5458.601 |
| 28227.29 | 28315.97 | 28404.65 | | 5463.713 | 5472.057 | 5480.402 |
| 28815.5 | 28888.93 | 28962.36 | | 5481.454 | 5495.813 | 5510.171 |
| 3073.625 | 3085.665 | 3097.705 | | 5510.472 | 5521.222 | 5531.972 |
| 3098.586 | 3109.891 | 3121.197 | | 5535.439 | 5557.829 | 5580.219 |
| 3123.546 | 3138.669 | 3153.793 | | 5663.828 | 5675.387 | 5686.946 |
| 3190.793 | 3210.615 | 3230.436 | | 5696.097 | 5709.823 | 5723.549 |
| 3230.73 | 3242.623 | 3254.516 | | 5740.923 | 5748.044 | 5755.165 |
| 3255.103 | 3264.647 | 3274.191 | | 5756.127 | 5762.381 | 5768.636 |
| 3296.802 | 3316.77 | 3336.739 | | 5769.502 | 5776.671 | 5783.84 |
| 3349.072 | 3363.608 | 3378.144 | | 5787.496 | 5795.483 | 5803.469 |
| 3380.2 | 3391.946 | 3403.692 | | 5803.95 | 5815.979 | 5828.007 |
| 3405.16 | 3420.283 | 3435.407 | | 5828.68 | 5842.055 | 5855.431 |
| 3435.7 | 3445.097 | 3454.494 | | 5856.297 | 5867.218 | 5878.14 |
| 3454.788 | 3465.359 | 3475.931 | | 5879.39 | 5889.157 | 5898.924 |
| 3490.725 | 3508.305 | 3525.884 | | 5899.02 | 5910.808 | 5922.595 |
| 3531.431 | 3553.896 | 3576.36 | | 5924.106 | 5934.47 | 5944.834 |
| 3581.059 | 3593.099 | 3605.138 | | 5946.068 | 5961.861 | 5977.654 |
| 3665.631 | 3679.286 | 3692.941 | | 5978.694 | 5997.458 | 6016.222 |
| 3693.94 | 3712.036 | 3730.132 | | 6016.895 | 6026.806 | 6036.717 |
| 3745.211 | 3754.755 | 3764.299 | | 6052.178 | 6074.758 | 6097.337 |
| 3764.592 | 3775.604 | 3786.616 | | 6099.552 | 6108.597 | 6117.642 |
| 3798.592 | 3814.263 | 3829.933 | | 6161.136 | 6170.373 | 6179.611 |
| 3831.545 | 3841.53 | 3851.514 | | 6184.807 | 6192.938 | 6201.069 |
| 3876.474 | 3887.486 | 3898.499 | | 6201.261 | 6209.585 | 6217.908 |
| 3898.583 | 3906.18 | 3913.777 | | 6218.004 | 6226.039 | 6234.074 |
| 3914.356 | 3928.158 | 3941.959 | | 6245.993 | 6254.58 | 6263.166 |
| 3942.253 | 3953.412 | 3964.571 | | 6273.718 | 6283.244 | 6292.771 |
| 3994.23 | 4008.619 | 4023.008 | | 6292.867 | 6301.238 | 6309.61 |
| 4024.182 | 4031.67 | 4039.159 | | 6321.927 | 6331.742 | 6341.556 |
| 4039.452 | 4050.464 | 4061.476 | | 6349.371 | 6357.324 | 6365.277 |
| 4086.437 | 4098.77 | 4111.104 | | 6379.18 | 6386.108 | 6393.037 |
| 4111.308 | 4118.525 | 4125.742 | | 6393.229 | 6399.965 | 6406.7 |
| 4126.043 | 4133.109 | 4140.176 | | 6408.625 | 6437.829 | 6467.033 |
| 4198.812 | 4209.788 | 4220.764 | | 6467.129 | 6485.171 | 6503.214 |
| 4241.573 | 4249.445 | 4257.316 | | 6520.161 | 6531.72 | 6543.279 |
| 4258.28 | 4265.83 | 4273.38 | | 6548.095 | 6556.042 | 6563.989 |
| 4273.837 | 4286.166 | 4298.495 | | 6577.691 | 6589.431 | 6601.17 |
| 4328.264 | 4340.217 | 4352.17 | | 6603.961 | 6611.61 | 6619.26 |
| 4352.32 | 4360.815 | 4369.31 | | 6620.319 | 6634.319 | 6648.32 |
| 4369.611 | 4380.962 | 4392.314 | | 6648.512 | 6657.076 | 6665.64 |
| 4393.817 | 4408.627 | 4423.436 | | 6668.623 | 6680.651 | 6692.68 |
| 4424.789 | 4431.179 | 4437.569 | | 6700.438 | 6707.101 | 6713.764 |
| 4437.87 | 4459.22 | 4480.57 | | 6719.237 | 6731.65 | 6744.063 |
| 4496.507 | 4506.58 | 4516.654 | | 6744.599 | 6755.677 | 6766.754 |
| 4552.738 | 4564.991 | 4577.245 | | 6767.638 | 6773.171 | 6778.704 |
| 4577.384 | 4592.602 | 4607.819 | | 6786.982 | 6792.762 | 6798.542 |
| 4616.938 | 4625.282 | 4633.627 | | 6799.97 | 6808.919 | 6817.868 |
| 4633.927 | 4643.324 | 4652.721 | | 6824.892 | 6836.679 | 6848.467 |
| 4664.148 | 4675.274 | 4686.4 | | 6848.948 | 6859.629 | 6870.31 |
| 4690.609 | 4717.673 | 4744.736 | | 6873.797 | 6881.433 | 6889.07 |
| 4746.54 | 4756.162 | 4765.785 | | 6890.609 | 6897.599 | 6904.589 |
| 4766.386 | 4773.152 | 4779.918 | | 6914.565 | 6921.586 | 6928.606 |
| 4780.218 | 4791.194 | 4802.17 | | 6933.102 | 6941.477 | 6949.853 |
| 4802.621 | 4817.881 | 4833.142 | | 6950.469 | 6956.75 | 6963.032 |
| 4836.299 | 4855.995 | 4875.691 | | 6963.34 | 6970.545 | 6977.75 |
| 4880.953 | 4891.177 | 4901.401 | | 6978.92 | 6992.222 | 7005.524 |
| 4909.52 | 4918.316 | 4927.111 | | 7014.269 | 7022.06 | 7029.85 |
| 4927.261 | 4937.636 | 4948.01 | | 7029.912 | 7034.592 | 7039.272 |
| 4948.16 | 4963.045 | 4977.93 | | 7039.395 | 7045.154 | 7050.912 |
| 4987.552 | 4998.979 | 5010.405 | | 7067.293 | 7073.79 | 7080.287 |
| 5011.007 | 5020.103 | 5029.199 | | 7119.824 | 7147.228 | 7174.633 |
| 5029.65 | 5041.077 | 5052.504 | | 7177.589 | 7188.951 | 7200.314 |
| 5053.556 | 5067.839 | 5082.123 | | 7232.783 | 7257.933 | 7283.084 |
| 5087.535 | 5104.074 | 5120.613 | | 7292.812 | 7300.633 | 7308.454 |
| 5121.383 | 5134.355 | 5147.326 | | 7316.187 | 7321.946 | 7327.705 |
| 5149.837 | 5156.322 | 5162.808 | | 7327.772 | 7333.817 | 7339.863 |
| 5164.9 | 5181.637 | 5198.375 | | 7339.896 | 7346.093 | 7352.29 |
| 5209.77 | 5223.753 | 5237.736 | | 7352.819 | 7360.754 | 7368.688 |
| 5238.036 | 5247.734 | 5257.432 | | 7379.768 | 7393.009 | 7406.249 |
| 5275.624 | 5289.757 | 5303.89 | | 7406.3 | 7419.793 | 7433.287 |
| 5347.191 | 5358.543 | 5369.894 | | 7433.608 | 7447.584 | 7461.56 |
| 5370.646 | 5377.186 | 5383.726 | | 7463.692 | 7479.362 | 7495.032 |
| 5383.877 | 5389.815 | 5395.754 | | 7497.824 | 7510.356 | 7522.889 |
| 5395.905 | 5403.422 | 5410.94 | | 7731.041 | 7738.801 | 7746.561 |
| 5411.09 | 5416.277 | 5421.464 | | 7761.341 | 7779.077 | 7796.813 |
| 5421.615 | 5429.809 | 5438.003 | | 7808.996 | 7828.02 | 7847.044 |

| Left m/z | Center m/z | Right m/z |
| --- | --- | --- |
| 7849.362 | 7871.424 | 7893.485 |
| 7904.954 | 7912.836 | 7920.719 |
| 8007.424 | 8015.07 | 8022.717 |
| 8134.028 | 8157.158 | 8180.287 |
| 8195.752 | 8206.991 | 8218.23 |
| 8238.737 | 8253.917 | 8269.098 |
| 8304.472 | 8328.669 | 8352.866 |
| 8353.406 | 8363.536 | 8373.667 |
| 8380.133 | 8391.495 | 8402.857 |
| 8404.767 | 8413.388 | 8422.01 |
| 8422.133 | 8430.231 | 8438.33 |
| 8457.421 | 8464.072 | 8470.723 |
| 8470.846 | 8477.558 | 8484.271 |
| 8497.292 | 8508.651 | 8520.011 |
| 8520.544 | 8531.198 | 8541.852 |
| 8554.723 | 8564.761 | 8574.799 |
| 8575.476 | 8585.268 | 8595.06 |
| 8618.77 | 8631.702 | 8644.635 |
| 8649.87 | 8660.554 | 8671.239 |
| 8671.855 | 8696.119 | 8720.383 |
| 8720.568 | 8728.512 | 8736.456 |
| 8736.518 | 8745.817 | 8755.116 |
| 8756.348 | 8770.604 | 8784.861 |
| 8791.574 | 8796.962 | 8802.351 |
| 8802.474 | 8822.181 | 8841.887 |
| 8861.964 | 8871.848 | 8881.732 |
| 8883.826 | 8890.538 | 8897.251 |
| 8897.436 | 8901.654 | 8905.873 |
| 8905.934 | 8928.258 | 8950.582 |
| 8967.272 | 8974.415 | 8981.559 |
| 8988.149 | 8997.971 | 9007.794 |
| 9010.011 | 9020.295 | 9030.58 |
| 9030.764 | 9038.216 | 9045.668 |
| 9055.367 | 9062.134 | 9068.902 |
| 9069.184 | 9079.194 | 9089.205 |
| 9091.547 | 9097.798 | 9104.049 |
| 9115.171 | 9134.336 | 9153.501 |
| 9196.082 | 9206.437 | 9216.792 |
| 9217.991 | 9226.317 | 9234.643 |
| 9234.742 | 9244.546 | 9254.35 |
| 9254.941 | 9263.932 | 9272.924 |
| 9273.256 | 9291.73 | 9310.203 |
| 9310.761 | 9318.865 | 9326.969 |
| 9344.962 | 9359.289 | 9373.615 |
| 9387.662 | 9395.293 | 9402.923 |
| 9410.817 | 9430.014 | 9449.211 |
| 9475.524 | 9484.41 | 9493.296 |
| 9494.536 | 9504.042 | 9513.549 |
| 9520.898 | 9534.803 | 9548.707 |
| 9559.484 | 9576.179 | 9592.874 |
| 9615.006 | 9641.179 | 9667.352 |
| 9689.387 | 9720.901 | 9752.414 |
| 9784.265 | 9793.021 | 9801.777 |
| 9840.895 | 9862.594 | 9884.294 |
| 9908.49 | 9918.931 | 9929.371 |
| 9929.66 | 9941.495 | 9953.331 |
| 10002.41 | 10012.36 | 10022.32 |
| 10066.88 | 10079.24 | 10091.61 |
| 10091.7 | 10102.24 | 10112.77 |
| 10120.09 | 10135.29 | 10150.49 |
| 10150.78 | 10162.62 | 10174.45 |
| 10174.65 | 10185.23 | 10195.82 |
| 10195.91 | 10210.35 | 10224.78 |
| 10225.16 | 10236.04 | 10246.91 |
| 10250.09 | 10263.03 | 10275.97 |
| 10276.55 | 10285.11 | 10293.68 |
| 10295 | 10313.15 | 10331.3 |
| 10333.03 | 10346.26 | 10359.49 |
| 10359.69 | 10365.85 | 10372 |
| 10408.98 | 10420.87 | 10432.75 |
| 10436.76 | 10448.55 | 10460.34 |
| 10472.41 | 10480.21 | 10488.01 |
| 10488.32 | 10503.84 | 10519.36 |
| 10521.66 | 10532.67 | 10543.68 |
| 10543.99 | 10551.18 | 10558.36 |
| 10573.66 | 10589.18 | 10604.71 |
| 10615.84 | 10636.81 | 10657.79 |

| Left m/z | Center m/z | Right m/z |
| --- | --- | --- |
| 10705.55 | 10734.07 | 10762.59 |
| 10773.07 | 10782.59 | 10792.12 |
| 10792.19 | 10804.96 | 10817.72 |
| 10827.72 | 10846.77 | 10865.83 |
| 10912.98 | 10923.56 | 10934.15 |
| 10954.02 | 10965.58 | 10977.14 |
| 11035.47 | 11057.93 | 11080.38 |
| 11092.07 | 11107.19 | 11122.31 |
| 11137.08 | 11149.06 | 11161.04 |
| 11288.09 | 11306.44 | 11324.78 |
| 11357.26 | 11375.9 | 11394.54 |
| 11396.27 | 11410.09 | 11423.9 |
| 11425.13 | 11447.54 | 11469.96 |
| 11505.19 | 11532.05 | 11558.92 |
| 11613 | 11627.24 | 11641.47 |
| 11642.18 | 11654.28 | 11666.38 |
| 11666.74 | 11688.44 | 11710.15 |
| 11712.08 | 11733.43 | 11754.78 |
| 11756.23 | 11786.66 | 11817.09 |
| 11817.93 | 11834.77 | 11851.61 |
| 11868.93 | 11898.52 | 11928.11 |
| 11928.7 | 11944.87 | 11961.05 |
| 12143.52 | 12158.28 | 12173.04 |
| 12271.47 | 12290.85 | 12310.22 |
| 12400.43 | 12412.62 | 12424.81 |
| 12433.83 | 12457.39 | 12480.94 |
| 12489.93 | 12507.27 | 12524.61 |
| 12536.4 | 12565.8 | 12595.2 |
| 12597.2 | 12613.41 | 12629.61 |
| 12647.98 | 12674.21 | 12700.44 |
| 12716.47 | 12738.02 | 12759.57 |
| 12761.24 | 12785.79 | 12810.35 |
| 12829.73 | 12873.16 | 12916.59 |
| 12935.63 | 12967.54 | 12999.44 |
| 13051.23 | 13080.96 | 13110.69 |
| 13117.71 | 13134.41 | 13151.12 |
| 13225.86 | 13241.27 | 13256.68 |
| 13258.69 | 13274.73 | 13290.77 |
| 13304.99 | 13318.16 | 13331.32 |
| 13347.56 | 13364.6 | 13381.64 |
| 13402.57 | 13413.92 | 13425.28 |
| 13510.26 | 13524.96 | 13539.66 |
| 13551.35 | 13567.72 | 13584.09 |
| 13597.13 | 13624.17 | 13651.21 |
| 13703.7 | 13721.07 | 13738.44 |
| 13740.45 | 13762.16 | 13783.88 |
| 13784.55 | 13798.24 | 13811.94 |
| 13826.64 | 13842.84 | 13859.05 |
| 13864.06 | 13882.93 | 13901.81 |
| 13903.15 | 13916.01 | 13928.87 |
| 13929.87 | 13943.07 | 13956.27 |
| 13958.61 | 13983.66 | 14008.72 |
| 14015.73 | 14042.8 | 14069.86 |
| 14076.2 | 14097.59 | 14118.97 |
| 14124.31 | 14149.03 | 14173.76 |
| 14178.77 | 14198.98 | 14219.19 |
| 14231.55 | 14254.61 | 14277.66 |
| 14281.33 | 14306.56 | 14331.78 |
| 14461.45 | 14515 | 14568.55 |
| 14751.73 | 14784.47 | 14817.21 |
| 14857.63 | 14884.53 | 14911.42 |
| 14949.73 | 14975.44 | 15001.15 |
| 15009.14 | 15028.79 | 15048.44 |
| 15527.48 | 15563.22 | 15598.97 |
| 15713.63 | 15753.95 | 15794.27 |
| 16465.93 | 16502.17 | 16538.42 |
| 16610.92 | 16630.13 | 16649.34 |
| 16999.46 | 17032.54 | 17065.61 |
| 17104.03 | 17148.13 | 17192.23 |
| 17225.64 | 17270.91 | 17316.18 |
| 17318.65 | 17335.6 | 17352.55 |
| 17359.48 | 17401.7 | 17443.93 |
| 17445.13 | 17476.37 | 17507.61 |
| 17569.08 | 17604.33 | 17639.57 |
| 17774.54 | 17815.47 | 17856.39 |
| 17982.34 | 18031.12 | 18079.9 |
| 18232.58 | 18275.34 | 18318.1 |

| Left m/z | Center m/z | Right m/z |
|---|---|---|
| 18593.72 | 18636.99 | 18680.25 |
| 18816.22 | 18850.13 | 18884.04 |
| 19339.07 | 19373.15 | 19407.22 |
| 19407.56 | 19463.85 | 19520.15 |
| 19522.82 | 19575.27 | 19627.72 |
| 20740.85 | 20811.99 | 20883.14 |
| 20886.89 | 20945.69 | 21004.49 |
| 21005.16 | 21061.95 | 21118.75 |
| 21119.42 | 21170.37 | 21221.31 |
| 21221.98 | 21275.44 | 21328.89 |
| 21330.89 | 21377.17 | 21423.44 |
| 21428.09 | 21475.32 | 21522.55 |
| 21642.26 | 21687.7 | 21733.13 |
| 21733.61 | 21755.74 | 21777.87 |
| 21778.15 | 21807.79 | 21837.44 |
| 21837.72 | 21862.69 | 21887.65 |
| 21887.93 | 21917.15 | 21946.37 |
| 22967.23 | 23036.05 | 23104.87 |
| 23110.29 | 23160.86 | 23211.44 |
| 23212.98 | 23256.28 | 23299.59 |
| 23407.68 | 23468.85 | 23530.03 |
| 27630.18 | 27715.9 | 27801.62 |
| 27874.33 | 27944.17 | 28014.01 |
| 28015.03 | 28082.32 | 28149.61; | the programmed computer producing a class label for the blood-based sample of High, Early or the equivalent signifying the patient is at high risk of early progression/relapse of the prostate cancer indicating aggressiveness of the prostate cancer, or Low, Late or the equivalent, signifying that the patient is at low risk of early progression/relapse of the prostate cancer indicating indolence of the cancer.

6. The system of claim 5, wherein the mass spectrum of the blood-based sample is obtained from at least 100,000 laser shots applied to the blood-based sample using MALDI-TOF mass spectrometry.

7. A programmed computer operating as a classifier for predicting prostate cancer aggressiveness or indolence, comprising a processing unit and a memory storing a final classifier in the form of a set of feature values for a set of mass spectrometry features forming a constitutive set of mass spectra obtained from blood-based samples of prostate cancer patients, and a final classifier defined as a majority vote or average probability cutoff, of a multitude of master classifiers constructed from a combination of mini-classifiers with dropout regularization, wherein the mini-classifiers execute a K-nearest neighbor classification algorithm on a set of features selected from the list of features set forth below:

| Left m/z | Center m/z | Right m/z |
|---|---|---|
| 3081.583 | 3090.249 | 3098.915 |
| 3308.621 | 3329.648 | 3350.675 |
| 4145.045 | 4160.911 | 4176.776 |
| 4177.923 | 4197.23 | 4216.536 |
| 4446.822 | 4468.04 | 4489.258 |
| 4556.927 | 4572.41 | 4587.894 |
| 4694.939 | 4717.304 | 4739.669 |
| 4772.094 | 4790.636 | 4809.178 |
| 4809.56 | 4824.661 | 4839.762 |
| 4846.644 | 4860.598 | 4874.552 |
| 4880.493 | 4896.55 | 4912.607 |
| 5053.678 | 5071.264 | 5088.85 |
| 5090.762 | 5109.303 | 5127.845 |
| 5279.182 | 5292.874 | 5306.565 |
| 6376.924 | 6430.949 | 6484.973 |
| 6576.342 | 6590.984 | 6605.625 |
| 6606.408 | 6652.759 | 6699.111 |
| 6782.803 | 6797.117 | 6811.43 |
| 6822.441 | 6835.653 | 6848.866 |
| 6849.6 | 6859.632 | 6869.663 |
| 6870.397 | 6891.073 | 6911.748 |
| 6928.141 | 6946.736 | 6965.332 |
| 7018.671 | 7055.25 | 7091.829 |
| 7370.816 | 7387.447 | 7404.077 |
| 7405.224 | 7419.56 | 7433.897 |
| 7514.946 | 7556.617 | 7598.289 |
| 7658.311 | 7681.058 | 7703.805 |
| 7893.703 | 7945.124 | 7996.544 |
| 7999.22 | 8034.583 | 8069.947 |
| 8181.751 | 8209.468 | 8237.185 |
| 8551.43 | 8562.293 | 8573.157 |
| 8574.723 | 8589.795 | 8604.867 |
| 8666.721 | 8691.776 | 8716.831 |
| 8730.019 | 8759.869 | 8789.72 |
| 8792.411 | 8818.347 | 8844.283 |
| 8859.941 | 8870.798 | 8881.656 |
| 8883.796 | 8923.25 | 8962.704 |
| 9043.529 | 9067.232 | 9090.935 |
| 9092.465 | 9154.245 | 9216.026 |
| 9265.334 | 9282.308 | 9299.283 |
| 9324.362 | 9346.077 | 9367.792 |
| 9368.098 | 9381.861 | 9395.624 |
| 9398.071 | 9433.855 | 9469.639 |
| 9471.168 | 9487.836 | 9504.505 |
| 9617.762 | 9641.159 | 9664.556 |
| 9690.553 | 9717.467 | 9744.382 |
| 9777.537 | 9793.747 | 9809.957 |
| 9902.628 | 9935.506 | 9968.385 |
| 10325.87 | 10347.13 | 10368.38 |
| 10430.11 | 10453.51 | 10476.9 |
| 11502.59 | 11525.29 | 11547.99 |
| 11642.19 | 11673.55 | 11704.91 |
| 11709.09 | 11730.3 | 11751.51 |
| 12525.06 | 12571.66 | 12618.25 |
| 12808.63 | 12864.18 | 12919.74 |
| 13676.71 | 13706.17 | 13735.63 |
| 13737.77 | 13758.42 | 13779.07 |
| 13781.02 | 13797.76 | 13814.5 |
| 13825.46 | 13839.55 | 13853.64 |
| 13855.09 | 13877.11 | 13899.13 |
| 13899.72 | 13913.81 | 13927.91 |
| 13928.52 | 13939.29 | 13950.05 |
| 13958.08 | 13970.19 | 13982.3 |
| 14026.12 | 14041.39 | 14056.66 |
| 14056.69 | 14066.96 | 14077.23 |
| 14612.46 | 14676.26 | 14740.06 |
| 15010.07 | 15126.44 | 15242.8 |
| 15269.09 | 15291.55 | 15314.01 |
| 15315.44 | 15345.55 | 15375.65 |
| 15724.22 | 15852.06 | 15979.89 |
| 16008.09 | 16031.26 | 16054.44 |
| 16056.83 | 16093.15 | 16129.47 |
| 16605.01 | 16682.66 | 16760.32 |
| 17091.97 | 17138.56 | 17185.16 |
| 17223.02 | 17266.27 | 17309.52 |
| 17333.41 | 17393.86 | 17454.31 |
| 17563.93 | 17601.92 | 17639.91 |
| 18598.12 | 18640.3 | 18682.49 |
| 21007.96 | 21074.42 | 21140.87 |
| 21949.42 | 22238.76 | 22528.1 |
| 27742.59 | 27978.55 | 28214.5 |
| 28227.94 | 28314.56 | 28401.17 |
| 28793.87 | 28909.23 | 29024.6 |
| 29572.29 | 29667.12 | 29761.95 |
| 3153.208 | 3164.868 | 3176.529 |
| 3353.837 | 3372.531 | 3391.224 |
| 3419.727 | 3442.492 | 3465.257 |
| 3473.03 | 3490.798 | 3508.566 |
| 4055.23 | 4068.741 | 4082.252 |
| 4137.036 | 4153.693 | 4170.351 |
| 4170.721 | 4190.155 | 4209.588 |
| 4698.8 | 4712.168 | 4725.537 |
| 4759.221 | 4802.16 | 4845.099 |

-continued

| Left m/z | Center m/z | Right m/z |
|---|---|---|
| 4983.911 | 5008.526 | 5033.142 |
| 5053.501 | 5069.418 | 5085.336 |
| 5090.443 | 5104.695 | 5118.946 |
| 5121.167 | 5133.938 | 5146.708 |
| 5525.044 | 5570.204 | 5615.365 |
| 5843.444 | 5879.72 | 5915.996 |
| 5978.924 | 6000.949 | 6022.974 |
| 6366.989 | 6387.348 | 6407.707 |
| 6409.047 | 6457.28 | 6505.514 |
| 6518.615 | 6532 | 6545.385 |
| 6623.863 | 6631.566 | 6639.268 |
| 6566.766 | 6632.507 | 6698.248 |
| 6785.31 | 6794.313 | 6803.315 |
| 6826.591 | 6838.081 | 6849.57 |
| 6850.447 | 6859.449 | 6868.452 |
| 6870.181 | 6882.263 | 6894.346 |
| 6916.615 | 6940.779 | 6964.943 |
| 7459.185 | 7488.68 | 7518.175 |
| 7526.229 | 7562.357 | 7598.486 |
| 7601.624 | 7617.379 | 7633.133 |
| 7657.771 | 7674.354 | 7690.938 |
| 7887.538 | 7929.737 | 7971.936 |
| 7976.674 | 7990.148 | 8003.622 |
| 8005.695 | 8033.827 | 8061.96 |
| 8188.822 | 8205.257 | 8221.693 |
| 8226.727 | 8238.276 | 8249.825 |
| 8651.726 | 8684.856 | 8717.985 |
| 8726.499 | 8759.074 | 8791.648 |
| 8797.941 | 8827.554 | 8857.167 |
| 8887.061 | 8931.11 | 8975.16 |
| 9041.789 | 9061.223 | 9080.657 |
| 9084.787 | 9147.53 | 9210.273 |
| 9281.714 | 9303.369 | 9325.024 |
| 9329.466 | 9346.308 | 9363.151 |
| 9366.482 | 9382.584 | 9398.686 |
| 9400.788 | 9437.805 | 9474.821 |
| 9623.278 | 9643.606 | 9663.934 |
| 9693.159 | 9709.261 | 9725.363 |
| 9727.954 | 9747.388 | 9766.821 |
| 9917.122 | 9933.965 | 9950.807 |
| 10045.12 | 10073.81 | 10102.5 |
| 10130.62 | 10227.42 | 10324.21 |
| 10326.06 | 10342.54 | 10359.01 |
| 10409.79 | 10460.69 | 10511.59 |
| 10610.05 | 10649.29 | 10688.53 |
| 10778.11 | 10838.26 | 10898.41 |
| 11501.77 | 11535.78 | 11569.79 |
| 11653.08 | 11680.38 | 11707.67 |
| 11713.23 | 11736.36 | 11759.5 |
| 12524.61 | 12570.59 | 12616.58 |
| 12768.69 | 12848.51 | 12928.32 |
| 13256.1 | 13278.08 | 13300.06 |
| 13490.6 | 13556.3 | 13622.01 |
| 13660.37 | 13699.01 | 13737.65 |
| 13740.89 | 13760.09 | 13779.29 |
| 13781.6 | 13794.79 | 13807.98 |
| 13825.56 | 13840.37 | 13855.17 |
| 13857.95 | 13878.31 | 13898.67 |
| 13901.91 | 13915.09 | 13928.28 |
| 13928.74 | 13942.62 | 13956.51 |
| 13960.21 | 13979.18 | 13998.15 |
| 14020.82 | 14048.12 | 14075.42 |
| 14078.2 | 14103.42 | 14128.63 |
| 14130.48 | 14156.63 | 14182.77 |
| 14339.49 | 14402.65 | 14465.81 |
| 14830.89 | 14885.25 | 14939.62 |
| 14941.47 | 14989.6 | 15037.72 |
| 15039.57 | 15067.33 | 15095.09 |
| 15096.02 | 15155.01 | 15214.01 |
| 15270.23 | 15291.74 | 15313.26 |
| 15314.65 | 15346.57 | 15378.5 |
| 15705.12 | 15736.59 | 15768.05 |
| 15769.44 | 15801.13 | 15832.83 |
| 15833.76 | 15867.07 | 15900.39 |
| 15901.31 | 15925.14 | 15948.97 |
| 15951.75 | 15981.59 | 16011.43 |
| 16014.21 | 16034.34 | 16054.47 |

-continued

| Left m/z | Center m/z | Right m/z |
|---|---|---|
| 16055.85 | 16088.94 | 16122.02 |
| 16125.23 | 16148 | 16170.78 |
| 16175.11 | 16204.76 | 16234.4 |
| 16600.22 | 16666.38 | 16732.53 |
| 17222.34 | 17246.92 | 17271.5 |
| 17272.23 | 17288.13 | 17304.04 |
| 17358.26 | 17377.42 | 17396.58 |
| 17398.03 | 17417.91 | 17437.79 |
| 17852.61 | 17901.41 | 17950.21 |
| 18594.98 | 18622.82 | 18650.65 |
| 18652.82 | 18677.4 | 18701.98 |
| 20902.69 | 20954.66 | 21006.62 |
| 21011.14 | 21064.46 | 21117.78 |
| 23258.31 | 23571.9 | 23885.49 |
| 27660.21 | 27839.26 | 28018.31 |
| 28019.44 | 28098.51 | 28177.59 |
| 28227.29 | 28315.97 | 28404.65 |
| 28815.5 | 28888.93 | 28962.36 |
| 3073.625 | 3085.665 | 3097.705 |
| 3098.586 | 3109.891 | 3121.197 |
| 3123.546 | 3138.669 | 3153.793 |
| 3190.793 | 3210.615 | 3230.436 |
| 3230.73 | 3242.623 | 3254.516 |
| 3255.103 | 3264.647 | 3274.191 |
| 3296.802 | 3316.77 | 3336.739 |
| 3349.072 | 3363.608 | 3378.144 |
| 3380.2 | 3391.946 | 3403.692 |
| 3405.16 | 3420.283 | 3435.407 |
| 3435.7 | 3445.097 | 3454.494 |
| 3454.788 | 3465.359 | 3475.931 |
| 3490.725 | 3508.305 | 3525.884 |
| 3531.431 | 3553.896 | 3576.36 |
| 3581.059 | 3593.099 | 3605.138 |
| 3665.631 | 3679.286 | 3692.941 |
| 3693.94 | 3712.036 | 3730.132 |
| 3745.211 | 3754.755 | 3764.299 |
| 3764.592 | 3775.604 | 3786.616 |
| 3798.592 | 3814.263 | 3829.933 |
| 3831.545 | 3841.53 | 3851.514 |
| 3876.474 | 3887.486 | 3898.499 |
| 3898.583 | 3906.18 | 3913.777 |
| 3914.356 | 3928.158 | 3941.959 |
| 3942.253 | 3953.412 | 3964.571 |
| 3994.23 | 4008.619 | 4023.008 |
| 4024.182 | 4031.67 | 4039.159 |
| 4039.452 | 4050.464 | 4061.476 |
| 4086.437 | 4098.77 | 4111.104 |
| 4111.308 | 4118.525 | 4125.742 |
| 4126.043 | 4133.109 | 4140.176 |
| 4198.812 | 4209.788 | 4220.764 |
| 4241.573 | 4249.445 | 4257.316 |
| 4258.28 | 4265.83 | 4273.38 |
| 4273.837 | 4286.166 | 4298.495 |
| 4328.264 | 4340.217 | 4352.17 |
| 4352.32 | 4360.815 | 4369.31 |
| 4369.611 | 4380.962 | 4392.314 |
| 4393.817 | 4408.627 | 4423.436 |
| 4424.789 | 4431.179 | 4437.569 |
| 4437.87 | 4459.22 | 4480.57 |
| 4496.507 | 4506.58 | 4516.654 |
| 4552.738 | 4564.991 | 4577.245 |
| 4577.384 | 4592.602 | 4607.819 |
| 4616.938 | 4625.282 | 4633.627 |
| 4633.927 | 4643.324 | 4652.721 |
| 4664.148 | 4675.274 | 4686.4 |
| 4690.609 | 4717.673 | 4744.736 |
| 4746.54 | 4756.162 | 4765.785 |
| 4766.386 | 4773.152 | 4779.918 |
| 4780.218 | 4791.194 | 4802.17 |
| 4802.621 | 4817.881 | 4833.142 |
| 4836.299 | 4855.995 | 4875.691 |
| 4880.953 | 4891.177 | 4901.401 |
| 4909.52 | 4918.316 | 4927.111 |
| 4927.261 | 4937.636 | 4948.01 |
| 4948.16 | 4963.045 | 4977.93 |
| 4987.552 | 4998.979 | 5010.405 |
| 5011.007 | 5020.103 | 5029.199 |

| Left m/z | Center m/z | Right m/z |
|---|---|---|
| 5029.65 | 5041.077 | 5052.504 |
| 5053.556 | 5067.839 | 5082.123 |
| 5087.535 | 5104.074 | 5120.613 |
| 5121.383 | 5134.355 | 5147.326 |
| 5149.837 | 5156.322 | 5162.808 |
| 5164.9 | 5181.637 | 5198.375 |
| 5209.77 | 5223.753 | 5237.736 |
| 5238.036 | 5247.734 | 5257.432 |
| 5275.624 | 5289.757 | 5303.89 |
| 5347.191 | 5358.543 | 5369.894 |
| 5370.646 | 5377.186 | 5383.726 |
| 5383.877 | 5389.815 | 5395.754 |
| 5395.905 | 5403.422 | 5410.94 |
| 5411.09 | 5416.277 | 5421.464 |
| 5421.615 | 5429.809 | 5438.003 |
| 5439.807 | 5449.204 | 5458.601 |
| 5463.713 | 5472.057 | 5480.402 |
| 5481.454 | 5495.813 | 5510.171 |
| 5510.472 | 5521.222 | 5531.972 |
| 5535.439 | 5557.829 | 5580.219 |
| 5663.828 | 5675.387 | 5686.946 |
| 5696.097 | 5709.823 | 5723.549 |
| 5740.923 | 5748.044 | 5755.165 |
| 5756.127 | 5762.381 | 5768.636 |
| 5769.502 | 5776.671 | 5783.84 |
| 5787.496 | 5795.483 | 5803.469 |
| 5803.95 | 5815.979 | 5828.007 |
| 5828.68 | 5842.055 | 5855.431 |
| 5856.297 | 5867.218 | 5878.14 |
| 5879.39 | 5889.157 | 5898.924 |
| 5899.02 | 5910.808 | 5922.595 |
| 5924.106 | 5934.47 | 5944.834 |
| 5946.068 | 5961.861 | 5977.654 |
| 5978.694 | 5997.458 | 6016.222 |
| 6016.895 | 6026.806 | 6036.717 |
| 6052.178 | 6074.758 | 6097.337 |
| 6099.552 | 6108.597 | 6117.642 |
| 6161.136 | 6170.373 | 6179.611 |
| 6184.807 | 6192.938 | 6201.069 |
| 6201.261 | 6209.585 | 6217.908 |
| 6218.004 | 6226.039 | 6234.074 |
| 6245.993 | 6254.58 | 6263.166 |
| 6273.718 | 6283.244 | 6292.771 |
| 6292.867 | 6301.238 | 6309.61 |
| 6321.927 | 6331.742 | 6341.556 |
| 6349.371 | 6357.324 | 6365.277 |
| 6379.18 | 6386.108 | 6393.037 |
| 6393.229 | 6399.965 | 6406.7 |
| 6408.625 | 6437.829 | 6467.033 |
| 6467.129 | 6485.171 | 6503.214 |
| 6520.161 | 6531.72 | 6543.279 |
| 6548.095 | 6556.042 | 6563.989 |
| 6577.691 | 6589.431 | 6601.17 |
| 6603.961 | 6611.61 | 6619.26 |
| 6620.319 | 6634.319 | 6648.32 |
| 6648.512 | 6657.076 | 6665.64 |
| 6668.623 | 6680.651 | 6692.68 |
| 6700.438 | 6707.101 | 6713.764 |
| 6719.237 | 6731.65 | 6744.063 |
| 6744.599 | 6755.677 | 6766.754 |
| 6767.638 | 6773.171 | 6778.704 |
| 6786.982 | 6792.762 | 6798.542 |
| 6799.97 | 6808.919 | 6817.868 |
| 6824.892 | 6836.679 | 6848.467 |
| 6848.948 | 6859.629 | 6870.31 |
| 6873.797 | 6881.433 | 6889.07 |
| 6890.609 | 6897.599 | 6904.589 |
| 6914.565 | 6921.586 | 6928.606 |
| 6933.102 | 6941.477 | 6949.853 |
| 6950.469 | 6956.75 | 6963.032 |
| 6963.34 | 6970.545 | 6977.75 |
| 6978.92 | 6992.222 | 7005.524 |
| 7014.269 | 7022.06 | 7029.85 |
| 7029.912 | 7034.592 | 7039.272 |
| 7039.395 | 7045.154 | 7050.912 |
| 7067.293 | 7073.79 | 7080.287 |
| 7119.824 | 7147.228 | 7174.633 |
| 7177.589 | 7188.951 | 7200.314 |
| 7232.783 | 7257.933 | 7283.084 |
| 7292.812 | 7300.633 | 7308.454 |
| 7316.187 | 7321.946 | 7327.705 |
| 7327.772 | 7333.817 | 7339.863 |
| 7339.896 | 7346.093 | 7352.29 |
| 7352.819 | 7360.754 | 7368.688 |
| 7379.768 | 7393.009 | 7406.249 |
| 7406.3 | 7419.793 | 7433.287 |
| 7433.608 | 7447.584 | 7461.56 |
| 7463.692 | 7479.362 | 7495.032 |
| 7497.824 | 7510.356 | 7522.889 |
| 7731.041 | 7738.801 | 7746.561 |
| 7761.341 | 7779.077 | 7796.813 |
| 7808.996 | 7828.02 | 7847.044 |
| 7849.362 | 7871.424 | 7893.485 |
| 7904.954 | 7912.836 | 7920.719 |
| 8007.424 | 8015.07 | 8022.717 |
| 8134.028 | 8157.158 | 8180.287 |
| 8195.752 | 8206.991 | 8218.23 |
| 8238.737 | 8253.917 | 8269.098 |
| 8304.472 | 8328.669 | 8352.866 |
| 8353.406 | 8363.536 | 8373.667 |
| 8380.133 | 8391.495 | 8402.857 |
| 8404.767 | 8413.388 | 8422.01 |
| 8422.133 | 8430.231 | 8438.33 |
| 8457.421 | 8464.072 | 8470.723 |
| 8470.846 | 8477.558 | 8484.271 |
| 8497.292 | 8508.651 | 8520.011 |
| 8520.544 | 8531.198 | 8541.852 |
| 8554.723 | 8564.761 | 8574.799 |
| 8575.476 | 8585.268 | 8595.06 |
| 8618.77 | 8631.702 | 8644.635 |
| 8649.87 | 8660.554 | 8671.239 |
| 8671.855 | 8696.119 | 8720.383 |
| 8720.568 | 8728.512 | 8736.456 |
| 8736.518 | 8745.817 | 8755.116 |
| 8756.348 | 8770.604 | 8784.861 |
| 8791.574 | 8796.962 | 8802.351 |
| 8802.474 | 8822.181 | 8841.887 |
| 8861.964 | 8871.848 | 8881.732 |
| 8883.826 | 8890.538 | 8897.251 |
| 8897.436 | 8901.654 | 8905.873 |
| 8905.934 | 8928.258 | 8950.582 |
| 8967.272 | 8974.415 | 8981.559 |
| 8988.149 | 8997.971 | 9007.794 |
| 9010.011 | 9020.295 | 9030.58 |
| 9030.764 | 9038.216 | 9045.668 |
| 9055.367 | 9062.134 | 9068.902 |
| 9069.184 | 9079.194 | 9089.205 |
| 9091.547 | 9097.798 | 9104.049 |
| 9115.171 | 9134.336 | 9153.501 |
| 9196.082 | 9206.437 | 9216.792 |
| 9217.991 | 9226.317 | 9234.643 |
| 9234.742 | 9244.546 | 9254.35 |
| 9254.941 | 9263.932 | 9272.924 |
| 9273.256 | 9291.73 | 9310.203 |
| 9310.761 | 9318.865 | 9326.969 |
| 9344.962 | 9359.289 | 9373.615 |
| 9387.662 | 9395.293 | 9402.923 |
| 9410.817 | 9430.014 | 9449.211 |
| 9475.524 | 9484.41 | 9493.296 |
| 9494.536 | 9504.042 | 9513.549 |
| 9520.898 | 9534.803 | 9548.707 |
| 9559.484 | 9576.179 | 9592.874 |
| 9615.006 | 9641.179 | 9667.352 |
| 9689.387 | 9720.901 | 9752.414 |
| 9784.265 | 9793.021 | 9801.777 |
| 9840.895 | 9862.594 | 9884.294 |
| 9908.49 | 9918.931 | 9929.371 |
| 9929.66 | 9941.495 | 9953.331 |
| 10002.41 | 10012.36 | 10022.32 |
| 10066.88 | 10079.24 | 10091.61 |
| 10091.7 | 10102.24 | 10112.77 |
| 10120.09 | 10135.29 | 10150.49 |
| 10150.78 | 10162.62 | 10174.45 |
| 10174.65 | 10185.23 | 10195.82 |

-continued

| Left m/z | Center m/z | Right m/z |
|---|---|---|
| 10195.91 | 10210.35 | 10224.78 |
| 10225.16 | 10236.04 | 10246.91 |
| 10250.09 | 10263.03 | 10275.97 |
| 10276.55 | 10285.11 | 10293.68 |
| 10295 | 10313.15 | 10331.3 |
| 10333.03 | 10346.26 | 10359.49 |
| 10359.69 | 10365.85 | 10372 |
| 10408.98 | 10420.87 | 10432.75 |
| 10436.76 | 10448.55 | 10460.34 |
| 10472.41 | 10480.21 | 10488.01 |
| 10488.32 | 10503.84 | 10519.36 |
| 10521.66 | 10532.67 | 10543.68 |
| 10543.99 | 10551.18 | 10558.36 |
| 10573.66 | 10589.18 | 10604.71 |
| 10615.84 | 10636.81 | 10657.79 |
| 10705.55 | 10734.07 | 10762.59 |
| 10773.07 | 10782.59 | 10792.12 |
| 10792.19 | 10804.96 | 10817.72 |
| 10827.72 | 10846.77 | 10865.83 |
| 10912.98 | 10923.56 | 10934.15 |
| 10954.02 | 10965.58 | 10977.14 |
| 11035.47 | 11057.93 | 11080.38 |
| 11092.07 | 11107.19 | 11122.31 |
| 11137.08 | 11149.06 | 11161.04 |
| 11288.09 | 11306.44 | 11324.78 |
| 11357.26 | 11375.9 | 11394.54 |
| 11396.27 | 11410.09 | 11423.9 |
| 11425.13 | 11447.54 | 11469.96 |
| 11505.19 | 11532.05 | 11558.92 |
| 11613 | 11627.24 | 11641.47 |
| 11642.18 | 11654.28 | 11666.38 |
| 11666.74 | 11688.44 | 11710.15 |
| 11712.08 | 11733.43 | 11754.78 |
| 11756.23 | 11786.66 | 11817.09 |
| 11817.93 | 11834.77 | 11851.61 |
| 11868.93 | 11898.52 | 11928.11 |
| 11928.7 | 11944.87 | 11961.05 |
| 12143.52 | 12158.28 | 12173.04 |
| 12271.47 | 12290.85 | 12310.22 |
| 12400.43 | 12412.62 | 12424.81 |
| 12433.83 | 12457.39 | 12480.94 |
| 12489.93 | 12507.27 | 12524.61 |
| 12536.4 | 12565.8 | 12595.2 |
| 12597.2 | 12613.41 | 12629.61 |
| 12647.98 | 12674.21 | 12700.44 |
| 12716.47 | 12738.02 | 12759.57 |
| 12761.24 | 12785.79 | 12810.35 |
| 12829.73 | 12873.16 | 12916.59 |
| 12935.63 | 12967.54 | 12999.44 |
| 13051.23 | 13080.96 | 13110.69 |
| 13117.71 | 13134.41 | 13151.12 |
| 13225.86 | 13241.27 | 13256.68 |
| 13258.69 | 13274.73 | 13290.77 |
| 13304.99 | 13318.16 | 13331.32 |
| 13347.56 | 13364.6 | 13381.64 |
| 13402.57 | 13413.92 | 13425.28 |
| 13510.26 | 13524.96 | 13539.66 |
| 13551.35 | 13567.72 | 13584.09 |
| 13597.13 | 13624.17 | 13651.21 |

-continued

| Left m/z | Center m/z | Right m/z |
|---|---|---|
| 13703.7 | 13721.07 | 13738.44 |
| 13740.45 | 13762.16 | 13783.88 |
| 13784.55 | 13798.24 | 13811.94 |
| 13826.64 | 13842.84 | 13859.05 |
| 13864.06 | 13882.93 | 13901.81 |
| 13903.15 | 13916.01 | 13928.87 |
| 13929.67 | 13943.07 | 13956.27 |
| 13958.61 | 13983.66 | 14008.72 |
| 14015.73 | 14042.8 | 14069.86 |
| 14076.2 | 14097.59 | 14118.97 |
| 14124.31 | 14149.03 | 14173.76 |
| 14178.77 | 14198.98 | 14219.19 |
| 14231.55 | 14254.61 | 14277.66 |
| 14281.33 | 14306.56 | 14331.78 |
| 14461.45 | 14515 | 14568.55 |
| 14751.73 | 14784.47 | 14817.21 |
| 14857.63 | 14884.53 | 14911.42 |
| 14949.73 | 14975.44 | 15001.15 |
| 15009.14 | 15028.79 | 15048.44 |
| 15527.48 | 15563.22 | 15598.97 |
| 15713.63 | 15753.95 | 15794.27 |
| 16465.93 | 16502.17 | 16538.42 |
| 16610.92 | 16630.13 | 16649.34 |
| 16999.46 | 17032.54 | 17065.61 |
| 17104.03 | 17148.13 | 17192.23 |
| 17225.64 | 17270.91 | 17316.18 |
| 17318.65 | 17335.6 | 17352.55 |
| 17359.48 | 17401.7 | 17443.93 |
| 17445.13 | 17476.37 | 17507.61 |
| 17569.08 | 17604.33 | 17639.57 |
| 17774.54 | 17815.47 | 17856.39 |
| 17982.34 | 18031.12 | 18079.9 |
| 18232.58 | 18275.34 | 18318.1 |
| 18593.72 | 18636.99 | 18680.25 |
| 18816.22 | 18850.13 | 18884.04 |
| 19339.07 | 19373.15 | 19407.22 |
| 19407.56 | 19463.85 | 19520.15 |
| 19522.82 | 19575.27 | 19627.72 |
| 20740.85 | 20811.99 | 20883.14 |
| 20886.89 | 20945.69 | 21004.49 |
| 21005.16 | 21061.95 | 21118.75 |
| 21119.42 | 21170.37 | 21221.31 |
| 21221.98 | 21275.44 | 21328.89 |
| 21330.89 | 21377.17 | 21423.44 |
| 21428.09 | 21475.32 | 21522.55 |
| 21642.26 | 21687.7 | 21733.13 |
| 21733.61 | 21755.74 | 21777.87 |
| 21778.15 | 21807.79 | 21837.44 |
| 21837.72 | 21862.69 | 21887.65 |
| 21887.93 | 21917.15 | 21946.37 |
| 22967.23 | 23036.05 | 23104.87 |
| 23110.29 | 23160.86 | 23211.44 |
| 23212.98 | 23256.28 | 23299.59 |
| 23407.68 | 23468.85 | 23530.03 |
| 27630.18 | 27715.9 | 27801.62 |
| 27874.33 | 27944.17 | 28014.01 |
| 28015.03 | 28082.32 | 28149.61. |

* * * * *